United States Patent
Remiszewski et al.

(10) Patent No.: US 10,556,894 B2
(45) Date of Patent: Feb. 11, 2020

(54) ANTI-HCMV COMPOSITIONS AND METHODS

(71) Applicant: FORGE Life Science, LLC, Doylestown, PA (US)

(72) Inventors: Stacy Remiszewski, Doylestown, PA (US); Emre Koyuncu, Doylestown, PA (US); Qun Sun, Princeton, PA (US); Lillian Chiang, Princeton, NJ (US)

(73) Assignee: Evrys Bio, LLC, Doylestown, PA (US)

( * ) Notice: Subject to any disclaimer, the term of this patent is extended or adjusted under 35 U.S.C. 154(b) by 0 days.

(21) Appl. No.: 15/525,504

(22) PCT Filed: Nov. 9, 2015

(86) PCT No.: PCT/US2015/059746
§ 371 (c)(1),
(2) Date: May 9, 2017

(87) PCT Pub. No.: WO2016/077232
PCT Pub. Date: May 19, 2016

(65) Prior Publication Data
US 2018/0291016 A1    Oct. 11, 2018

Related U.S. Application Data

(60) Provisional application No. 62/077,804, filed on Nov. 10, 2014.

(51) Int. Cl.
| | | |
|---|---|---|
| *C07D 417/14* | (2006.01) |
| *A61K 31/427* | (2006.01) |
| *C07D 417/04* | (2006.01) |
| *C07D 491/052* | (2006.01) |
| *C07D 417/06* | (2006.01) |
| *C07D 417/10* | (2006.01) |
| *A61K 45/06* | (2006.01) |
| *A61K 31/436* | (2006.01) |
| *A61K 31/4725* | (2006.01) |
| *A61K 31/498* | (2006.01) |
| *A61K 31/5377* | (2006.01) |
| *A61K 31/506* | (2006.01) |
| *A61K 31/4709* | (2006.01) |

(52) U.S. Cl.
CPC .......... *C07D 417/14* (2013.01); *A61K 31/427* (2013.01); *A61K 31/436* (2013.01); *A61K 31/4709* (2013.01); *A61K 31/4725* (2013.01); *A61K 31/498* (2013.01); *A61K 31/506* (2013.01); *A61K 31/5377* (2013.01); *A61K 45/06* (2013.01); *C07D 417/04* (2013.01); *C07D 417/06* (2013.01); *C07D 417/10* (2013.01); *C07D 491/052* (2013.01)

(58) Field of Classification Search
CPC .................................................... C07D 417/14
See application file for complete search history.

(56) References Cited

U.S. PATENT DOCUMENTS

| | | | | |
|---|---|---|---|---|
| 5,232,921 | A | * | 8/1993 | Biziere ............... C07D 277/42 514/231.5 |
| 6,057,451 | A | | 5/2000 | Crute et al. |
| 2015/0335657 | A1 | | 11/2015 | Shenk |

FOREIGN PATENT DOCUMENTS

| | | | |
|---|---|---|---|
| EP | 0283390 A2 | | 9/1988 |
| WO | 2007/009578 A1 | | 1/2007 |
| WO | WO 2012160015 | * | 11/2012 ............. C07B 59/00 |

OTHER PUBLICATIONS

"Cytomegalovirus", https://www.cdc.gov/cmv/congenital-infection.html, accessed Mar. 11, 2019, page last reviewed Jun. 6, 2018 (Year: 2018).*
Fu. Vaccine, 2014, 32, 2525-33 (Year: 2014).*
Chemical Abstracts Service, Columbus Ohio, US; Apr. 15, 2012 Database Accession No. 1368401-75-5.
Chemical Abstracts Service, Columbus Ohio, US; Dec. 30, 2002 Database Accession No. 477762-17-7.
Chemical Abstracts Service, Columbus Ohio, US; Oct. 26, 2005 Database Accession No. 688137-05-5.
Apr. 10, 2019 Communication From the Examining Division for Related EP Patent Application 15859814.4.

* cited by examiner

*Primary Examiner* — Noble E Jarrell
(74) *Attorney, Agent, or Firm* — F. Aaron Dubberley

(57) ABSTRACT

Novel compounds useful for treating and/or preventing HCMV infections are provided.

24 Claims, No Drawings

ANTI-HCMV COMPOSITIONS AND METHODS

STATEMENT OF FEDERALLY FUNDED RESEARCH

This invention was made with government support under grant number R43 AI110048 awarded by the National Institutes of Health. The government has certain rights to the invention.

TECHNICAL FIELD

This document relates to compounds useful for preventing, treating or ameliorating human cytomegalovirus infection.

BACKGROUND

Human cytomegalovirus (HCMV) is a major cause of birth defects and opportunistic infections in immunosuppressed individuals, and a possible cofactor in certain cancers. Organ transplant patients under immunosuppressive therapy are at high risk for viral infections; activation of a latent virus as well as donor or community acquired primary infections can cause significant complications including graft rejection, morbidity, and mortality. Herpesviruses (e.g. HCMV, HSV-1), polyomaviruses (e.g. BKV and JCV), hepatitis viruses (HBV and HCV) and respiratory viruses (e.g. influenza A, adenovirus) are the 4 major viral classes infecting these patients. Cytomegalovirus (HCMV) is the most prevalent post-transplant pathogen; HCMV can infect most organs, and despite the availability of HCMV antivirals such as ganciclovir, nephrotoxic side effects and increasing rates of drug-resistance significantly reduce graft and patient survival. In addition, HCMV-mediated immune modulation can reactivate distinct latent viruses carried by most adults.

SUMMARY

The invention provides compounds having the structure of Formula I:

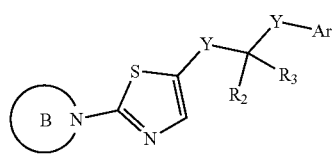

Formula I wherein:

Ar is

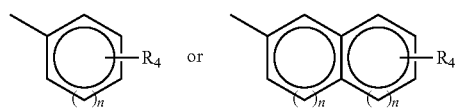

wherein each cyclic 5- or 6-membered ring in Ar optionally contains up to two N heteroatoms, Y is, independently in each instance, C or a bond, Ring B is selected from the group consisting of:

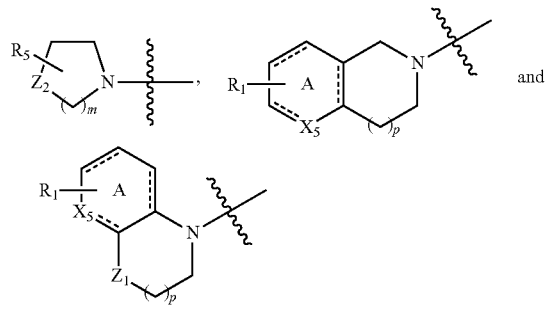

m is 0, 1 or 2,
n is, independently in each instance, 0 or 1,
p is 0 or 1,
when p is 0, $Z_1$ is C,
when p is 1, $Z_1$ is C, O, S or $NR_7$
$R_1$ is H, halo, —CN, —$NO_2$, —C(O)$NR_6R_7$, or C(O)$OR_6$,
$R_2$ is H or a lower straight or branched alkyl or alkenyl optionally substituted with one heteroatom selected of N and O,
$R_3$ is H or OH,
$R_4$ is H or a saturated 5- or 6-membered aryl or cycloalkyl with up to two heteroatoms selected from N, O and S,
$R_5$ is H, —$OR_7$, or —$NR_6R_7$,
$R_6$ and $R_7$ are independently selected in each instance from H and lower straight chain or branched alkyl,
when Ring A is aromatic, $X_5$ is C or N,
when Ring A is not aromatic, $X_5$ is C, O, S or $NR_7$,
when m=0 or 1, $Z_2$ is C, and
when m=2, $Z_2$ is C, O, S or $NR_7$;

The compounds of the invention are useful for treating and/or preventing HCMV infections.

The invention also provides methods of preventing, treating and/or ameliorating HCMV infections with compounds of Formula I.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Provided herein are compounds useful in the treatment and/or prevention of HCMV infections.

Provided herein are methods for treating or preventing a HCMV infection in a subject. In some embodiments, the methods include administering a therapeutically effective amount of one or more of the compounds provided herein. In some embodiments, the compounds provided herein can inhibit HCMV production in a cell infected with the virus. In such embodiments, the cell is contacted with a virus production inhibiting amount of one or more compounds provided herein.

Provided herein are compounds of the structure of Formula I:

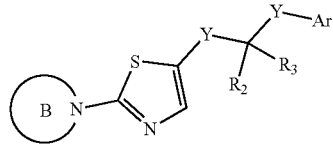

Formula I wherein:
Ar is

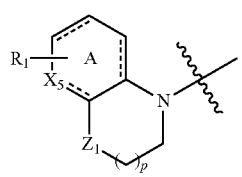

wherein each cyclic 5- or 6-membered ring in Ar optionally contains up to two N heteroatoms,
Y is, independently in each instance, C or a bond,
Ring B is selected from the group consisting of:

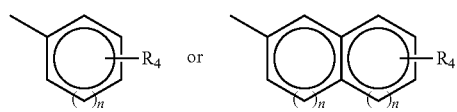

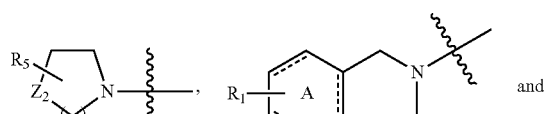

m is 0, 1 or 2,
n is, independently in each instance, 0 or 1,
p is 0 or 1,
when p is 0, $Z_1$ is C,
when p is 1, $Z_1$ is C, O, S or $NR_7$
$R_1$ is H, halo, —CN, —$NO_2$, —C(O)$NR_6R_7$, or C(O)$OR_6$,
$R_2$ is H or a lower straight or branched alkyl or alkenyl optionally substituted with one heteroatom selected of N and O,
$R_3$ is H or OH,
$R_4$ is H or a saturated 5- or 6-membered aryl or cycloalkyl with up to two heteroatoms selected from N, O and S,
$R_5$ is H, —$OR_7$, or —$NR_6R_7$,
$R_6$ and $R_7$ are independently selected in each instance from H and lower straight chain or branched alkyl,
when Ring A is aromatic, $X_5$ is C or N,
when Ring A is not aromatic, $X_5$ is C, O, S or $NR_7$,
when m=0 or 1, $Z_2$ is C, and
when m=2, $Z_2$ is C, O, S or $NR_7$;
or a pharmaceutically acceptable salt thereof, with the proviso that the compound is not:

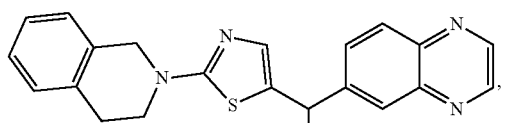

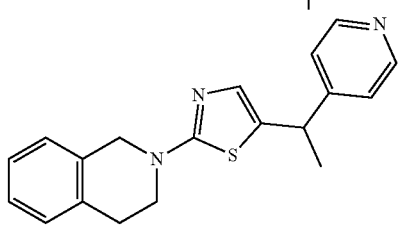

or a pharmaceutically acceptable salt thereof.
The compounds of Formula I are useful for preventing, treating and/or ameliorating a HCMV infection.
Some embodiments of the of the anti-HCMV compounds provided herein have the structure of Formula II,

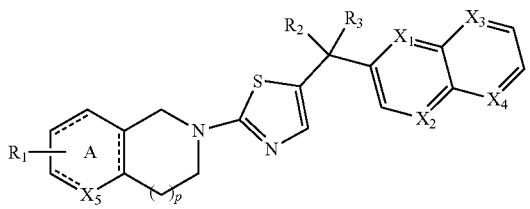

Formula II wherein $X_1$, $X_2$, $X_3$ and $X_4$ are independently selected from C and N and all the other variables are as defined for Formula I,
or a pharmaceutically acceptable salt thereof, with the proviso that the compound is not

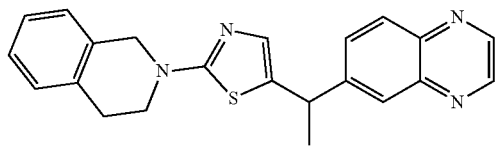 [SMILES: CC(c1ccc2nccnc2c1)c1cnc(N2CCc3ccccc3C2)s1]

or a pharmaceutically acceptable salt thereof.
Some embodiments of the of the anti-HCMV compounds provided herein have the structure of Formula III,

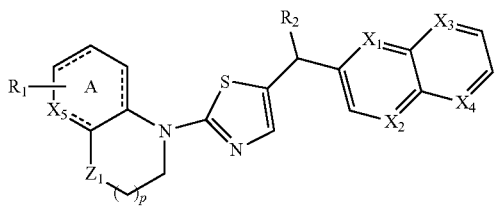

Formula III wherein $X_1$, $X_2$, $X_3$ and $X_4$ are independently selected from C and N and all the other variables are as defined for Formula I,
or a pharmaceutically acceptable salt thereof.

Some embodiments of the of the anti-HCMV compounds provided herein have the structure of Formula IV,

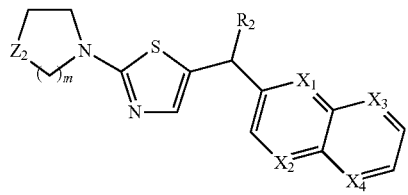

Formula IV wherein $X_1$, $X_2$, $X_3$ and $X_4$ are independently selected from C and N and all other variables are as defined for Formula I,
or a pharmaceutically acceptable salt thereof.
Some embodiments of the of the anti-HCMV compounds provided herein have the structure of Formula V,

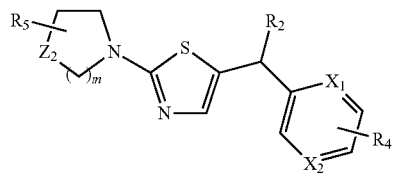

Formula V wherein $X_1$ and $X_2$ are independently selected from C and N and all other variables are as defined in Formula I,
or a pharmaceutically acceptable salt thereof.
Some embodiments of the of the anti-HCMV compounds provided herein have the structure of Formula VI,

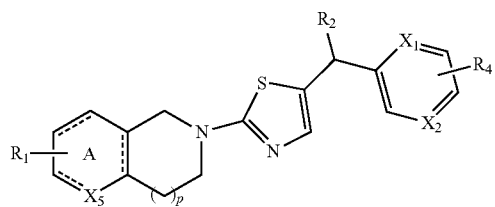

Formula VI wherein $X_1$ and $X_2$ are independently selected from C and N and all other variables are as defined for Formula I,
or a pharmaceutically acceptable salt thereof.
Some embodiments of the of the anti-HCMV compounds provided herein have the structure of Formula VII, The composition of claim 1, comprising a compound of Formula VII or a pharmaceutically acceptable salt thereof:

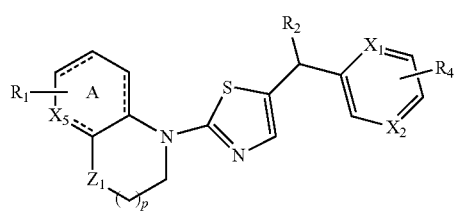

Formula VII wherein $X_1$ and $X_2$ are independently selected from C and N, and all other variables are defined as in Formula I,
or a pharmaceutically acceptable salt thereof.

In some embodiments of the compounds of Formulas V, VI and VII, $R_4$ is in the meta or para position and is selected from the group consisting of pyrrole, imidazole, pyrazole, pyrazine, pyrimidine and pyridazine.

In some embodiments of the compounds of Formulas I, II, III, V, VI and VII, $R_1$, if present in the formula, is H, halo, —CN, or —NO$_2$, and $R_4$, if present in the formula, is a saturated 5- or 6-membered aryl or cycloalkyl with up to two heteroatoms selected from N, O and S.

In some embodiments of the compounds of Formula I, the compound is selected from the group consisting of:

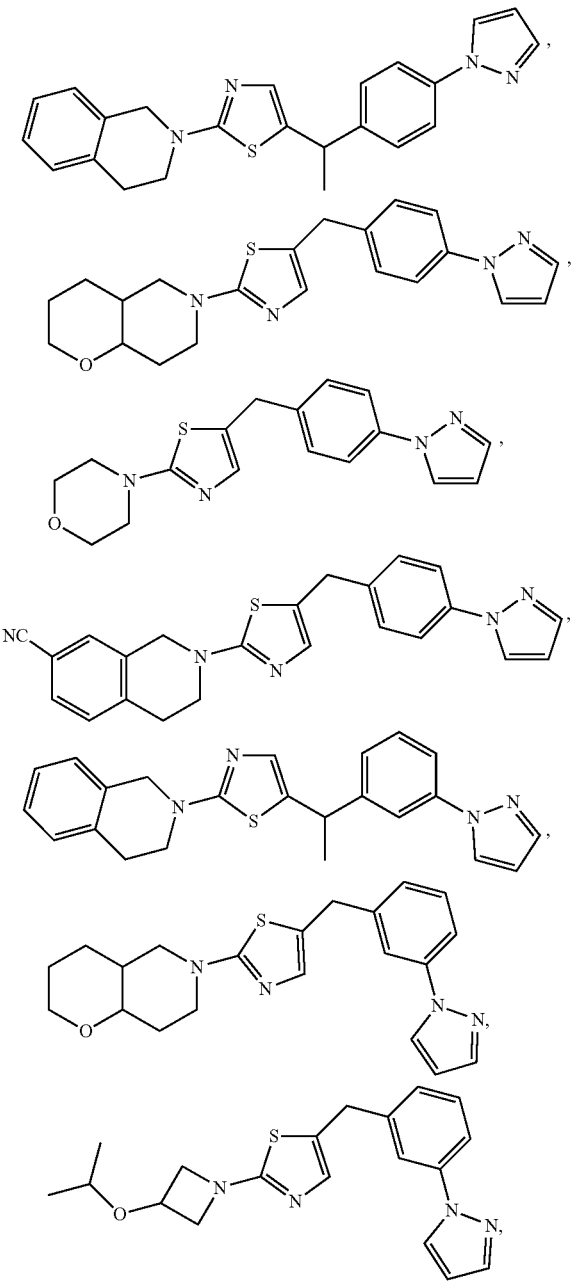

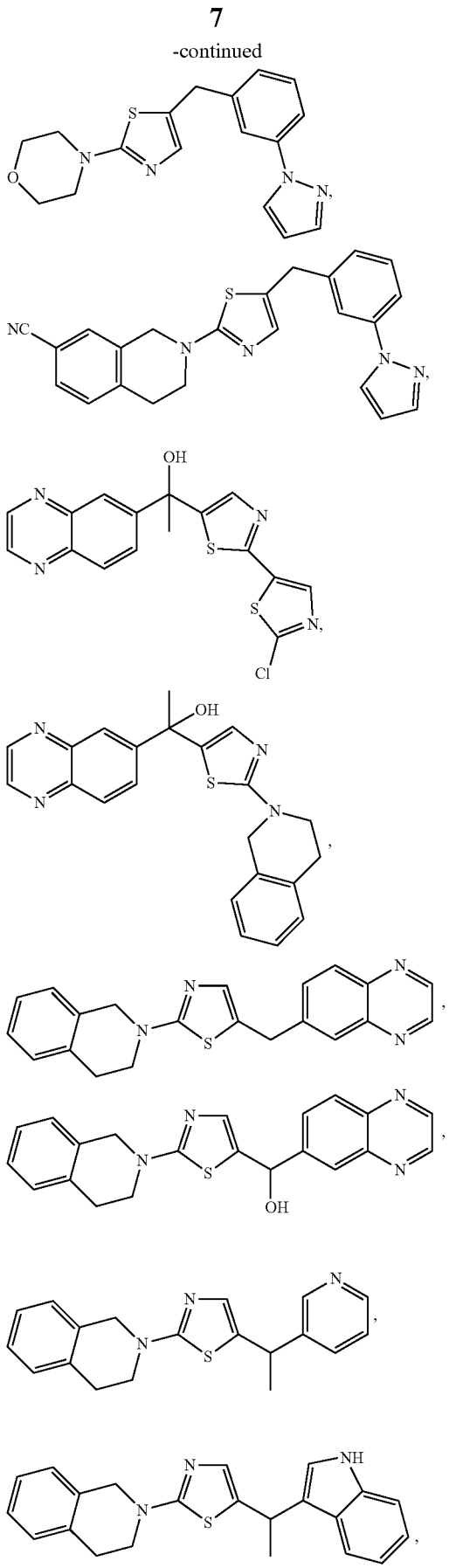
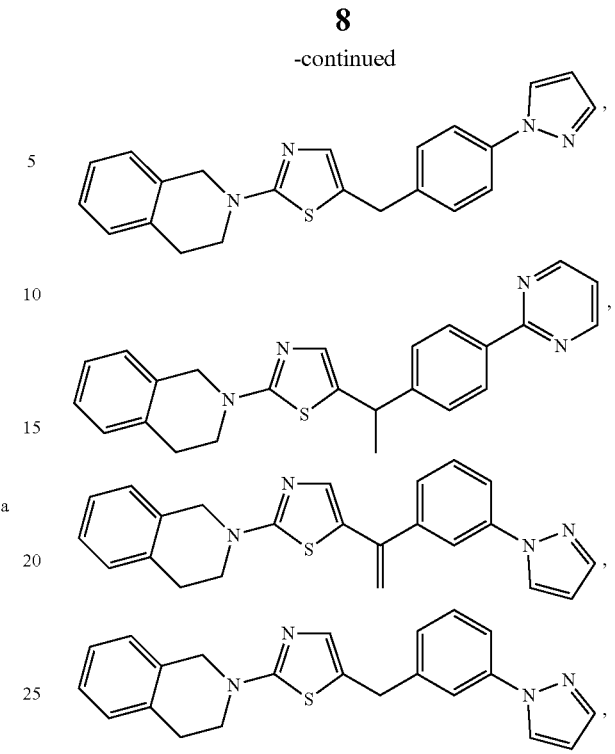

and pharmaceutically acceptable salts thereof.

Some embodiments of the method for treating or preventing a HCMV infection in a subject provided herein can include administering a therapeutically effective amount of a compound of Formula I, Formula II, Formula III, Formula IV, Formula V, Formula VI, Formula VII or pharmaceutically acceptable salts thereof.

Also provided herein is a method of inhibiting HCMV production comprising contacting a HCMV-infected cell with a virus production inhibiting amount of any of the compounds of Formulas I, II, III, IV, V, VI and VII.

An antiviral agent can also be administered in conjunction with the compounds and the methods described herein. The agent can be any therapeutic agent useful in the treatment of a HCMV infection. For example, an antiviral agent can include acyclovir, docosanol, ribarivin, interferons, and the like; cellulose acetate, carbopol and carrageenan, pleconaril, amantidine, rimantidine, fomivirsen, zidovudine, lamivudine, zanamivir, oseltamivir, brivudine, abacavir, adefovir, amprenavir, arbidol, atazanavir, atripla, cidofovir, combivir, edoxudine, efavirenz, emtricitabine, enfuvirtide, entecavir, famciclovir, fosamprenavir, foscarnet, fosfonet, ganciclovir, gardasil, ibacitabine, imunovir, idoxuridine, imiquimod, indinavir, inosine, integrase inhibitor, lamivudine, lopinavir, loviride, mk-0518, maraviroc, moroxydine, nelfinavir, nevirapine, nexavir, nucleotide and/or nucleoside analogues, oseltamivir, penciclovir, peramivir, podophyllotoxin, rimantadine, ritonavir, saquinavir, stavudine, tenofovir, tenofovir disoproxil, tipranavir, trifluridine, trizivir, tromantadine, truvada, valaciclovir, valganciclovir, vicriviroc, vidarabine, viramidine, zalcitabine, morpholino oligonucleotides, ribozyme, protease inhibitors, an assembly inhibitor (e.g., rifampicin), zidovudine, brincidofovir, favipiravir, nitoxanide, letermovir, maribavir, CMX157 or a combination or two or more antiviral agents.

In some embodiments, a compound provided herein can be administered before, after, or simultaneously with the administration or one or more antiviral agents.

A compound provided herein, including a pharmaceutically acceptable salt thereof, can be purchased commercially or prepared using known organic synthesis techniques.

The methods provided herein include the manufacture and use of pharmaceutical compositions, which include compounds provided herein and one or more pharmaceutically acceptable carriers. Also provided herein are the compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

A pharmaceutical composition is typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., Remington: The Science and Practice of Pharmacy, 21st ed., 2005; and the books in the series Drugs and the Pharmaceutical Sciences: a Series of Textbooks and Monographs (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injection can include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. The composition should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate and gelatin.

Sterile injectable solutions can be prepared by incorporating a compound provided herein in the required amount in an appropriate solvent with one or a combination of ingredients enumerated above, as required, followed by filtered sterilization. Generally, dispersions are prepared by incorporating a compound provided herein into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of a compound provided herein plus any additional desired ingredient from a previously sterile-filtered solution thereof.

Oral compositions generally include an inert diluent or an edible carrier. For the purpose of oral therapeutic administration, a compound provided herein can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the compounds provided herein can be formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

Additionally, intranasal delivery is possible, as described in, inter alfa, Hamajima et al., Clin. Immunol. Immunopathol., 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical composition may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Dosage forms or compositions containing a compound as described herein in the range of 0.005% to 100% with the balance made up from non-toxic carrier may be prepared. Methods for preparation of these compositions are known to those skilled in the art. The contemplated compositions may contain 0.001%-100% of a compound provided herein, in one embodiment 0.1-95%, in another embodiment 75-85%.

The pharmaceutical compositions can be included in a container, pack, or dispenser together with instructions for administration.

As described above, the preparations of one or more compounds provided herein may be given orally, parenterally, topically, or rectally. They are, of course, given by forms suitable for each administration route. For example, they are administered in tablets or capsule form, by injection, inhalation, eye lotion, ointment, suppository, infusion; topically by lotion or ointment; and rectally by suppositories. In some embodiments, administration is oral.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection, and infusion.

Actual dosage levels of the active ingredients in the pharmaceutical compositions provided herein may be varied so as to obtain an amount of the active ingredient which is effective to achieve the desired therapeutic response for a particular patient, composition, and mode of administration, without being toxic to the patient.

The concentration of a compound provided herein in a pharmaceutically acceptable mixture will vary depending on several factors, including the dosage of the compound to be administered, the pharmacokinetic characteristics of the compound(s) employed, and the route of administration. In some embodiments, the compositions provided herein can be provided in an aqueous solution containing about 0.1-10% w/v of a compound disclosed herein, among other substances, for parenteral administration. Typical dose ranges can include from about 0.01 to about 50 mg/kg of body weight per day, given in 1-4 divided doses. Each divided dose may contain the same or different compounds. The dosage will be a therapeutically effective amount depending on several factors including the overall health of a patient, and the formulation and route of administration of the selected compound(s).

Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses. The amount of active ingredient which can be combined with a carrier material to produce a single dosage form will generally be that amount of the compound which produces a therapeutic effect.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the patient and adjusting the dosage and/or timing.

Also provided herein is a conjoint therapy wherein one or more other therapeutic agents are administered with a compound or a pharmaceutical composition comprising a compound provided herein. Such conjoint treatment may be achieved by way of the simultaneous, sequential, or separate dosing of the individual components of the treatment.

Definitions

For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about", whether or not the term is explicitly used, unless explicitly stated otherwise. As used herein, the singular forms "a," "an," and "the" include plural referents unless the context clearly dictates otherwise.

A "subject," as used herein, includes both humans and other animals, particularly mammals. Thus, the methods are applicable to both human therapy and veterinary applications. In some embodiments, the patient is a mammal, for example, a primate. In some embodiments, the patient is a human.

A "therapeutically effective" amount of a compound provided herein is typically one which is sufficient to prevent, eliminate, ameliorate or reduce the symptoms of a HCMV infection. It will be appreciated that different concentrations may be employed for prophylaxis than for treatment of an active disease.

A "virus production inhibiting" amount of a compound provided herein is typically one which is sufficient to achieve a measurable reduction in the amount of virus produced by the cells contacted with the compound. In some embodiments, a "virus production inhibiting" amount is an amount which inhibits a least 30% of the virus production in untreated cells. In some embodiments, a "virus production inhibiting" amount is an amount which inhibits a least 50% of the virus production in untreated cells. In some embodiments, a "virus production inhibiting" amount is an amount which inhibits a least 70% of the virus production in untreated cells. In some embodiments, a "virus production inhibiting" amount is an amount which inhibits a least 90% of the virus production in untreated cells.

The terms "treatment" and "prevention" are art-recognized and include administration of one or more of the compounds or pharmaceutical compositions provided herein. If it is administered prior to clinical manifestation of the unwanted condition (e.g., disease or other unwanted state of the subject) then the treatment is preventative, (i.e., it protects the subject against developing the unwanted condition). As used in this context, the term "prevent" means to slow or prevent the onset of at least one symptom of a disorder as provided herein. For example, such prevention may be prompted by a likelihood of exposure to an infective agent (e.g., a virus) or when a subject exhibits other symptoms that indicate onset of a disorder (e.g., a metabolic disorder or cardiovascular disorder) may be likely. Alternatively, if it is administered after manifestation of the unwanted condition, the treatment is therapeutic, (i.e., it is intended to diminish, ameliorate, or stabilize the existing unwanted condition or side effects thereof). As used in this context, to "treat" means to ameliorate at least one symptom of a disorder as provided herein.

The term, "compound," as used herein is meant to include all stereoisomers, geometric isomers, and tautomers of the structures depicted. Compounds herein identified by name or structure as one particular tautomeric form are intended to include other tautomeric forms unless otherwise specified.

In some embodiments, a compound provided herein, or salt thereof, is substantially isolated. By "substantially isolated" it is meant that the compound is at least partially or substantially separated from the environment in which it was formed or detected. Partial separation can include, for example, a composition enriched in the compound provided herein. Substantial separation can include compositions containing at least about 50%, at least about 60%, at least about 70%, at least about 80%, at least about 90%, at least about 95%, at least about 97%, or at least about 99% by weight of the compound provided herein, or salt thereof. Methods for isolating compounds and their salts are routine in the art.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salt" refers to the relatively non-toxic, inorganic and organic acid addition salts of a compound provided herein. These salts can be prepared in situ during the final isolation and purification of a compound provided herein, or by separately reacting the compound in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", J. Pharm. Sci. 66: 1-19.)

In some embodiments, a compound provided herein may contain one or more acidic functional groups and, thus, is capable of forming pharmaceutically acceptable salts with pharmaceutically acceptable bases. The term "pharmaceutically acceptable salts" in these instances refers to the relatively non-toxic inorganic and organic base addition salts of a compound provided herein. These salts can likewise be prepared in situ during the final isolation and purification of the compound, or by separately reacting the purified compound in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

The term "alkyl" as employed herein refers to straight and branched chain aliphatic groups having from 1 to 12 carbon atoms, preferably 1-8 carbon atoms, and more preferably 1-6 carbon atoms, which is optionally substituted with one, two or three substituents. Preferred alkyl groups include, without limitation, methyl, ethyl, propyl, isopropyl, butyl, isobutyl, secbutyl, tertbutyl, pentyl, and hexyl. A "$C_0$" alkyl (as in "$C_0$-$C_3$-alkyl") is a covalent bond (like "$C_0$" hydrocarbyl). The term "lower alkyl" refers to straight and branched chain aliphatic groups having from 1 to 6 carbon atoms. Unless otherwise specified, the term "alkyl" includes alkenyl, alkynyl and cyclic alkyl groups.

The term "alkenyl" as used herein means an unsaturated straight or branched chain aliphatic group with one or more carbon-carbon double bonds, having from 2 to 12 carbon atoms, preferably 2-8 carbon atoms, and more preferably 2-6 carbon atoms, which is optionally substituted with one, two or three substituents. Preferred alkenyl groups include, without limitation, ethenyl, propenyl, butenyl, pentenyl, and hexenyl.

The term "alkynyl" as used herein means an unsaturated straight or branched chain aliphatic group with one or more carbon-carbon triple bonds, having from 2 to 12 carbon atoms, preferably 2-8 carbon atoms, and more preferably 2-6 carbon atoms, which is optionally substituted with one, two or three substituents. Preferred alkynyl groups include, without limitation, ethynyl, propynyl, butynyl, pentynyl, and hexynyl.

The term "heteroalkyl" refers to an alkyl group, as defined herein above, wherein one or more carbon atoms in the chain are replaced by a heteroatom selected from the group consisting of O, S, and N.

An "aryl" group is a $C_6$-$C_{14}$ aromatic moiety comprising one to three aromatic rings, which is optionally substituted. Preferably, the aryl group is a $C_6$-$C_{10}$ aryl group. Preferred aryl groups include, without limitation, phenyl, naphthyl, anthracenyl, and fluorenyl.

A "heterocyclyl" or "heterocyclic" group is a ring structure having from about 3 to about 8 atoms, wherein one or more atoms are selected from the group consisting of N, O, and S. The heterocyclic group is optionally substituted on carbon at one or more positions. The heterocyclic group is also independently optionally substituted on nitrogen with alkyl, aryl, aralkyl, alkylcarbonyl, alkyl sulfonyl, arylcarbonyl, aryl sulfonyl, alkoxycarbonyl, aralkoxycarbonyl, or on sulfur with oxo or lower alkyl. Preferred heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, and morpholino. In certain preferred embodiments, the heterocyclic group is fused to an aryl, heteroaryl, or cycloalkyl group. Examples of such fused heterocyles include, without limitation, tetrahydroquinoline and dihydrobenzofuran. Specifically excluded from the scope of this term are compounds having adjacent annular O and/or S atoms.

As used herein, the term "heteroaryl" refers to groups having 5 to 14 ring atoms, preferably 5, 6, 9, or 10 ring atoms; having 6, 10, or 14 π electrons shared in a cyclic array; and having, in addition to carbon atoms, from one to three heteroatoms per ring selected from the group consisting of N, O, and S. A "heteroaralkyl" or "heteroarylalkyl" group comprises a heteroaryl group covalently linked to an alkyl group, either of which is independently optionally substituted or unsubstituted. Preferred heteroalkyl groups comprise a C1-C6 alkyl group and a heteroaryl group having 5, 6, 9, or 10 ring atoms. Specifically excluded from the scope of this term are compounds having adjacent annular O and/or S atoms. Examples of preferred heteroaralkyl groups include pyridylmethyl, pyridylethyl, pyrrolylmethyl, pyrrolylethyl, imidazolylmethyl, imidazolylethyl, thiazolylmethyl, and thiazolylethyl. Specifically excluded from the scope of this term are compounds having adjacent annular O and/or S atoms.

Embodiments of heterocyclyls and heteroaryls include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

As employed herein, when a moiety (e.g., cycloalkyl, hydrocarbyl, aryl, heteroaryl, heterocyclic, urea, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—), nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups.

The term "halogen" or "halo" as employed herein refers to chlorine, bromine, fluorine, or iodine. As herein employed, the term "acyl" refers to an alkylcarbonyl or arylcarbonyl substituent. The term "acylamino" refers to an amide group attached at the nitrogen atom (i.e., R—CO—NH—). The term "carbamoyl" refers to an amide group attached at the carbonyl carbon atom (i.e., NH$_2$—CO—). The nitrogen atom of an acylamino or carbamoyl substituent is optionally additionally substituted. The term "sulfonamido" refers to a sulfonamide substituent attached by either the sulfur or the nitrogen atom. The term "amino" is meant to include NH$_2$, alkylamino, arylamino, and cyclic amino groups. The term "ureido" as employed herein refers to a substituted or unsubstituted urea moiety.

A moiety that is substituted is one in which one or more hydrogens have been independently replaced with another chemical substituent. As a non-limiting example, substituted phenyls include 2-flurophenyl, 3,4-dichlorophenyl, 3-chloro-4-fluoro-phenyl, 2-fluor-3-propylphenyl. As another non-limiting example, substituted n-octyls include 2,4 dimethyl-5-ethy-octyl and 3-cyclopentyl-octyl. Included within this definition are methylenes (—CH—) substituted with oxygen to form carbonyl-CO—).

An "unsubstituted" moiety as defined above (e.g., unsubstituted cycloalkyl, unsubstituted heteroaryl, etc.) means that moiety as defined above that does not have any of the optional substituents for which the definition of the moiety (above) otherwise provides. Thus, for example, while an "aryl" includes phenyl and phenyl substituted with a halo, "unsubstituted aryl" does not include phenyl substituted with a halo.

Synthesis of Compounds of the Invention

The compounds in the present invention (compounds of general Formula I) can be prepared using the general reaction scheme set out in the schemes below.

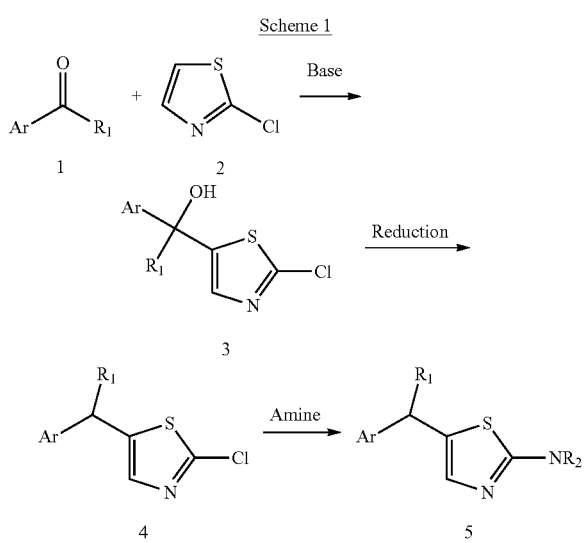

A suitable compound of general formula 1 where $R_1$ is H, a lower straight or branched alkyl or a suitable leaving group, e.g.,

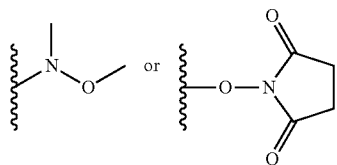

can be reacted with 2-chloro-1,3-thiazole and a base, e.g., n-BuLi or sec-BuLi to afford compounds of general structure 3. Compounds of general structure 3 can be treated with a suitable reducing agent, e.g., a silane such as triethylsilane and an acid such as trifluoroacetic acid to provide compounds of general structure 4. Compounds of general structure 4 can be treated with a suitable amine, e.g., benzylamine or 1,2,3,4-tetrahydroisoquinoline to afford compounds of general structure 5. It will be recognized that compounds of general structure 5 are identical to compounds of Formula I where $R_3$ is H.

Those skilled in the art will recognize there may be alternate synthetic paths to provide compounds of Formula I. The following Schemes describe non-limiting examples of such alternate synthetic paths.

Scheme 2

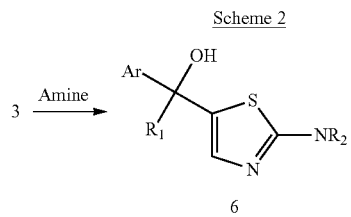

In some instances, compounds of general formula 3 can be treated with a suitable amine, e.g., benzylamine or 1,2,3,4-tetrahydroisoquinoline to afford compounds of general structure 6. Compounds of general structure 6 can be treated with a suitable reducing agent, e.g., a silane such as triethylsilane and an acid such as trifluoroacetic acid to provide compounds of general structure 5. It will be recognized that compounds of general structure 6 are identical to compounds of Formula I where $R_3$ is OH.

Scheme 3

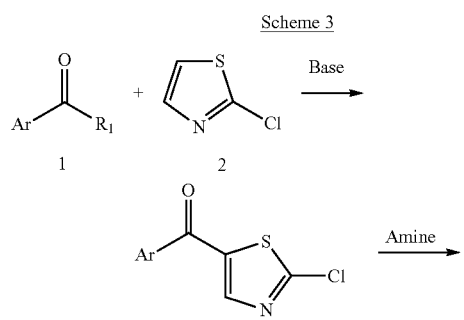

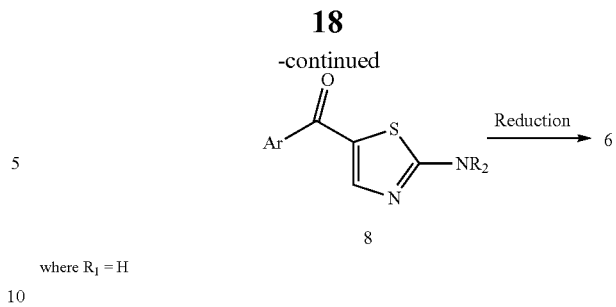

where $R_1 = H$

In some instances, where $R_1$ is a suitable leaving group as described above for Scheme 1, compounds of general formula 1 can be reacted with 2-chloro-1,3-thiazole and a base, e.g., n-BuLi or sec-BuLi to afford compounds of general structure 7. Compounds of general structure 7 can be treated with a suitable amine as described above for Schemes 1 and 2 to provide compounds of general structure 8. Compounds of general structure 8 can be treated with a suitable reducing agent, e.g., $NaBH_4$ or $LiAlH_4$ to afford compounds of general formula 6 where $R_1=H$. Compounds of general formula 6 can be treated as described above to provide compound of general formula 5.

Scheme 4

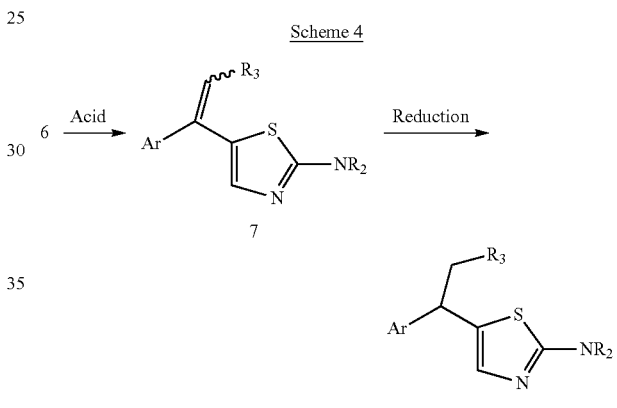

In some instances, compounds of general formula 6 can be treated with a suitable acid in the presence or absence of a co-reagent to provide compounds of general formula 7. Suitable acids can be organic, e.g., trifluoroacetic acid, or mineral, e.g., HCl or $H_2SO_4$. A co-reagent can be a silane, e.g., triethylsilane. Compound of general structure 7 can be reduced using suitable conditions, e.g., $H_2$ in the presence of a suitable catalyst, e.g., Pd/C or Pd(OH)$_2$/C. It will be recognized that compounds of general structure 7 are identical to compounds of Formula I where $R_2$ is alkenyl. It will be recognized that compounds of general structure 8 are identical to compounds of Formula I where $R_2$ is lower straight chain or branched alkyl.

Scheme 5

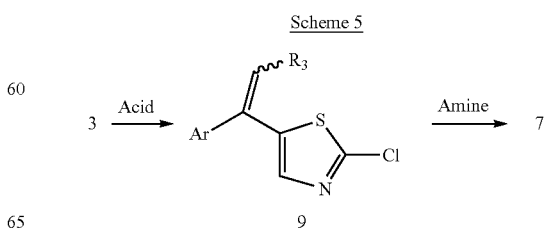

In some instances, compounds of general formula 3 can be treated with a suitable acid in the presence or absence of a co-reagent to afford compounds of general formula 9 as described above for the preparation of compounds of general structure 7 illustrated in Scheme 4. Compounds of general structure 9 can be treated with a suitable amine as described above for Schemes 1 and 2 to provide compounds of general structure 7; general structure 7 in Scheme 5 is identical to general structure 7 in Scheme 4.

Methods to perform the above described reactions and processes would be apparent to those of ordinary skill in the art based on the present disclosure, or can be deduced in analogy from the examples. Starting materials are commercially available or can be made by methods analogous to those described in the Examples below.

EXAMPLES

The invention is further described in the following examples, which do not limit the scope of the invention described in the claims.

Synthesis of Examples 1, 2 and 3

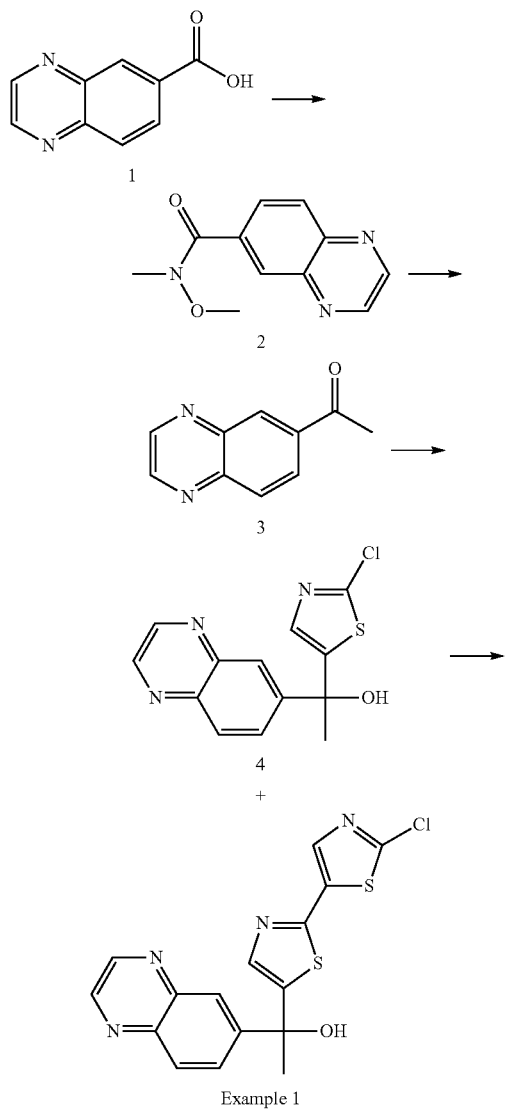

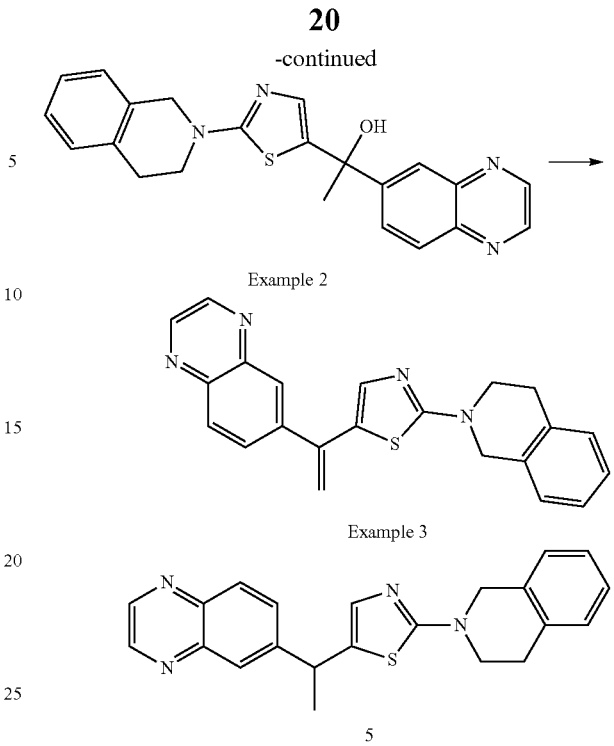

Procedure:
1. To a solution of Compound 1 (3 g, 17.2 mmol) in DCM (80 mL) were added N,O-dimethylhydroxylamine hydrochloride (2.0 g, 20.7 mmol), EDCI (4.0 g, 20.7 mmol), HOBt (2.3 g, 17.2 mmol) and DIEA (3.7 mL, 20.7 mmol). The resulting solution was stirred at room temperature (RT) overnight. The residue was treated with water and extracted with DCM. The organic extracts were washed with brine, dried over anhydrous $Na_2SO_4$, filtered and concentrated to give a crude oil. The crude product was purified by silica gel chromatography to afford Compound 2 (2.3 g, 61.5%).
2. To a solution of Compound 2 (1 g, 4.6 mmol) in dry THF (10 mL) at 0° C. under $N_2$ was added MeMgBr (2 mL, 3.0 mol/L, 6 mmol) dropwise. The resulting solution was slowly warm to RT over 2 hours. The mixture was diluted with $NH_4Cl$ solution and extracted with EA. The organic extracts were concentrated to give a crude oil. The crude product was purified by silica gel chromatography to afford Compound 3 (600 mg, 75.7%).
3. To a solution of 2-chlorothiazole (1 g, 8.4 mmol) in dry THF (10 mL) at −78° C. under $N_2$ was added n-BuLi (3.5 mL, 9.2 mmol) dropwise and the mixture stirred for 1 h. A solution of Compound 3 (1.3 g, 7.6 mmol) in dry THF (5 mL) was added dropwise to the reaction mixture at −78° C. The resulting solution was slowly warm to RT. The reaction was diluted with $NH_4Cl$ solution and extracted with EA. The organic extracts were concentrated to give a crude oil. The crude product was purified by silica gel chromatography to afford Example 1 (55 mg, 2%) and Compound 4 (1.6 g, 76.2%).

Example 1

$^1$HNMR ($CDCl_3$, 300 MHz) δ 2.0-2.2 (s, 3H), 4.1-4.2 (s, 1H), 7.3-7.4 (s, 1H), 7.8-7.9 (d, 1H), 8.0-8.1 (d, 1H), 8.2-8.3 (s, 1H), 8.8 (m, 1H), 9.0 (s, 1H), 9.3-9.4 (m, 1H).
LC-MS: m/z=375.1 $(M+1)^+$.

4. To a solution of Compound 4 (800 mg, 2.7 mmol) in DMF (5 mL) were added 1,2,3,4-tetrahydroisoquinoline (550 mg, 4.1 mmol)) and $K_2CO_3$ (570 mg, 4.1 mmol). The reaction mixture was stirred at 80° C. overnight. After cooling to RT, the residue was treated with water and extracted with EA. The organic extracts were washed with water, brine, dried over anhydrous $Na_2SO_4$, filtered and concentrated to give a crude oil. The crude product was purified by silica gel chromatography to afford Example 2 (250 mg, 23.41%).

LC-MS: m/z=389.2 (M+1)+.

5. To a solution of Example 2 (200 mg, 0.51 mmol) in DCE (10 mL) was added TES-H (180 mg, 1.5 mmol), the mixture cooled to 0° C. and TFA (590 mg, 5.1 mmol) was added dropwise. The resulting solution was stirred at 60° C. for 4 hours. The residue was concentrated and purified by silica gel chromatography to afford Compound 5 (5 mg, 2.6%) and Example 3 (10 mg, 7.1%).

Example 3

LC-MS: m/z=371.2 (M+1)+.
Compound 5: LC-MS: m/z=373.2 (M+1)+.

Synthesis of Examples 4-6

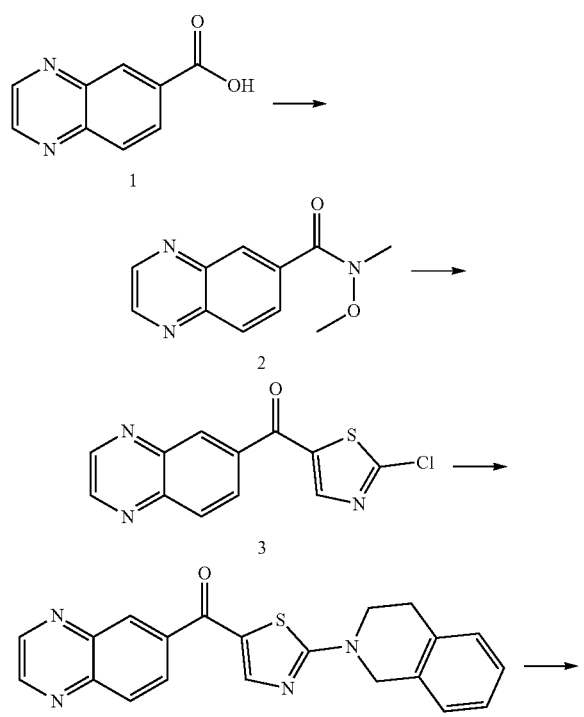

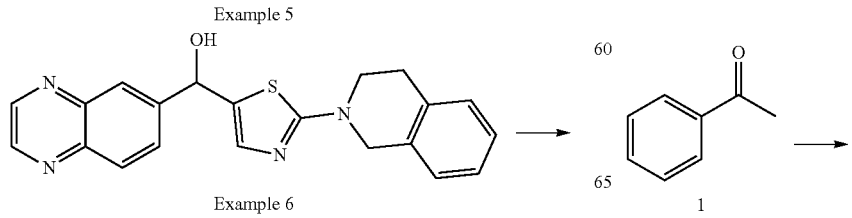

Example 6

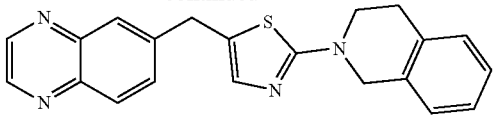

Example 4

Procedure:
1. A mixture of compound 1 (1.8 g, 10.3 mmol), DIEA (2.7 g, 20.7 mmol), N,O-dimethylhydroxylamine hydrochloride (1.2 g, 12.4 mmol), EDCI (2.4 g, 12.4 mmol) and HOBT (1.4 g, 10.3 mmol) in DCM was stirred at RT overnight, water was added and the mixture extracted with DCM. The combined extracts were concentrated and the residue purified by column chromatography to give 1.9 g of compound 2
2. To a solution of 2-chlorothiazole (485 mg, 4.05 mmol) in dry THF (10 mL) at −78° C. under $N_2$ was added n-BuLi (1.6 mL, 4.05 mmol) dropwise. After 1 hour a solution of Compound 2 (800 mg, 3.7 mmol) was added dropwise. The resulting solution was slowly warm to RT. The reaction was diluted with $NH_4Cl$ solution and extracted with EA. The organic extracts were concentrated to give a crude oil. The crude product was purified by silica gel chromatography to afford Compound 3 (500 mg)
3. To a solution of Compound 3 (200 mg, 0.73 mmol) in DMF (10 mL) were added 1,2,3,4-tetrahydroisoquinoline (145 mg, 1.09 mmol)) and $K_2CO_3$ (200 mg, 1.45 mmol). The reaction mixture was stirred at 80° C. overnight. After cooling to RT, the residue was treated with water and extracted with EA. The organic extracts were washed with water, brine, dried over anhydrous $Na_2SO_4$, filtered and concentrated to give a crude oil. The crude product was purified by silica gel chromatography to afford Example 6 (300 mg).
4. To a solution of Example 6 (200 mg, 0.538 mmol) in MeOH, $NaBH_4$ (50 mg, 1.23 mmol) was added at RT and the mixture stirred for 2 h. The mixture was diluted with water and extracted with EA. The extracts were dried over anhydrous $Na_2SO_4$, filtered and concentrated to give 150 mg of Example 5.
5. To a solution of Example 5 (150 mg, 0.4 mmol) in DCE (20 mL) was added TES-H (56 mg, 0.48 mmol), the mixture cooled to 0° C. and TFA (3.7 g, 32.8 mmol) was added dropwise at 0° C. The resulting solution was stirred at 60° C. for 4 hours. The residue was concentrated and purified by silica gel chromatography to afford Example 4 (80 mg).

$^1$HNMR (CDCl$_3$, 300 MHz) δ 1.6-1.7 (d, 2H), 3.0-3.1 (t, 2H), 3.7-3.8 (t, 2H), 4.2-4.3 (m, 1H), 4.6-4.7 (s, 2H), 6.4-6.5 (s, 1H), 7.0-7.1 (s, 1H), 7.2-7.4 (m, 4H), 7.4-7.5 (d, 2H), 7.6-7.8 (m, 3H), 7.9-8.0 (s, 1H).

LC-MS: m/z=359 (M+1)+.

Synthesis of Example 7

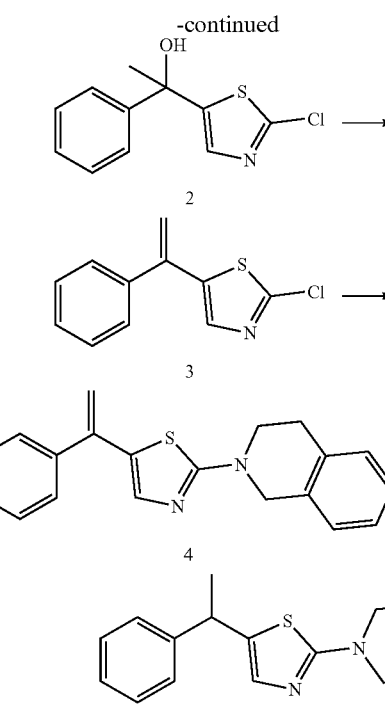

Example 7

Procedure:
1. To a solution of 2-chlorothiazole (2.2 g, 18.3 mmol) in dry THF (10 mL) was added n-BuLi (7.5 mL, 18.3 mmol) dropwise at −78° C. under $N_2$ and the mixture stirred for 1 h. A solution of Compound 1 (2 g, 16.7 mmol) was added dropwise at −78° C. The resulting solution was slowly warmed to RT. The reaction was diluted with $NH_4Cl$ solution and extracted with EA. The organic extracts were concentrated to give a crude oil. The crude product was purified by silica gel chromatography to afford Compound 2 (2 g).
2. To a solution of Compound 2 (1 g, 3.28 mmol) in DCE (20 mL) was added TES-H (1.1 g, 9.8 mmol), the mixture cooled to 0° C. and TFA (3.7 g, 32.8 mmol) was added dropwise. The resulting solution was stirred at 60° C. for 4 hours. The residue was concentrated and purified by silica gel chromatography to afford Compound 3 (800 mg).
3. To a solution of Compound 3 (400 mg, 1.4 mmol) in DMF (10 mL) were added 1,2,3,4-tetrahydroisoquinoline (280 mg, 2.1 mmol)) and $K_2CO_3$ (390 mg, 2.8 mmol). The reaction mixture was stirred at 80° C. overnight. After cooling to RT, the residue was treated with water and extracted with EA. The organic extracts were washed with water, brine, dried over anhydrous $Na_2SO_4$, filtered and concentrated to give a crude oil. The crude product was purified by silica gel chromatography to afford Compound 4 (150 mg).
4. To a solution of Compound 4 (150 mg, 0.4 mmol) in MeOH (10 mL) was added Pd/C (20 mg). The reaction mixture was stirred at RT under a $H_2$ balloon overnight. The residue was filtered, the filter cake washed with MeOH and the filtrate was concentrated and purified by silica gel chromatography to afford Example 7 (40 mg).
$^1$HNMR (CDCl$_3$, 300 MHz) δ 1.6-1.7 (d, 2H), 3.0-3.1 (t, 2H), 3.7-3.8 (t, 2H), 4.2-4.3 (m, 1H), 4.6-4.7 (s, 2H), 6.4-6.5 (s, 1H), 7.0-7.1 (s, 1H), 7.2-7.4 (m, 4H), 7.4-7.5 (d, 2H), 7.6-7.8 (m, 3H), 7.9-8.0 (s, 1H).
LC-MS: m/z=321 (M+1)+.

Synthesis of Example 8

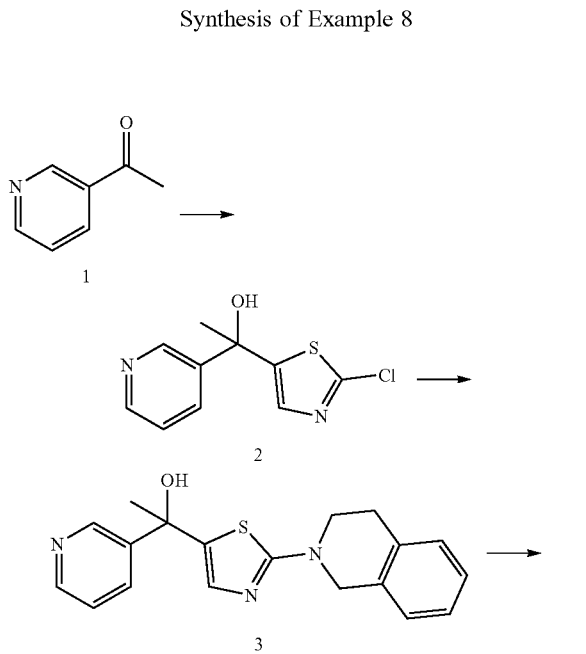

Example 8

Procedure:
1. To a solution of 2-chlorothiazole (4.8 g, 48 mmol) in dry THF (50 mL) was added n-BuLi (16 mL, 48 mmol) dropwise at −78° C. under $N_2$ and the mixture stirred for 1 h. A solution of Compound 1 (4 g, 44 mmol) was added dropwise at −78° C. The resulting solution was slowly warmed to RT. The reaction was diluted with $NH_4Cl$ solution and extracted with EA. The organic extracts were concentrated to give a crude oil. The crude product was purified by silica gel chromatography to afford Compound 2 (2.1 g).
2. To a solution of Compound 2 (2.4 g, 10 mmol) in DMF (10 mL) were added 1,2,3,4-tetrahydroisoquinoline (2.6 g, 20 mmol)) and $K_2CO_3$ (5.2 mg, 30 mmol). The reaction mixture was stirred at 80° C. overnight. After cooling to RT, the residue was treated with water and extracted with EA. The organic extracts were washed with water, brine, dried over anhydrous $Na_2SO_4$, filtered and concentrated to give a crude oil. The crude product was purified by silica gel chromatography to afford Compound 3 (800 mg).
3. To a solution of Compound 3 (0.8 g, 2.2 mmol) in DCE (20 mL) was added TES-H (1.22 g, 4.4 mmol), the mixture cooled to 0° C. and TFA (3 g, 22 mmol) was added dropwise at 0° C. The resulting solution was stirred at 60° C. for 4 hours. The residue was concentrated and purified by silica gel chromatography to afford Compound 4 (100 mg).
4. To a solution of Compound 4 (100 mg, 0.3 mmol) in MeOH (10 mL) was added Pd/C (10 mg). The reaction mixture was stirred at RTunder a H₂ balloon overnight. The residue was filtered, the filter cake was washed with MeOH and the filtrate was concentrated and purified by silica gel chromatography to afford Example 8 (36 mg).
¹HNMR (CDCl₃, 300 MHz) δ 1.6-1.7 (d, 3H), 2.9-3.0 (t, 2H) 3.7-3.8 (t, 2H), 4.2-4.3 (t, 1H), 4.6-4.7 (s, 2H), 6.9-7.0 (s, 1H), 7.1-7.3 (m, 4H), 7.4-7.5 (d, 1H), 8.5-8.6 (m, 2H). LC-MS: m/z=322 (M+1)+.

Synthesis of Example 9

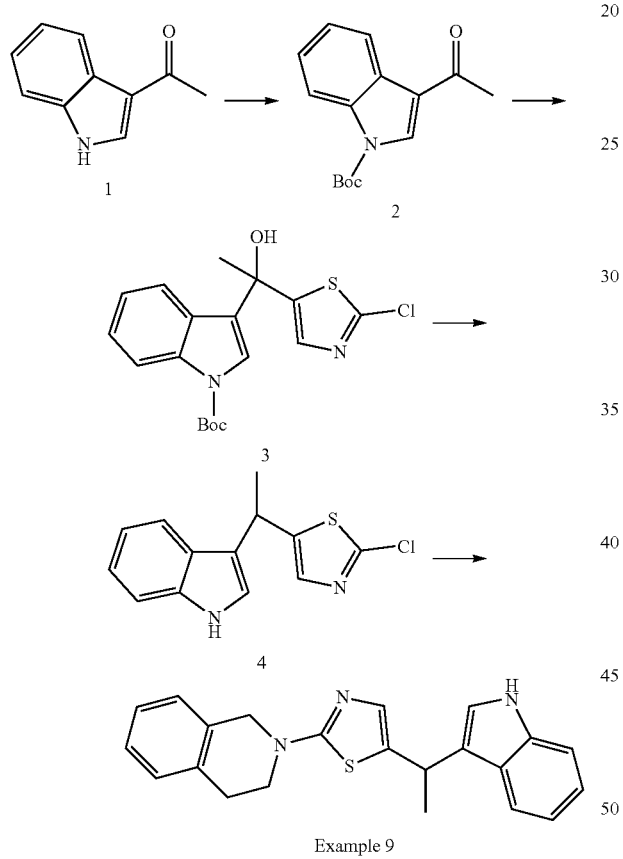

Example 9

Procedure:
1. To a solution of Compound 1 (8 g, 0.05 mmol) in DCM (100 mL) was added Boc₂O (12 g, 1.1 eq), DMAP (0.5 g 0.1 eq) was added and the mixture was stirred at RT for 2 hours. Water was added and the solution was extracted with DCM. The organic extracts were washed with brine, dried over Na₂SO₄, concentrated and the residue purified by preparative chromatography to give 12 g product of Compound 2.
2. To a solution of 2-chlorothiazole (1.6 g, 12 mmol) in dry THF (30 mL) was added n-BuLi (5.2 mL, 12 mmol) dropwise at −78° C. under N₂ and the mixture stirred for 1 h. A solution of Compound 2 (3 g, 11 mmol) was added dropwise at −78° C. The resulting solution slowly warmed to RT. The reaction was diluted with NH₄Cl solution and extracted with EA. The organic extracts were concentrated to give a crude oil. The crude product was purified by silica gel chromatography to afford Compound 3 (1.5 g).
3. To a solution of Compound 3 (2 g, 4.3 mmol) in DCE (20 mL) was added TES-H (1.22 g, 8.6 mmol), the mixture cooled to 0° C. and TFA (6.5 g, 43 mmol) was added dropwise at 0° C. The resulting solution was stirred at 60 C for 4 hours. The residue was concentrated and purified by silica gel chromatography to afford Compound 4 (400 mg).
4. To a solution of Compound 4 (400 mg, 1.2 mmol) in DMF (10 mL) were added 1,2,3,4-tetrahydroisoquinoline (250 mg, 2.1 mmol)) and K₂CO₃ (500 mg, 3.4 mmol). The reaction mixture was stirred at 80° C. overnight. After cooling to RT, the residue was treated with water and extracted with EA. The organic extracts were washed with water, brine, dried over anhydrous Na₂SO₄, filtered and concentrated to give a crude oil. The crude product was purified by silica gel chromatography to afford Example 9 (50 mg).
¹HNMR (CDCl₃, 300 MHz) δ 1.6-1.7 (d, 3H), 2.9-3.0 (t, 2H), 3.6-3.7 (t, 2H), 4.4-4.5 (m, 3H), 7.0-7.1 (s, 1H), 7.1-7.3 (m, 9H), 7.3-7.4 (d, 1H), 7.6-7.8 (d, 1H), 7.9-8.0 (s, 1H). LC-MS: m/z=360 (M+1)+.

Synthesis of Example 10

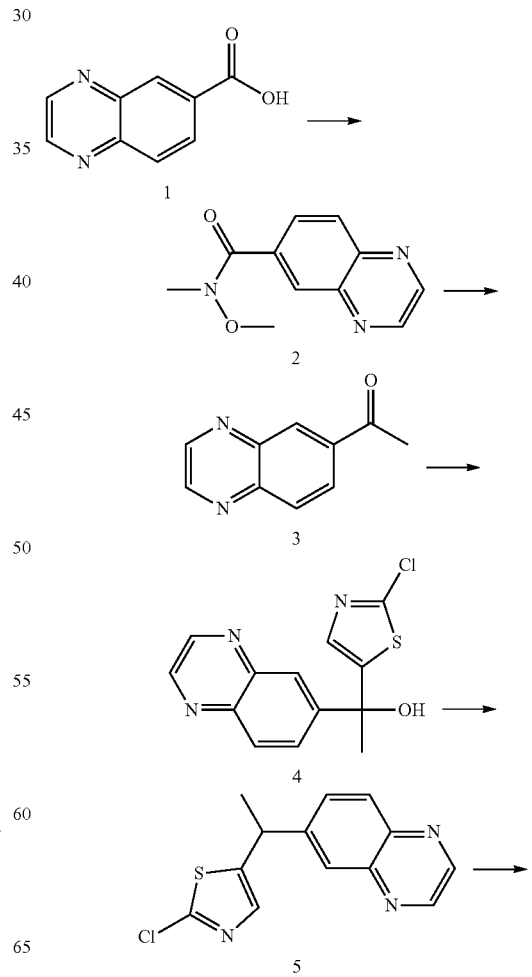

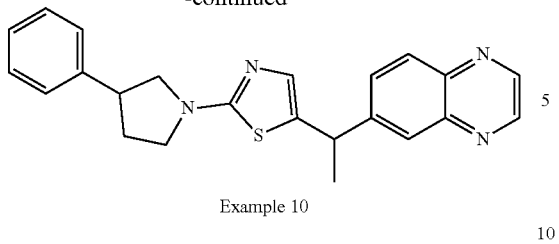

Example 10

Procedure:
1. To a solution of Compound 1 (3 g, 17.2 mmol) in DCM (80 mL) were added N,O-dimethylhydroxylamine hydrochloride (2.0 g, 20.7 mmol), EDCI (4.0 g, 20.7 mmol), HOBt (2.3 g, 17.2 mmol) and DIEA (3.7 mL, 20.7 mmol). The resulting solution was stirred at RT overnight. The residue was treated with water and extracted with DCM. The organic extracts were washed with brine, dried over anhydrous $Na_2SO_4$, filtered and concentrated to give a crude oil. The crude product was purified by silica gel chromatography to afford Compound 2 (2.3 g, 61.5%).
2. To a solution of Compound 2 (1 g, 4.6 mmol) in dry THF (10 mL) at 0° C. under $N_2$ was added MeMgBr (2 mL, 3.0 mol/L, 6 mmol) dropwise. The resulting solution was slowly warmed to RT over 2 hours. The reaction was diluted with $NH_4Cl$ solution and extracted with EA. The organic extracts were concentrated to give a crude oil. The crude product was purified by silica gel chromatography to afford Compound 3 (600 mg, 75.7%).
3. To a solution of 2-chlorothiazole (1 g, 8.4 mmol) in dry THF (10 mL) was added n-BuLi (3.5 mL, 9.2 mmol) dropwise at −78° C. under $N_2$ and the mixture stirred for 1 h. A solution of Compound 3 (1.3 g, 7.6 mmol) in dry THF (5 mL) was added dropwise at −78° C. The resulting solution was slowly warmed to RT. The reaction was diluted with $NH_4Cl$ solution and extracted with EA. The organic extracts were concentrated to give a crude oil. The crude product was purified by silica gel chromatography to afford Compound 4 (1.6 g, 72.6%).
$^1$HNMR (CDCl$_3$, 300 MHz) δ 2.0-2.1 (s, 3H), 4.1-4.2 (s, 1H), 7.3-7.4 (s, 1H), 7.8-7.9 (d, 1H), 8.0-8.1 (d, 1H), 8.3 (s, 1H), 8.8 (s, 2H).
4. To a solution of Compound 4 (1.2 g, 4.1 mmol) in DCE (30 mL) was added TES-H (1.4 mg, 12.3 mmol), the mixture cooled to 0° C. and Then TFA (4.7 mg, 41 mmol) was added dropwise. The resulting solution was stirred at 60° C. for 4 hours. The residue was concentrated and purified by silica gel chromatography to afford Compound 5 (0.6 g, 52.8%).
5. To a solution of Compound 5 (200 mg, 0.74 mmol) in DMF (5 mL) were added 3-phenylpyrrolidine (160 mg, 1.1 mmol)) and $K_2CO_3$ (200 mg, 1.48 mmol). The reaction mixture was stirred at 80° C. overnight. After cooling to RT, the residue was treated with water and extracted with EA. The organic extracts were washed with water, brine, dried over anhydrous $Na_2SO_4$, filtered and concentrated to give a crude oil. The crude product was purified by silica gel chromatography to afford Example 10 (50 mg, 17.8%).
$^1$HNMR (CDCl$_3$, 300 MHz) δ 1.5-1.7 (s, 4H), 2.3 (m, 1H), 2.5-2.6 (m, 1H), 3.6-3.7 (m, 3H), 3.9 (m, 1H), 4.0-4.1 (m, 1H), 7.2-7.4 (m, 5H), 7.9 (s, 1H), 8.1-8.3 (m, 2H), 8.5-8.6 (s, 1H), 8.9-9.0 (s, 2H).
LC-MS: m/z=387.2 (M+1)$^+$.

Synthesis of Example 11

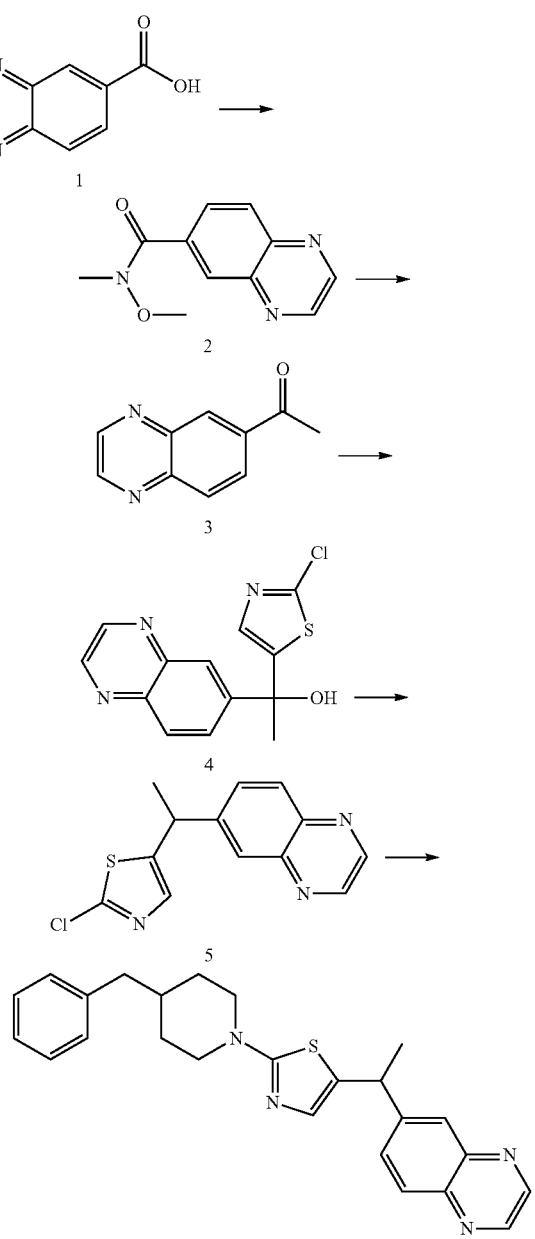

Example 11

Procedure:
1. To a solution of Compound 1 (3 g, 17.2 mmol) in DCM (80 mL) were added N,O-dimethylhydroxylamine hydrochloride (2.0 g, 20.7 mmol), EDCI (4.0 g, 20.7 mmol), HOBt (2.3 g, 17.2 mmol) and DIEA (3.7 mL, 20.7 mmol). The resulting solution was stirred at RT overnight. The residue was treated with water and extracted with DCM. The organic extracts were washed with brine, dried over anhydrous $Na_2SO_4$, filtered and concentrated to give a crude oil. The crude product was purified by silica gel chromatography to afford Compound 2 (2.3 g, 61.5%).
2. To a solution of Compound 2 (1 g, 4.6 mmol) in dry THF (10 mL) at 0° C. under $N_2$ was added MeMgBr (2 mL, 3.0 mol/L, 6 mmol) dropwise. The resulting solution was slowly warmed to RT over 2 hours. The reaction was diluted with NH₄Cl solution and extracted with EA. The organic extracts were concentrated to give a crude oil. The crude product was purified by silica gel chromatography to afford Compound 3 (600 mg, 75.7%).

3. To a solution of 2-chlorothiazole (1 g, 8.4 mmol) in dry THF (10 mL) at −78° C. under N₂ was added n-BuLi (3.5 mL, 9.2 mmol) dropwise. After 1 hour a solution of Compound 3 (1.3 g, 7.6 mmol) in dry THF (5 mL) was added dropwise at −78° C. The resulting solution was slowly warmed to RT. The reaction was diluted with NH₄Cl solution and extracted with EA. The organic extracts were concentrated to give a crude oil. The crude product was purified by silica gel chromatography to afford Compound 4 (1.6 g, 72.6%).

¹HNMR (CDCl₃, 300 MHz) δ 2.0-2.1 (s, 3H), 4.1-4.2 (s, 1H), 7.3-7.4 (s, 1H), 7.8-7.9 (d, 1H), 8.0-8.1 (d, 1H), 8.3 (s, 1H), 8.8 (s, 2H).

4. To a solution of Compound 4 (1.2 g, 4.1 mmol) in DCE (30 mL) was added TES-H (1.4 mg, 12.3 mmol). Then TFA (4.7 mg, 41 mmol) was added dropwise at 0° C. The resulting solution was stirred at 60° C. for 4 hours. The residue was concentrated and purified by silica gel chromatography to afford Compound 5 (0.6 g, 52.8%).

5. To a solution of Compound 5 (600 mg, 2.2 mmol) in DMF (5 mL) were added 4-benzylpiperidine (570 mg, 3.3 mmol)) and K₂CO₃ (600 mg, 4.4 mmol). The reaction mixture was stirred at 80° C. overnight. After cooling to RT, the residue was treated with water and extracted with EA. The organic extracts were washed with water, brine, dried over anhydrous Na₂SO₄, filtered and concentrated to give a crude oil. The crude product was purified by silica gel chromatography to afford Example 11 (50 mg, 5.5%).

¹HNMR (CDCl₃, 300 MHz) δ 1.4-1.5 (m, 2H), 1.6-1.7 (s, 5H), 1.8-2.0 (m, 2H), 2.6-2.7 (d, 2H), 3.1-3.2 (t, 2H), 4.2-4.3 (t, 2H), 7.2-7.4 (m, 5H), 7.8-7.9 (s, 1H), 8.2-8.3 (m, 2H), 8.5-8.6 (s, 1H), 9.0 (s, 2H).

LC-MS: m/z=415 (M+1)⁺.

Synthesis of Example 12

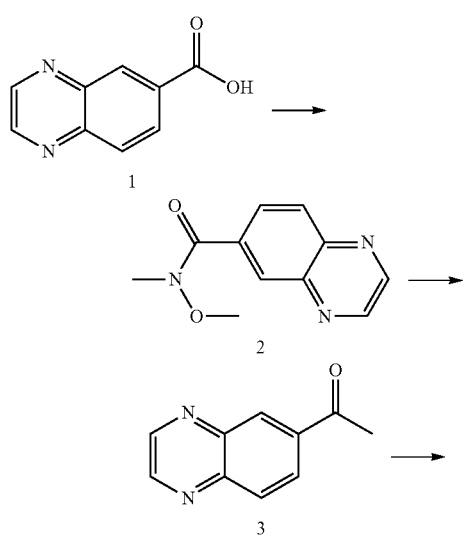

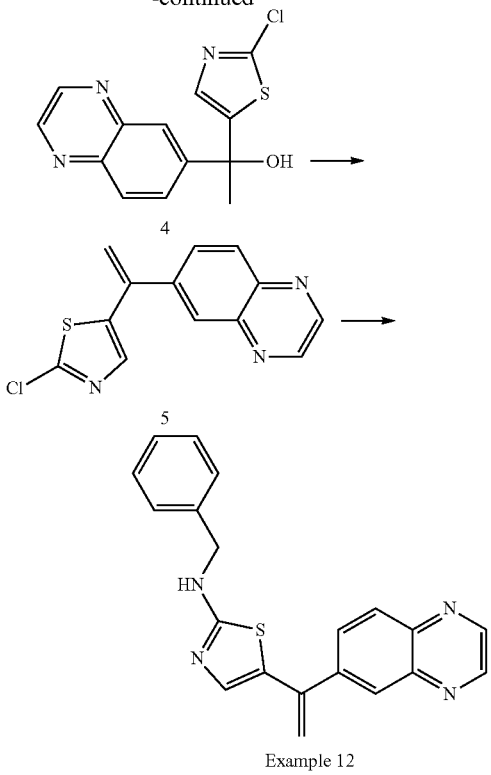

Example 12

Procedure:

1. To a solution of Compound 1 (3 g, 17.2 mmol) in DCM (80 mL) were added N,O-dimethylhydroxylamine hydrochloride (2.0 g, 20.7 mmol), EDCI (4.0 g, 20.7 mmol), HOBt (2.3 g, 17.2 mmol) and DIEA (3.7 mL, 20.7 mmol). The resulting solution was stirred at RT overnight. The residue was treated with water and extracted with DCM. The organic extracts were washed with brine, dried over anhydrous Na₂SO₄, filtered and concentrated to give a crude oil. The crude product was purified by silica gel chromatography to afford Compound 2 (2.3 g, 61.5%).

2. To a solution of Compound 2 (1 g, 4.6 mmol) in dry THF (10 mL) at 0° C. under N₂ was added MeMgBr (2 mL, 3.0 mol/L, 6 mmol) dropwise. The resulting solution was slowly warmed to RT over 2 hours. The reaction was diluted with NH₄Cl solution and extracted with EA. The organic extracts were concentrated to give a crude oil. The crude product was purified by silica gel chromatography to afford Compound 3 (600 mg, 75.7%).

3. To a solution of 2-chlorothiazole (1 g, 8.4 mmol) in dry THF (10 mL) at −78° C. under N₂ was added n-BuLi (3.5 mL, 9.2 mmol) dropwise. After 1 hour stirring at this tempa solution of Compound 3 (1.3 g, 7.6 mmol) in dry THF (5 mL) was added dropwise at −78° C. The resulting solution was slowly warmed to RT. The reaction was diluted with NH₄Cl solution and extracted with EA. The organic extracts were concentrated to give a crude oil. The crude product was purified by silica gel chromatography to afford Compound 4 (1.6 g, 72.6%).

¹HNMR (CDCl₃, 300 MHz) δ 2.0-2.1 (s, 3H), 4.1-4.2 (s, 1H), 7.3-7.4 (s, 1H), 7.8-7.9 (d, 1H), 8.0-8.1 (d, 1H), 8.3 (s, 1H), 8.8 (s, 2H).

4. To a solution of Compound 4 (1.2 g, 4.1 mmol) in DCE (30 mL) was added TES-H (1.4 mg, 12.3 mmol), the mixture cooled to 0° C. and TFA (4.7 mg, 41 mmol) was added dropwise. The resulting solution was stirred at 60° C. for 4 hours. The residue was concentrated and purified by silica gel chromatography to afford Compound 5 (0.6 g, 52.8%).

5. To a solution of Compound 5 (300 mg, 1.1 mmol) in DMF (5 mL) were added benzylamine (188 mg, 2.2 mmol)) and K$_2$CO$_3$ (300 mg, 2.2 mmol). The reaction mixture was stirred at 80° C. overnight. After cooling to RT, the residue was treated with water and extracted with EA. The organic extracts were washed with water, brine, dried over anhydrous Na$_2$SO$_4$, filtered and concentrated to give a crude oil. The crude product was purified by silica gel chromatography to afford Example 12 (20 mg, 5.3%).

$^1$HNMR (CDCl$_3$, 300 MHz) δ 4.4-4.5 (t, 2H), 5.5-5.2 (t, 1H), 6.9 (s, 1H), 7.5-7.2 (m, 5H), 7.8-7.9 (d, 1H), 8.2-8.1 (d, 1H), 8.3-8.2 (s, 1H), 9.0-8.9 (m, 1H).

LC-MS: m/z=345.2 (M+1)$^+$.

Synthesis of Examples 13 and 14

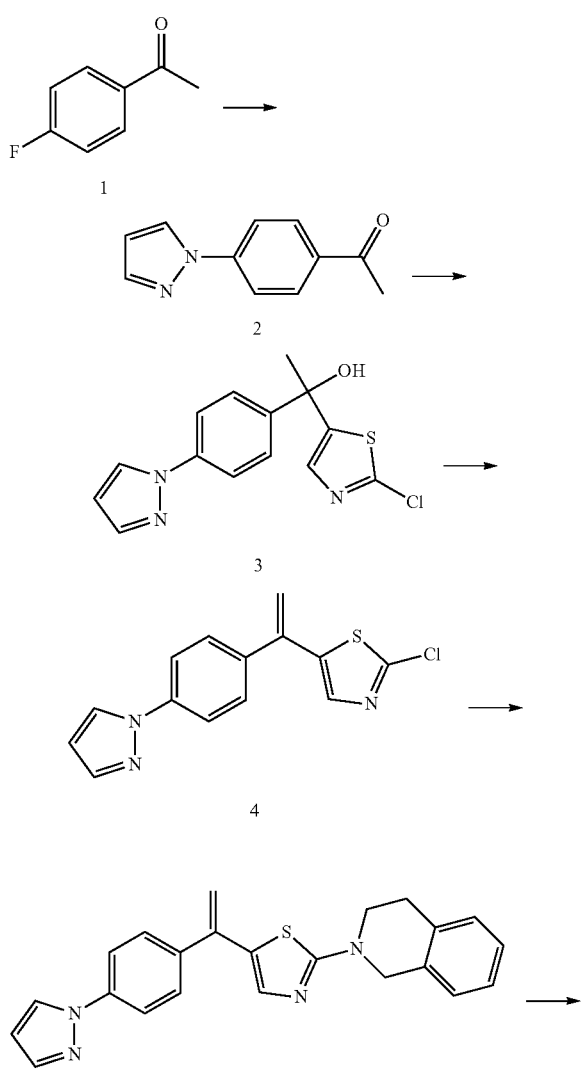

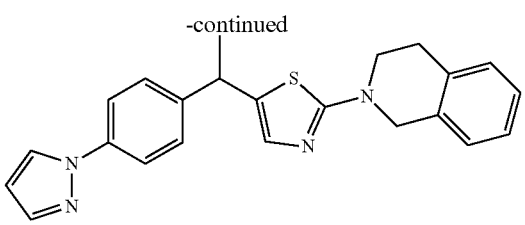

Example 13

Procedure:

1. To a solution of Compound 1 (10 g, 72.5 mmol) in dry DMF (100 mL) were added pyrazole (10 g, 145 mmol), K$_2$CO$_3$ (20 g, 145 mmol) and 18-crown-6 (2 g). The resulting solution was stirred at 130° C. for 4 hours. After cooling to RT, the residue was treated with water and extracted with EA. The organic extracts were washed with water, brine, dried over anhydrous Na$_2$SO$_4$, filtered and concentrated to give a crude oil. The crude product was purified by recrystallization to afford Compound 2 (3.5 g, 26%).

$^1$HNMR (CDCl$_3$, 300 MHz) δ 2.6-2.7 (s, 3H), 6.4-6.5 (s, 1H), 7.7-7.9 (m, 3H), 8.0-8.2 (m, 3H).

2. To a solution of 2-chlorothiazole (850 mg, 7 mmol) in dry THF (10 mL) at −78° C. under N$_2$ was added n-BuLi (2.8 mL, 7 mmol) dropwise. After 1 hour a solution of Compound 2 (1 g, 5.3 mmol) was added dropwise at −78° C. The resulting solution was slowly warmed to RT. The reaction was diluted with NH$_4$Cl solution and extracted with EA. The organic extracts were concentrated to give a crude oil. The crude product was purified by silica gel chromatography to afford Compound 3 (600 mg, 37%).

$^1$HNMR (CDCl$_3$, 300 MHz) δ 2.0-2.1 (s, 3H), 6.4-6.5 (s, 1H), 7.2-7.3 (s, 1H), 7.5-7.6 (d, 2H), 7.6-7.7 (d, 2H), 7.7-7.8 (s, 1H), 7.9-8.0 (s, 1H).

3. To a solution of Compound 3 (1 g, 3.28 mmol) in DCE (20 mL) was added TES-H (1.1 g, 9.8 mmol), the mixture cooled to 0° C. and TFA (3.7 g, 32.8 mmol) was added dropwise. The resulting solution was stirred at 60° C. for 4 hours. The residue was concentrated and purified by silica gel chromatography to afford Compound 4 (800 mg, 85%).

$^1$HNMR (CDCl$_3$, 300 MHz) δ 5.4-5.6 (ss, 2H), 6.4-6.5 (s, 1H), 7.2-7.4 (m, 2H), 7.4-7.5 (d, 2H), 7.6-7.8 (m, 3H), 7.9-8.0 (s, 1H).

4. To a solution of Compound 4 (400 mg, 1.4 mmol) in DMF (10 mL) were added 1,2,3,4-tetrahydroisoquinoline (280 mg, 2.1 mmol)) and K$_2$CO$_3$ (390 mg, 2.8 mmol). The reaction mixture was stirred at 80° C. overnight. After cooling to RT, the residue was treated with water and extracted with EA. The organic extracts were washed with water, brine, dried over anhydrous Na$_2$SO$_4$, filtered and concentrated to give a crude oil. The crude product was purified by silica gel chromatography to afford Example 14 (150 mg, 22.3%).

$^1$HNMR (CDCl$_3$, 300 MHz) δ 3.0-3.1 (t, 2H), 3.7-3.8 (t, 2H), 4.6-4.7 (s, 2H), 5.1-5.3 (ss, 2H), 6.4-6.5 (s, 1H), 7.0-7.1 (s, 1H), 7.2-7.4 (m, 4H), 7.5-7.6 (d, 2H), 7.6-7.8 (m, 3H), 7.9-8.0 (s, 1H).

LC-MS: m/z=385.2 (M+1)+.

5. To a solution of Example 14 (150 mg, 0.4 mmol) in MeOH (10 mL) was added Pd/C (20 mg). The reaction mixture was stirred at RT under a H$_2$ balloon overnight. The residue was filtered, the filter cake washed with MeOH, the filtrate was concentrated and purified by silica gel chromatography to afford Example 13 (40 mg, 27%).
¹HNMR CDCl₃, 300 MHz) δ 1.6-1.7 (d, 2H), 3.0-3.1 (t, 2H), 3.7-3.8 (t, 2H), 4.2-4.3 (m, 1H), 4.6-4.7 (s, 2H), 6.4-6.5 (s, 1H), 7.0-7.1 (s, 1H), 7.2-7.4 (m, 4H), 7.4-7.5 (d, 2H), 7.6-7.8 (m, 3H), 7.9-8.0 (s, 1H).
LC-MS: m/z=387.2 (M+1)+.

Synthesis of Example 15

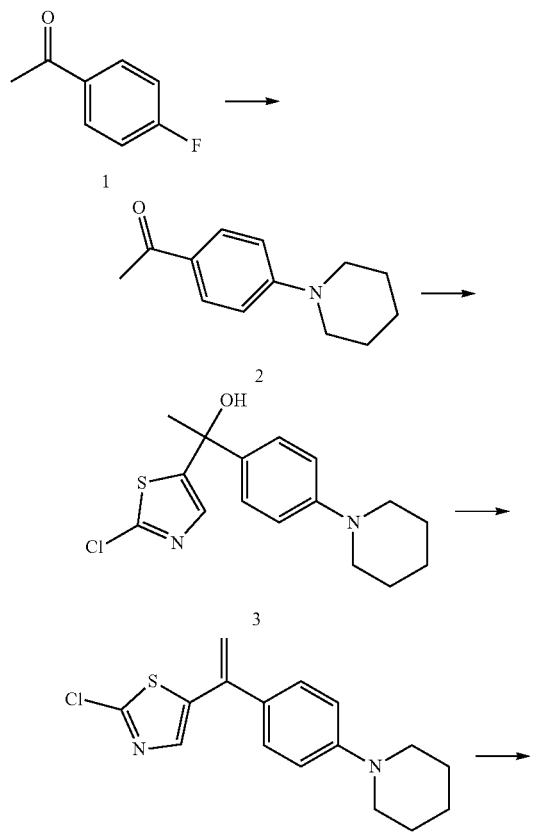

Example 15

Procedure:
1. To a solution of Compound 1 (10 g, 72.5 mmol) in dry DMF (100 mL) were added piperidine (12.6 g, 145 mmol), K₂CO₃ (20 g, 145 mmol) and 18-crown-6 (2 g). The resulting solution was stirred at 130° C. for 4 hours. After cooling to RT, the residue was treated with water and extracted with EA. The organic extracts were washed with water, brine, dried over anhydrous Na₂SO₄, filtered and concentrated to give a crude oil. The crude product was purified by recrystallization to afford Compound 2 (5 g, 34%).
2. To a solution of 2-chlorothiazole (3.5 g, 29.5 mmol) in dry THF (10 mL) at −78° C. under N₂ was added n-BuLi (12 mL, 29.5 mmol) dropwise. After 1 hour a solution of Compound 2 (5 g, 24.6 mmol) was added dropwise. The resulting solution was slowly warmed to RT. The reaction was diluted with NH₄Cl solution and extracted with EA. The organic extracts were concentrated to give a crude oil. The crude product was purified by silica gel chromatography to afford Compound 3 (2.9 g, 36.5%).
3. To a solution of Compound 3 (1 g, 3.1 mmol) in DCE (20 mL) was added TES-H (1.1 g, 9.3 mmol), the mixture cooled to 0° C. and TFA (3.5 g, 31 mmol) was added dropwise. The resulting solution was stirred at 60° C. for 4 hours. The residue was concentrated and purified by silica gel chromatography to afford Compound 4 (600 mg, 63.6%).
4. To a solution of Compound 4 (500 mg, 1.6 mmol) in DMF (10 mL) were added 1,2,3,4-tetrahydroisoquinoline (330 mg, 2.5 mmol)) and K₂CO₃ (500 mg, 3.2 mmol). The reaction mixture was stirred at 80° C. overnight. After cooling to RT, the residue was treated with water and extracted with EA. The organic extracts were washed with water, brine, dried over anhydrous Na₂SO₄, filtered and concentrated to give a crude oil. The crude product was purified by silica gel chromatography to afford Compound 5 (150 mg, 22.8%).
5. To a solution of Compound 5 (150 mg, 0.37 mmol) in MeOH (10 mL) was added Pd/C (20 mg). The reaction mixture was stirred at RT under a H₂ balloon overnight. The residue was filtered, the filter cake washed with MeOH, the filtrate was concentrated and purified by silica gel chromatography to afford Example 15 (62 mg, 41%).
¹HNMR CDCl₃, 300 MHz) δ 1.6-1.7 (m, 7H), 2.9-3.0 (m, 2H), 3.0-3.1 (m, 4H), 3.6-3.7 (m, 2H), 4.0-4.1 (m, 1H), 4.6 (s, 1H), 6.9 (m, 3H), 7.1-7.2 (m, 6H). LC-MS: m/z=404.2 (M+1)+.

Synthesis of Example 16

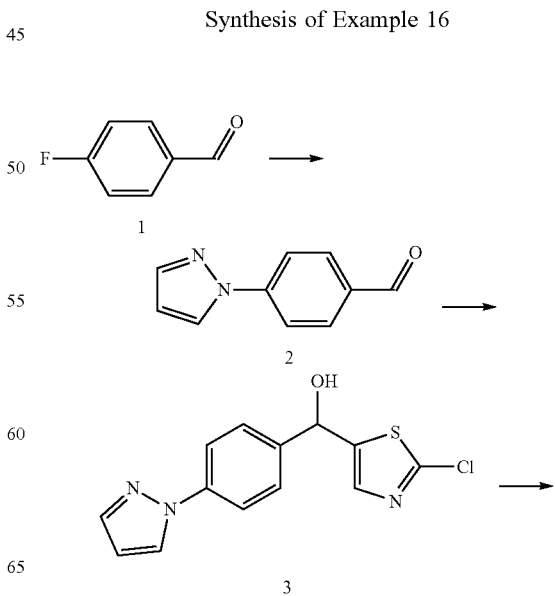

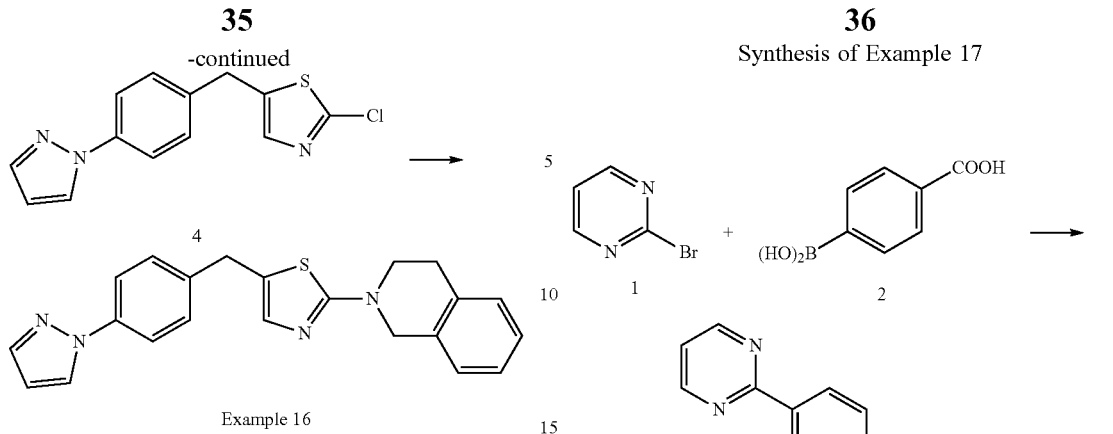

Example 16

Synthesis of Example 17

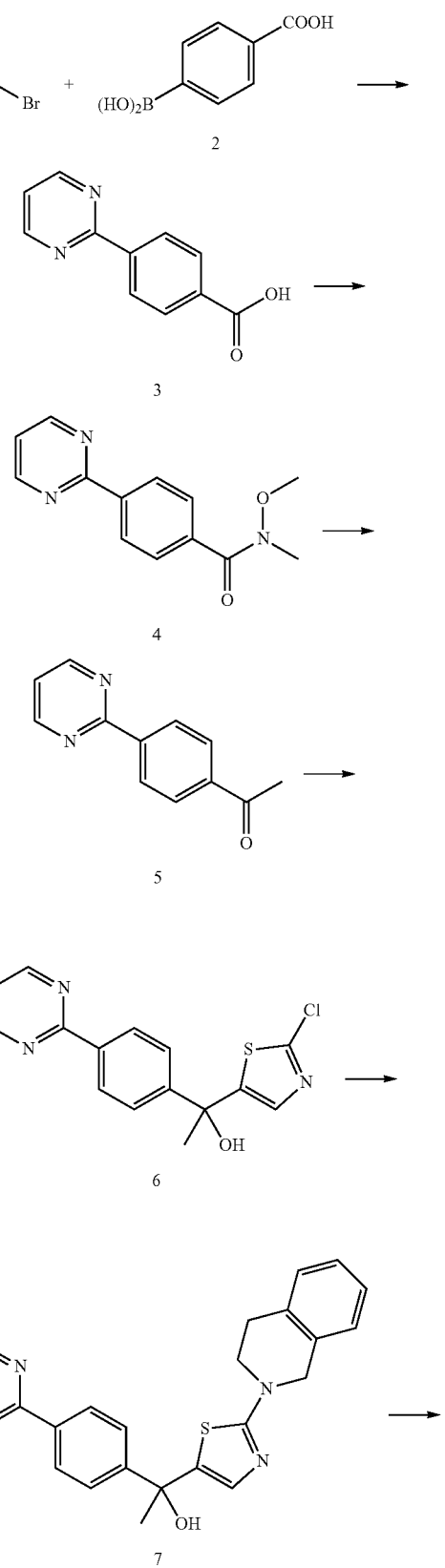

Procedure:
1. To a solution of Compound 1 (10 g, 80.6 mmol) in dry DMF (100 mL) were added pyrazole (5.5 g, 80.6 mmol) and K$_2$CO$_3$ (12.2 g, 88.7 mmol). The resulting solution was stirred at 100° C. for overnight. After cooling to RT, the residue was treated with water and extracted with EA. The organic extracts were washed with water, brine, dried over anhydrous Na$_2$SO$_4$, filtered and concentrated to give a crude oil. The crude product was purified by recrystallization to afford Compound 2 (4 g, 29%).
¹HNMR CDCl$_3$, 300 MHz) δ 6.5-6.6 (s, 1H), 7.7-7.8 (s, 1H), 7.9-8.0 (d, 2H), 8.0-8.1 (d, 2H), 8.1-8.2 (s, 1H), 10.0-10.1 (s, 1H).

2. To a solution of 2-chlorothiazole (1.45 g, 12.1 mmol) in dry THF (10 mL) at −78° C. under N$_2$ was added n-BuLi (5 mL, 12.1 mmol) dropwise. After 1 hour a solution of Compound 2 (1.6 g, 9.3 mmol) was added dropwise at −78° C. The resulting solution was slowly warmed to RT. The reaction was diluted with NH$_4$Cl solution and extracted with EA. The organic extracts were concentrated to give a crude oil. The crude product was purified by silica gel chromatography to afford Compound 3 (1.2 g, 50%).
¹HNMR CDCl$_3$, 300 MHz) δ 6.1-6.2 (s, 1H), 6.5-6.6 (s, 1H), 7.2-7.3 (s, 1H), 7.4-7.5 (d, 2H), 7.6-7.7 (d, 2H), 7.7-7.8 (s, 1H), 7.9-8.0 (s, 1H).

3. To a solution of Compound 3 (1.2 g, 4.1 mmol) in DCE (20 mL) was added TES-H (1.4 g, 12.8 mmol), the mixture cooled to 0° C. and TFA (4.7 g, 41 mmol) was added dropwise. The resulting solution was stirred at 60° C. for 4 hours. The residue was concentrated and purified by silica gel chromatography to afford Compound 4 (1 g, 91%).
¹HNMR (CDCl$_3$, 300 MHz) δ 4.1-4.2 (s, 2H), 6.4-6.5 (s, 1H), 7.2-7.4 (m, 3H), 7.6-7.8 (m, 3H), 7.9-8.0 (s, 1H).

4. To a solution of Compound 4 (500 mg, 1.8 mmol) in DMF (10 mL) were added 1,2,3,4-tetrahydroisoquinoline (362 mg, 2.7 mmol)) and K$_2$CO$_3$ (500 mg, 3.6 mmol). The reaction mixture was stirred at 80° C. overnight. After cooling to RT, the residue was treated with water and extracted with EA. The organic extracts were washed with water, brine, dried over anhydrous Na$_2$SO$_4$, filtered and concentrated to give a crude oil. The crude product was purified by silica gel chromatography to afford Example 16 (50 mg, 7.4%).
¹HNMR (CDCl$_3$, 300 MHz) δ 3.0-3.1 (t, 2H), 3.7-3.8 (t, 2H), 4.0-4.1 (s, 2H), 4.6-4.7 (s, 2H), 6.4-6.5 (s, 1H), 7.0-7.1 (s, 1H), 7.1-7.3 (m, 4H), 7.3-7.4 (d, 2H), 7.6-7.7 (d, 2H), 7.7-7.8 (s, 1H), 7.9-8.0 (s, 1H). LC-MS: m/z=373.3 (M+1)+.

-continued

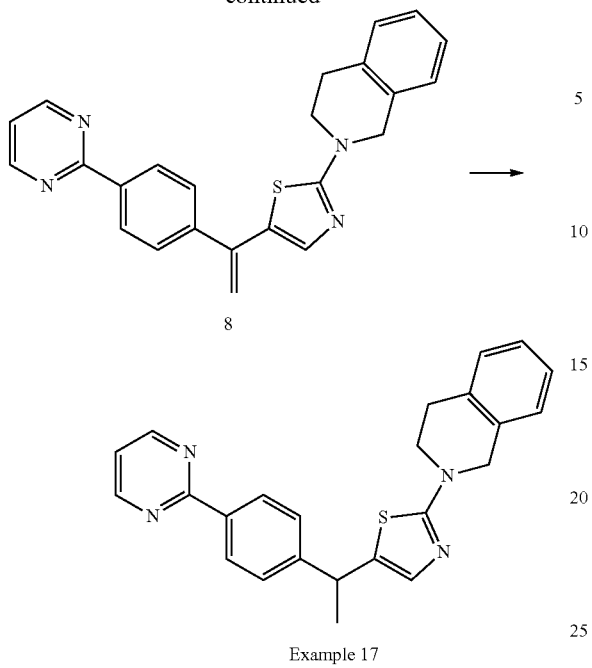

Example 17

Procedure:
1. To a solution of compound 1 (2 g, 12.6 mmol) and compound 2 (2.2 g, 13.2 mmol) in CH$_3$CN, was added 0.5M Na$_2$CO$_3$ (2.7 g, 25.2 mmol) and the mixture was purged with N$_2$ for 10 min. Pd(PPh$_3$)$_4$ (800 mg) was then added and the mixture heated at reflux overnight. The mixture was filtered, diluted with water and extracted with EA. The resulting aqueous mixture was acidified to pH=1 and a precipitate formed. The precipitate was filtered and dried to give 2 g of compound 3.
2. To a mixture of compound 3 (2 g, 10 mmol), EDCI (2.3 g, 12 mmol), HOBT (14 g, 10 mmol), DIEA (2.6 g, 20 mmol) and N,O-dimethylhydroxylamine hydrochloride (1.2 g, 12 mmol) in DCM, stirred at RT for 2 h. Water was added and extracted with DCM. The extracts were concentrated to give 2.5 g of compound 4.
3. To a solution of compound 4 (2.5 g, 10.3 mmol) in THF at −78° C. was added CH$_3$MgBr (4.8 mL, 13.4 mmol) dropwise The cooling bath was removed and the mixture stirred at RT for 1 h. The mixture was diluted with with water, extracted with EA, and the extracts concentrated to give 1.7 g of compound 5.
4. To a solution of 2-chlorothiazole (1.2 g, 9.4 mmol) in dry THF (10 mL) at −78° C. under N$_2$ was added n-BuLi (4 mL, 9.4 mmol) dropwise. After 1 hour a solution of Compound 5 (1.7 g, 8.6 mmol) was added dropwise. The resulting solution was slowly warmed to RT. The reaction was diluted with NH$_4$Cl solution and extracted with EA. The organic extracts were concentrated to give a crude oil. The crude product was purified by silica gel chromatography to afford 1.2 g of Compound 6.
5. To a solution of Compound 6 (400 mg, 1.4 mmol) in DMF (10 mL) were added 1,2,3,4-tetrahydroisoquinoline (280 mg, 2.1 mmol)) and K$_2$CO$_3$ (390 mg, 2.8 mmol). The reaction mixture was stirred at 80° C. overnight. After cooling to RT, the residue was treated with water and extracted with EA. The organic extracts were washed with water, brine, dried over anhydrous Na$_2$SO$_4$, filtered and concentrated to give a crude oil. The crude product was purified by silica gel chromatography to afford 34 mg of Compound 7

6. To a solution of Compound 7 (1 g, 3.28 mmol) in DCE (20 mL) was added TES-H (1.1 g, 9.8 mmol), the mixture cooled to 0° C. and TFA (3.7 g, 32.8 mmol) was added dropwise. The resulting solution was stirred at 60° C. for 4 hours. The residue was concentrated and purified by silica gel chromatography to afford 800 mg Compound 8
7. To a solution of Compound 8 (150 mg, 0.4 mmol) in MeOH (10 mL) was added Pd/C (20 mg). The reaction mixture was stirred at RT under a H$_2$ balloon overnight. The residue was filtered, the filter cake washed with MeOH the filtrate was concentrated and purified by silica gel chromatography to afford 34 mg of Example 17

$^1$HNMR (CDCl$_3$, 300 MHz) δ 1.6-1.7 (d, 2H), 3.0-3.1 (t, 2H), 3.7-3.8 (t, 2H), 4.2-4.3 (m, 1H), 4.6-4.7 (s, 2H), 6.4-6.5 (s, 1H), 7.0-7.1 (s, 1H), 7.2-7.4 (m, 4H), 7.4-7.5 (d, 2H), 7.6-7.8 (m, 3H), 7.9-8.0 (s, 1H).

LC-MS: m/z=399 (M+1)$^+$.

Synthesis of Examples 18 and 19

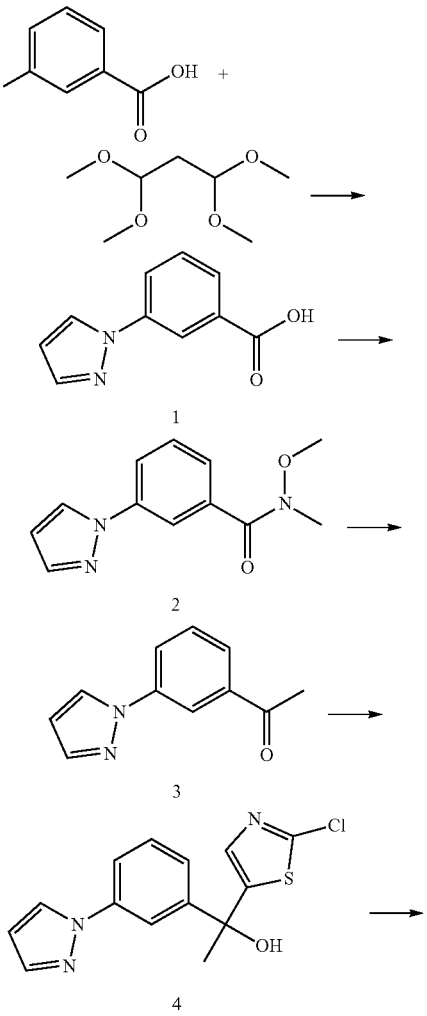

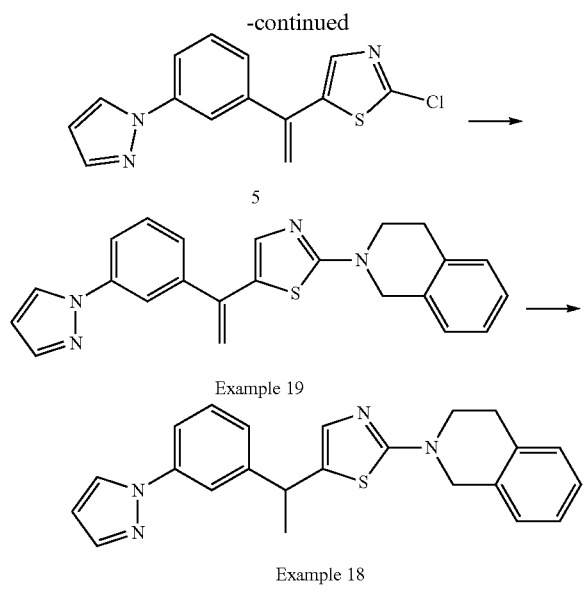

Example 19

Example 18

Procedure:
1. To a solution of 3-hydrazinylbenzoic acid (10 g, 65.7 mmol) in EtOH/H₂O (200 mL, 1:1) was added 1,1,3,3-tetramethoxypropane (16 mL, 65.7 mmol). The resulting solution was stirred at reflux for 2 hours. The solvent was removed in vacuo, the residue was purified by recrystallization to afford Compound 1 (9 g, 73%).
   ¹HNMR (CDCl₃, 300 MHz) δ 6.5-6.6 (s, 1H), 7.5-7.7 (t, 1H), 7.7-7.8 (s, 1H), 8.0-8.2 (m, 3H), 8.4-8.5 (s, 1H).
2. To a solution of Compound 1 (5 g, 26.6 mmol) in DCM (100 mL) were added N,O-dimethylhydroxylamine hydrochloride (3.1 g, 32 mmol), EDCI (6.1 g, 32 mmol), HOBt (3.6, 26.6 mmol) and DIEA (8.8 mL, 53.2 mmol). The resulting solution was stirred at RT overnight. The residue was treated with water and extracted with DCM. The organic extracts were washed with brine, dried over anhydrous Na₂SO₄, filtered and concentrated to give a crude oil. The crude product was purified by silica gel chromatography to afford Compound 2 (3.2 g, 57%).
   ¹HNMR (CDCl₃, 300 MHz) δ 3.3-3.4 (s, 3H), 3.5-3.6 (s, 3H), 6.4-.6.5 (s, 1H), 7.4-7.5 (t, 1H), 7.5-7.6 (d, 1H), 7.7-7.8 (s, 1H), 7.8-7.9 (d, 1H), 7.9-8.0 (d, 2H).
3. To a solution of Compound 2 (3 g, 13 mmol) in ether (30 mL) at 0° C. was added a solution of MeMgI in ether (20 mL, 19 mmol) dropwise. The mixture was stirred at room-temp for 2 hours. The mixture was diluted with saturated ammonium chloride at 0° C. The residue was treated with water and extracted with EA. The organic extracts were washed with brine, dried over anhydrous Na₂SO₄, filtered and concentrated to give a crude oil. The crude product was purified by silica gel chromatography to afford Compound 3 (2 g, 83.3%).
   ¹HNMR(CDCl₃, 300 MHz) δ 2.6-2.7 (s, 3H), 6.4-6.5 (s, 1H), 7.5-7.6 (t, 1H), 7.7-7.8 (s, 1H), 7.8-8.1 (m, 3H), 8.2-8.3 (s, 1H).
4. To a solution of 2-chlorothiazole (1.7 g, 14 mmol) in dry THF (30 mL) at −78° C. under N₂ was added n-BuLi (5.6 mL, 14 mmol) dropwise. After 1 hour a solution of Compound 3 (2 g, 10.6 mmol) was added dropwise. The resulting solution was slowly warmed to RT. The reaction was diluted with NH₄Cl solution and extracted with EA. The organic extracts were concentrated to give a crude oil. The crude product was purified by silica gel chromatography to afford Compound 4 (1 g, 31%).
5. To a solution of Compound 4 (1.5 g, 4.29 mmol) in DCE (30 mL) was added TES-H (1.65 g, 14.7 mmol), the mixture cooled to 0° C. and TFA (5.6 g, 49.2 mmol) was added dropwise at 0° C. The resulting solution was stirred at 60° C. for 4 hours. The residue was concentrated and purified by silica gel chromatography to afford Compound 5 (800 mg, 57%).
6. To a solution of Compound 5 (400 mg, 1.4 mmol) in DMF (10 mL) were added 1,2,3,4-tetrahydroisoquinoline (280 mg, 2.1 mmol)) and K₂CO₃ (390 mg, 2.8 mmol). The reaction mixture was stirred at 80° C. overnight. After cooling to RT, the residue was treated with water and extracted with EA. The organic extracts were washed with water, brine, dried over anhydrous Na₂SO₄, filtered and concentrated to give a crude oil. The crude product was purified by silica gel chromatography to afford Example 19 (120 mg, 18%).
   ¹HNMR (CDCl₃, 300 MHz) δ 3.0-3.1 (t, 2H), 3.7-3.8 (t, 2H), 4.6-4.7 (s, 2H), 5.1-5.3 (ss, 2H), 6.4-6.5 (s, 1H), 7.0-7.1 (s, 1H), 7.1-7.3 (m, 4H), 7.3-7.5 (m, 2H), 7.6-7.8 (m, 3H), 7.9-8.0 (s, 1H). LC-MS: m/z=385.2 (M+1)+.
7. To a solution of Example 19 (100 mg, 0.27 mmol) in MeOH (10 mL) was added Pd/C (10 mg). The reaction mixture was stirred at RT under a H₂ balloon overnight. The residue was filtered, the filter cake washed with MeOH, the filtrate was concentrated and purified by silica gel chromatography to afford Example 18 (35 mg, 35%).
   ¹HNMR (CDCl₃, 300 MHz) δ 1.6-1.7 (d, 2H), 3.0-3.1 (t, 2H), 3.7-3.8 (t, 2H), 4.2-4.3 (m, 1H), 4.6-4.7 (s, 2H), 6.4-6.5 (s, 1H), 7.0-7.1 (s, 1H), 7.2-7.4 (m, 4H), 7.4-7.5 (d, 2H), 7.6-7.8 (m, 3H), 7.9-8.0 (s, 1H).
   LC-MS: m/z=387.2 (M+1)+.

Synthesis of Example 20

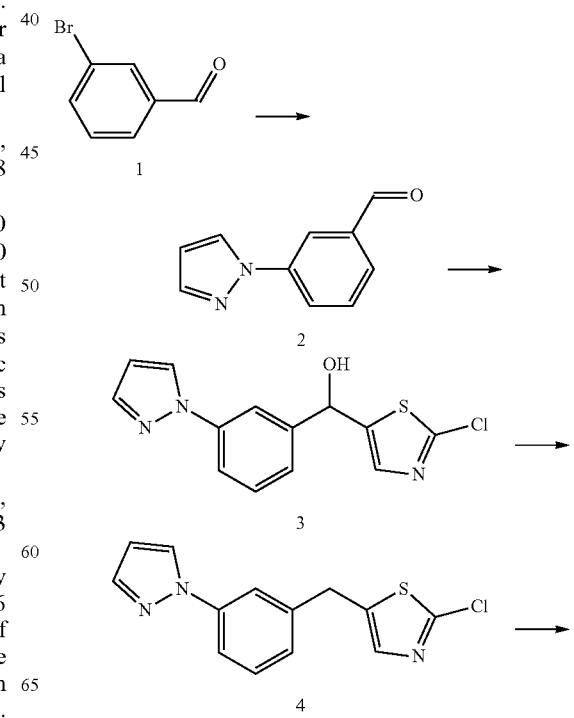

-continued

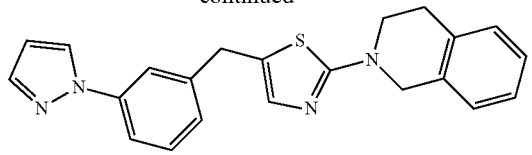

Example 20

Procedure:

1. To a solution of Compound 1 (10 g, 54 mmol) in dry DMF (100 mL) were added pyrazole (3.7 g, 54 mmol), Cs$_2$CO$_3$ (26.4 g, 81 mmol) and CuI (1 g, 5.4 mmol). The resulting solution was stirred at 120° C. for overnight. After cooling to RT, the residue was treated with water and extracted with EA. The organic extracts were washed with water, brine, dried over anhydrous Na$_2$SO$_4$, filtered and concentrated to give a crude oil. The crude product was purified by silica gel chromatography to afford Compound 2 (4 g, 43%).

$^1$HNMR (CDCl$_3$, 300 MHz) δ 6.5-6.6 (s, 1H), 7.6-7.7 (m, 1H), 7.7-7.9 (m, 2H), 8.0-8.1 (m, 2H), 8.2-8.3 (s, 1H), 10.0-10.1 (s, 1H).

2. To a solution of 2-chlorothiazole (1.45 g, 12.1 mmol) in dry THF (10 mL) at −78° C. under N$_2$ was added n-BuLi (5 mL, 12.1 mmol) dropwise. After 1 hour solution of Compound 2 (1.6 g, 9.3 mmol) was added dropwise. The resulting solution was slowly warmed to RT. The reaction was diluted with NH$_4$Cl solution and extracted with EA. The organic extracts were concentrated to give a crude oil. The crude product was purified by silica gel chromatography to afford Compound 3 (1.2 g, 50%).

$^1$HNMR (CDCl$_3$, 300 MHz) δ 6.1-6.2 (s, 1H), 6.5-6.6 (s, 1H), 7.2-7.4 (t, 2H), 7.4-7.5 (t, 1H), 7.6-7.7 (d, 1H), 7.7-7.9 (ss, 2H), 7.9-8.0 (s, 1H).

3. To a solution of Compound 3 (1.2 g, 4.1 mmol) in DCE (20 mL) was added TES-H (1.4 g, 12.8 mmol), the mixture cooled to 0° C. and TFA (4.7 g, 41 mmol) was added dropwise. The resulting solution was stirred at 60° C. for 4 hours. The residue was concentrated and purified by silica gel chromatography to afford Compound 4 (1 g, 91%).

$^1$HNMR (CDCl$_3$, 300 MHz) δ 4.2-4.3 (s, 2H), 6.4-6.5 (s, 1H), 7.1-7.2 (s, 1H), 7.3-7.4 (s, 1H), 7.4-7.5 (t, 1H), 7.5-7.6 (d, 1H), 7.6-7.7 (s, 1H), 7.7-7.8 (s, 1H), 7.9-8.0 (s, 1H).

4. To a solution of Compound 4 (500 mg, 1.8 mmol) in DMF (10 mL) were added 1,2,3,4-tetrahydroisoquinoline (362 mg, 2.7 mmol)) and K$_2$CO$_3$ (500 mg, 3.6 mmol). The reaction mixture was stirred at 80° C. overnight. After cooling to RT, the residue was treated with water and extracted with EA. The organic extracts were washed with water, brine, dried over anhydrous Na$_2$SO$_4$, filtered and concentrated to give a crude oil. The crude product was purified by silica gel chromatography to afford Example 20 (30 mg, 4.4%).

$^1$HNMR (CDCl$_3$, 300 MHz) δ 2.9-3.0 (t, 2H), 3.6-3.7 (t, 2H), 4.0-4.1 (s, 2H), 4.6-4.7 (s, 2H), 6.4-6.5 (s, 1H), 7.0-7.1 (s, 1H), 7.1-7.3 (m, 4H), 7.3-7.4 (d, 2H), 7.5-7.6 (d, 2H), 7.7-7.8 (s, 1H), 7.9-8.0 (s, 1H).

LC-MS: m/z=373.2 (M+1)+.

Synthesis of Examples 21

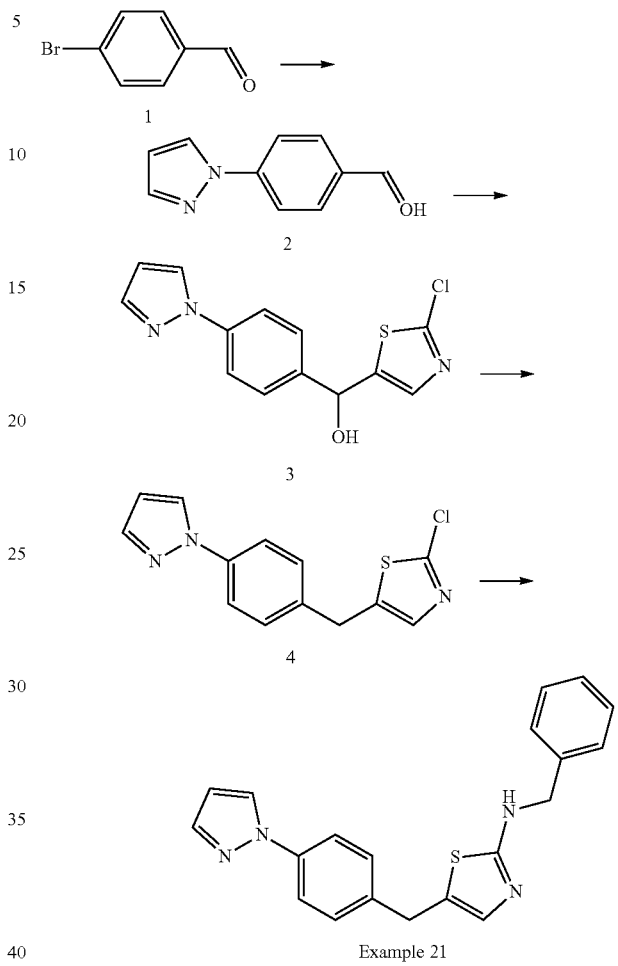

Example 21

Procedure:

1. To a solution of Compound 1 (30 g, 162.1 mmol) in dry DMF (200 mL) were added 1H-pyrazole (11 g, 162.1 mmol) and K$_2$CO$_3$ (24.8 g, 178.3 mmol). The resulting solution was stirred at 80° C. for 12 hours. After cooling to RT, the residue was treated with water and extracted with EA. The organic extracts were washed with water, brine, dried over anhydrous Na$_2$SO$_4$, filtered and concentrated to give a crude oil. The crude product was purified by recrystallization to afford Compound 2 (25 g, 89%).

2. To a solution of 2-chlorothiazole (16.7 g, 139.5 mmol) in dry THF (200 mL) was added n-BuLi (55.8 mL, 139.5 mmol) dropwise at −78° C. under N$_2$. After 1 hour stirring at this temp. a solution of Compound 2 (20 g, 116 mmol) was added dropwise at −78° C. The resulting solution was allowed to slowly warmed to RT. The reaction was diluted with NH$_4$Cl solution and extracted with EA. The organic extracts were concentrated to give a crude oil. The crude product was purified by silica gel chromatography to afford Compound 3 (15 g, 44.4%).

$^1$HNMR (CDCl$_3$, 300 MHz) δ 4.0-4.1 (m, 1H), 5.9-6.0 (s, 1H), 6.5 (s, 1H), 7.2-7.3 (s, 1H), 7.4-7.5 (d, 2H), 7.6-7.7 (d, 2H), 7.7-7.8 (s, 1H), 7.9-8.0 (s, 1H).

3. To a solution of Compound 3 (15 g, 51.5 mmol) in DCE (100 mL) was added TES-H (17 g, 155 mmol) and TFA (58.7 g, 515 mmol) was added dropwise at 0° C. The resulting solution was stirred at 60° C. over night. The residue was concentrated and purified by silica gel chromatography to afford Compound 4 (8 g, 56.4%).

$^1$HNMR (CDCl$_3$, 300 MHz) δ 4.1-4.2 (s, 1H), 5.5-5.6 (m, 1H), 6.5-6.6 (s, 1H), 7.2-7.4 (m, 3H), 7.6-7.7 (d, 2H), 7.7-7.8 (s, 1H), 7.9-8.0 (s, 1H).

4. To a solution of Compound 4 (500 mg, 1.8 mmol) in DMSO (10 mL) were added benzyl amine (600 mg, 5.4 mmol)) and K$_2$CO$_3$ (500 mg, 3.6 mmol). The reaction mixture was stirred at 80° C. overnight. After cooling to RT, the residue was treated with water and extracted with EA. The organic extracts were washed with water, brine, dried over anhydrous Na$_2$SO$_4$, filtered and concentrated to give a crude oil. The crude product was purified by silica gel chromatography to afford Example 21 (45 mg, 7.2%).

$^1$HNMR (CDCl$_3$, 300 MHz) δ 4.1-4.2 (s, 1H), 4.4-4.5 (m, 2H), 4.8-4.9 (m, 1H), 5.5-5.6 (m, 1H), 6.5 (s, 1H), 6.8-6.9 (s, 1H), 7.3-7.4 (m, 5H), 7.6-7.7 (d, 2H), 7.7-7.8 (s, 1H), 7.9 (s, 1H).

LC-MS: m/z=347.1 (M+1)+.

The compounds listed in Table 1 below were prepared in a similar manner to that described in Example 21, where the conditions in step 4 are used substituting the appropriate amine as indicated in Table 1.

TABLE 1

| Example | Amine | Final Product |
| --- | --- | --- |
| Example 22 | [structure: azetidine with isopropoxy] | [structure] |
| Example 23 | [structure: 1,2,3,4-tetrahydroquinoline] | [structure] |
| Example 24 | [structure: 4-isopropylbenzylamine] | [structure] |
| Example 25 | [structure: octahydropyrano-piperidine] | [structure] |
| Example 26 | [structure: α-methylbenzylamine] | [structure] |
| Example 27 | [structure: morpholine] | [structure] |
| Example 28 | [structure: 7-cyano-1,2,3,4-tetrahydroisoquinoline] | [structure] |

Spectral data for the examples listed in Table 1 are presented below:

Example 22

(33 mg, 5.1%) $^1$HNMR (CDCl$_3$, 300 MHz) δ 1.1-1.2 (d, 6H), 3.6-3.7 (m, 2H), 3.9 (m, 2H), 4.0-4.1 (s, 2H), 4.2-4.3 (m, 2H), 4.5 (m, 1H), 6.4-6.5 (s, 1H), 6.9 (s, 1H), 7.3-7.4 (d, 2H), 7.6-7.7 (d, 2H), 7.7-7.8 (s, 1H), 7.9 (s, 1H).

LC-MS: m/z=355.2 (M+1)$^+$.

Example 23

(33 mg, 4.9%) $^1$HNMR (CDCl$_3$, 300 MHz) δ 2.0-2.1 (m, 2H), 2.7-2.8 (m, 2H), 3.8-3.9 (m, 2H), 4.0-4.1 (s, 2H), 6.4-6.5 (s, 1H), 6.9-7.0 (m, 1H), 7.1-7.2 (m, 3H), 7.3-7.4 (m, 3H), 7.6-7.7 (d, 2H), 7.7-7.8 (m, 2H), 7.9 (s, 1H).

LC-MS: m/z=373.1 (M+1)$^+$.

Example 24

(77 mg, 10.9%) $^1$HNMR (CDCl$_3$, 300 MHz) δ 1.2-1.3 (d, 8H), 2.8-3.0 (s, 1H), 4.0-4.1 (s, 2H), 4.3-4.5 (s, 2H), 6.4-6.5 (s, 1H), 6.9 (s, 1H), 7.3-7.4 (d, 2H), 7.6-7.7 (d, 2H), 7.7-7.8 (s, 1H), 7.9 (s, 1H).

LC-MS: m/z=389.2 (M+1)$^+$.

Example 25

(33 mg, 4.8%) $^1$HNMR (CDCl$_3$, 300 MHz) δ 1.6-1.8 (m, 8H), 1.8-1.9 (m, 3H), 3.2-3.3 (m, 1H), 3.4-3.5 (m, 2H), 3.7-3.8 (m, 3H), 4.0 (s, 3H), 4.6-4.7 (s, 3H), 6.4-6.5 (s, 1H), 6.9 (s, 1H), 7.2-7.4 (m, 2H), 7.6-7.7 (d, 2H), 7.7-7.8 (s, 1H), 7.9 (s, 1H).

LC-MS: m/z=381.2 (M+1)$^+$.

Example 26

(150 mg, 22.8%) $^1$HNMR (CDCl$_3$, 300 MHz) δ 1.5 (m, 3H), 3.9-4.0 (d, 1H), 4.5-4.6 (m, 1H), 5.2-5.3 (m, 1H), 5.5-5.7 (m, 1H), 6.4-6.50 (s, 1H), 6.8-6.9 (s, 1H), 7.4-7.5 (s, 5H), 7.6-7.7 (d, 1H), 7.7-7.8 (s, 1H), 7.9 (s, 1H), 8.2-8.3 (s, 1H).

LC-MS: m/z=361.2 (M+1)$^+$.

Example 27

(44 mg, 6.7%) $^1$HNMR (CDCl$_3$, 300 MHz) δ 3.4-3.5 (m, 4H), 3.8-3.9 (m, 4H), 4.0-4.1 (s, 2H), 6.5 (s, 1H), 7.0 (s, 1H), 7.3-7.4 (m, 2H), 7.6-7.7 (d, 1H), 7.7-7.8 (s, 1H), 7.9-8.0 (s, 1H).

LC-MS: m/z=327.1 (M+1)$^+$.

Example 28

(32 mg, 4.4%) $^1$HNMR (CDCl$_3$, 300 MHz) δ 3.0 (m, 2H), 3.7-3.8 (m, 2H), 4.0-4.1 (s, 2H), 6.5 (s, 1H), 7.0 (s, 1H), 7.3-7.4 (m, 4H), 7.4-7.5 (s, 1H), 7.4-7.5 (s, 4H), 7.6-7.7 (s, 1H), 7.6-7.7 (d, 1H), 7.7-7.8 (s, 1H), 7.9-8.0 (s, 1H).

LC-MS: m/z=398.2 (M+1)$^+$.

Synthesis of Example 29

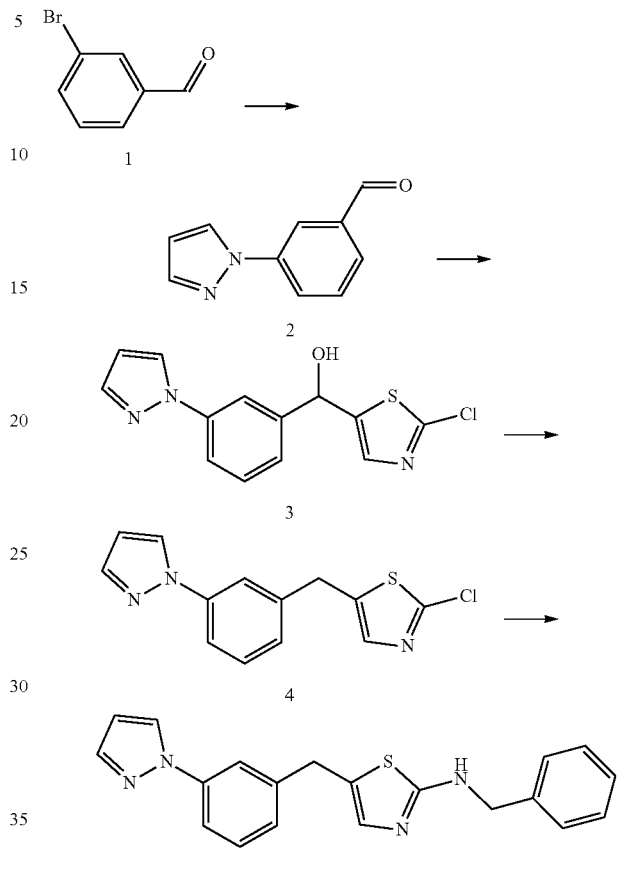

Example 29

Procedure:
1. To a solution of Compound 1 (30 g, 162.1 mmol) in dry DMF (200 mL) were added 1H-pyrazole (11 g, 162.1 mmol), Cs$_2$CO$_3$ (58 g, 178.3 mmol), CuI (58 g), 18-Crown-6 (3 g). The resulting solution was stirred at 80° C. for 24 hours. After cooling to RT, the residue was treated with water and extracted with EA. The organic extracts were washed with water, brine, dried over anhydrous Na$_2$SO$_4$, filtered and concentrated to give a crude oil. The crude product was purified by recrystallization to afford Compound 2 (20 g, 71.3%).
2. To a solution of 2-chlorothiazole (10 g, 83.7 mmol) in dry THF (100 mL) was added n-BuLi (33.5 mL, 83.7 mmol) dropwise at −78° C. under N$_2$. After 1 hour stirring at this temp. a solution of Compound 2 (12 g, 69.7 mmol) was added dropwise at −78° C. The resulting solution was allowed to slowly warmed to RT. The reaction was diluted with NH$_4$Cl solution and extracted with EA. The organic extracts were concentrated to give a crude oil. The crude product was purified by silica gel chromatography to afford Compound 3 (12 g, 59.2%).

$^1$HNMR (CDCl$_3$, 300 MHz) δ 3.0-3.2 (m, 1H), 6.0-6.1 (s, 1H), 6.4-6.5 (s, 1H), 7.2-7.3 (d, 2H), 7.4-7.5 (d, 1H), 7.6-7.7 (d, 1H), 7.7-7.8 (s, 1H), 7.8-7.9 (s, 1H), 7.9-8.0 (s, 1H).
3. To a solution of Compound 3 (10 g, 34.4 mmol) in DCE (60 mL) was added TES-H (11.3 g, 103.1 mmol). Then TFA (39.2 g, 344 mmol) was added dropwise at 0° C. The resulting solution was stirred at 60° C. for over night. The residue was concentrated and purified by silica gel chromatography to afford Compound 4 (6 g, 79.4%).
¹HNMR (CDCl₃, 300 MHz) δ 4.2-4.3 (s, 1H), 6.5-6.6 (m, 1H), 7.1-7.2 (d, 1H), 7.3-7.4 (s, 1H), 7.4-7.5 (t, 1H), 7.5-7.6 (d, 1H), 7.6-7.7 (s, 1H), 7.7-7.8 (s, 1H), 7.9-8.0 (s, 1H).

4. To a solution of Compound 4 (500 mg, 1.8 mmol) in DMSO (10 mL) were added benzylamine (600 mg, 5.4 mmol)) and K₂CO₃ (500 mg, 3.6 mmol). The reaction mixture was stirred at 80° C. overnight. After cooling to RT, the residue was treated with water and extracted with EA. The organic extracts were washed with water, brine, dried over anhydrous Na₂SO₄, filtered and concentrated to give a crude oil. The crude product was purified by silica gel chromatography to afford Example 29 (270 mg, 42.9%).
¹HNMR (CDCl₃, 300 MHz) δ 4.0-4.1 (s, 1H), 4.4-4.5 (m, 2H), 5.2-5.3 (m, 1H), 6.4-6.5 (S, 1H), 6.9 (s, 1H), 7.1-7.2 (s, 1H), 7.3-7.4 (m, 5H), 7.5-7.6 (d, 2H), 7.7-7.8 (s, 1H), 7.9-8.0 (s, 1H).

LC-MS: m/z=347.1 (M+1)⁺.

The compounds listed in Table 2 below were prepared in a similar manner to that described in Example 29, where the conditions in step 4 are used substituting the appropriate amine as indicated in Table 2.

TABLE 2

| Example | Amine | Final Product |
|---------|-------|---------------|
| Example 30 | | |
| Example 31 | | |
| Example 32 | | |
| Example 33 | | |
| Example 34 | | |
| Example 35 | | |
| Example 36 | | |

Spectral data for the examples listed in Table 2 are presented below:

Example 30

(146.5 mg, 22.75%) $^1$HNMR (CDCl$_3$, 300 MHz) δ 1.1-1.2 (d, 6H), 3.6-3.7 (m, 2H), 3.9 (m, 2H), 4.0-4.1 (s, 2H), 4.2-4.3 (m, 2H), 4.5 (m, 1H), 6.5 (s, 1H), 6.9-7.0 (s, 1H), 7.1-7.2 (d, 1H), 7.4 (d, 1H), 7.5-7.6 (d, 2H), 7.7-7.8 (s, 1H), 7.9-8.0 (s, 1H).

LC-MS: m/z=355.2 (M+1)$^+$.

Example 31

(55 mg, 8.1%) $^1$HNMR (CDCl$_3$, 300 MHz) δ 1.9-2.0 (m, 2H), 2.7-2.8 (m, 2H), 3.8-3.9 (m, 2H), 4.0-4.1 (s, 2H), 6.4-6.5 (s, 1H), 6.9-7.0 (m, 1H), 7.1-7.2 (m, 3H), 7.3-7.4 (m, 1H), 7.5-7.6 (d, 2H), 7.7-7.8 (m, 2H), 7.9 (s, 1H).

LC-MS: m/z=373.1 (M+1)$^+$.

Example 32

(68 mg, 9.6%) $^1$HNMR (CDCl$_3$, 300 MHz) δ 1.2-1.3 (d, 8H), 2.8-3.0 (s, 1H), 4.0-4.1 (s, 2H), 4.3-4.5 (s, 2H), 6.4-6.5 (s, 1H), 6.9 (s, 1H), 7.3-7.4 (m, 5H), 7.4-7.5 (m, 1H), 7.6-7.7 (d, 2H), 7.7-7.8 (s, 1H), 7.9 (s, 1H).

LC-MS: m/z=389.2 (M+1)$^+$.

Example 33

(171 mg, 24.7%) $^1$HNMR (CDCl$_3$, 300 MHz) δ 1.7-1.9 (m, 8H), 1.8-1.9 (m, 3H), 3.2-3.3 (m, 1H), 3.4-3.5 (m, 2H), 3.7-3.8 (m, 3H), 3.9-4.1 (s, 3H), 6.4-6.5 (s, 1H), 6.9 (s, 1H), 7.1-7.2 (m, 2H), 7.4 (d, 1H), 7.5-7.6 (m, 2H), 7.7-7.8 (s, 1H), 7.9 (s, 1H).

LC-MS: m/z=381.2 (M+1)$^+$.

Example 34

(43 mg, 6.6%) $^1$HNMR (CDCl$_3$, 300 MHz) δ 1.5-1.6 (s, 3H), 3.9-4.0 (m, 2H), 4.6-4.7 (m, 1H), 5.3-5.4 (m, 1H), 6.4-6.5 (s, 1H), 6.9 (s, 1H), 7.1-7.2 (d, 1H), 7.4-7.5 (s, 5H), 7.5-7.6 (s, 2H), 7.7-7.8 (s, 1H), 7.9 (s, 1H).

LC-MS: m/z=361.2 (M+1)$^+$.

Example 35

(37 mg, 6.2%) $^1$HNMR (CDCl$_3$, 300 MHz) δ 3.4-3.5 (m, 4H), 3.8 (m, 4H), 4.0-4.1 (s, 2H), 6.5 (s, 1H), 7.0 (s, 1H), 7.1-7.2 (d, 1H), 7.3-7.5 (m, 2H), 7.5-7.7 (m, 2H), 7.7-7.8 (s, 1H), 7.9-8.0 (s, 1H).

LC-MS: m/z=327.1 (M+1)$^+$.

Example 36

(32.5 mg, 4.5%) $^1$HNMR (CDCl$_3$, 300 MHz) δ 3.0 (m, 2H), 3.7-3.8 (m, 2H), 4.0-4.1 (s, 2H), 6.6-4.8 (m, 1H), 6.5 (s, 1H), 7.0 (s, 1H), 7.1-7.2 (s, 1H), 7.4-7.6 (s, 4H), 7.7-7.8 (s, 1H), 7.9-8.0 (s, 1H).

LC-MS: m/z=398.2 (M+1)$^+$.

Synthesis of Example SBX080

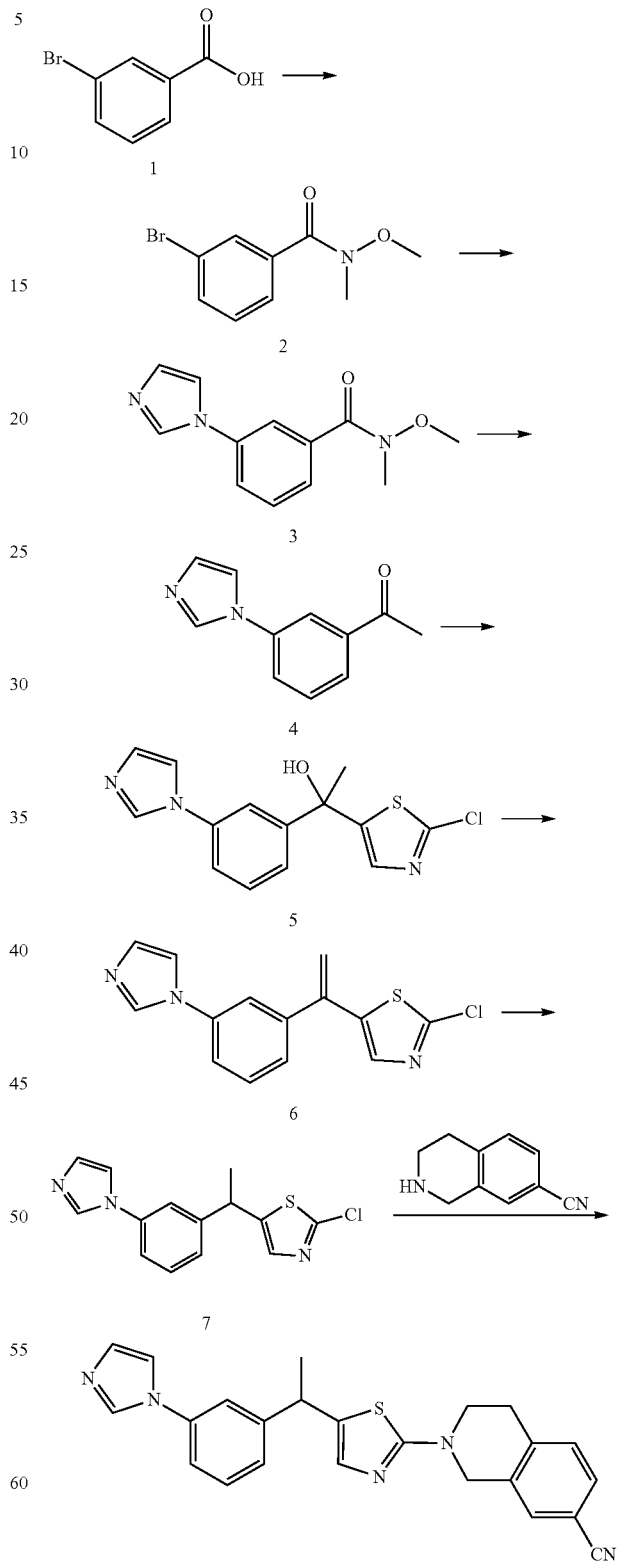

Procedure:
1. To a solution of Compound 1 (20 g, 99.5 mmol) in dry DCM (200 mL) were added N,O-dimethylhydroxylamine hydrochloride (14.5 g, 149 mmol), EDCI (28.6 g, 149 mmol), HOBt (14.8 g, 109 mmol), DIEA (38 g, 298 mmol) and the solution stirred at RT for 24 hours. The mixture was diluted with water and extracted with DCM. The combined extracts were washed with water, brine, dried over anhydrous $Na_2SO_4$, filtered and concentrated to give an oil. The crude product was purified to afford Compound 2 (21.7 g, 89.3%).
2. A mixture of Compound 2 (20 g, 82 mmol), imidazole (6.2 g, 90 mmol), $Cs_2CO_3$ (29 g, 90 mmol), CuI (2 g), 18-Crown-6 (2 g) in dry DMF (200 mL) was stirred at 80° C. for 24 hours and cooled to RT. The mixture was diluted with water and extracted with EA. The combined extracts were washed with water, brine, dried over anhydrous $Na_2SO_4$, filtered and concentrated to give an oil. The crude product was purified by recrystallization to afford Compound 3 (14 g, 74.3%).
3. To a solution of Compound 3 (10 g, 43.2 mmol) in dry THF (80 mL) at 0° C. under $N_2$ was added 2.8 M MeMgBr (30.7 mL, 86 mmol) dropwise. The resulting solution was warmed to RT and monitored by TLC. When TLC indicated the reaction was complete, it was diluted with $NH_4Cl$ solution and extracted with EA. The combined extracts were concentrated to give an oil. The crude product was purified by silica gel chromatography to afford Compound 4 (5.5 g, 68.3%).
$^1$HNMR (CDCl$_3$, 300 MHz) δ 2.7-2.8 (s, 3H), 6.5 (s, 1H), 7.2-7.3 (s, 1H), 7.5-7.6 (m, 1H), 7.8-7.9 (d, 2H), 7.9-8.0 (d, 1H), 8.0-8.1 (s, 1H), 8.2-8.4 (s, 1H).
4. To a solution of 2-chlorothiazole (5.5 g, 45.8 mmol) in dry THF (100 mL) at −78° C. was added n-BuLi (18.3 mL, 45.8 mmol) dropwise. After 1 hour a solution of Compound 4 (7.1 g, 38.2 mmol) was added dropwise. The resulting solution was warmed to RT. The reaction was diluted with $NH_4Cl$ solution and extracted with EA. The combined extracts were concentrated to give an oil which was purified by silica gel chromatography to afford Compound 5 (9 g, 77%).
$^1$HNMR (CDCl$_3$, 300 MHz) δ 2.0-2.1 (s, 3H), 2.9-3.1 (s, 1H), 6.4-6.5 (s, 1H), 7.3 (s, 1H), 7.4-7.5 (m, 3H), 7.6-7.7 (d, 1H), 7.7-7.8 (s, 1H), 7.9-8.0 (d, 2H).
5. To a mixture of Compound 5 (9 g, 29.4 mmol) and TFA (21.9 mL, 294 mmol) in DCE (60 mL) at 0° C. was added triethylsilane (TES, 17.8 mL, 88.2 mmol) dropwise. The resulting solution was stirred at RT 3 h. The reaction was diluted with $H_2O$ and extracted with DCM. The combined extracts were concentrated to give an oil and purified by silica gel chromatography to afford Compound 6 (6.6 g, 78.5%).
$^1$HNMR (CDCl$_3$, 300 MHz) δ 5.4-5.5 (s, 1H), 5.5-5.6 (s, 1H), 6.4-6.5 (s, 1H), 7.3 (s, 1H), 7.4-7.5 (m, 2H), 7.6-7.7 (d, 1H), 7.7-7.8 (s, 1H), 7.9-8.0 (d, 2H), 8.1-8.2 (s, 1H).
6. To a solution of Compound 6 (6.6 g, 22.9 mmol) in EtOH (60 mL) was added $NaBH_4$ (25.8 g, 68 mmol) in three portions. The resulting solution was stirred at RT for 6 h. The reaction was concentrated, diluted with $H_2O$ and extracted with EA. The combined extracts were concentrated to give a crude oil and purified by silica gel chromatography to afford Compound 7 (4.8 g, 72.6%).
$^1$HNMR (CDCl$_3$, 300 MHz) δ 1.7-1.8 (d, 3H), 3.4-3.5 (m, 1H), 5.5-5.7 (s, 1H), 7.1-7.2 (s, 1H), 7.2-7.3 (m, 2H), 7.4-7.5 (d, 1H), 7.6-7.7 (d, 1H), 7.7-7.8 (s, 1H), 7.8-7.9 (s, 1H), 7.9-8.0 (s, 1H).

7. To a solution of Compound 7 (300 mg, 1 mmol) in DMSO (3 mL) were added 1,2,3,4-tetrahydroisoquinoline-7-carbonitrile hydrochloride (290 mg, 1.5 mmol)) and $K_2CO_3$ (270 mg, 2 mmol). The reaction mixture was stirred at 140° C. overnight, cooled to RT and the mixture was diluted with water and extracted with EA. The combined organic extracts were washed with water, brine, dried over anhydrous $Na_2SO_4$, filtered and concentrated to give an SBX080 (56 mg, 13.2%).
$^1$HNMR (CDCl$_3$, 300 MHz) δ 2.6-2.8 (m, 3H), 2.9-3.1 (m, 2H), 3.4-3.5 (s, 2H), 3.7-3.8 (m, 2H), 4.2-4.3 (s, 1H), 4.6-4.7 (s, 2H), 6.9-7.0 (s, 1H), 7.1-7.2 (s, 1H), 7.3 (s, 4H), 7.4-7.5 (m, 3H), 7.6-7.7 (m, 1H), 7.7-7.8 (d, 1H). LC-MS: m/z=412 (M+1)$^+$.

Preparation of Intermediate 1

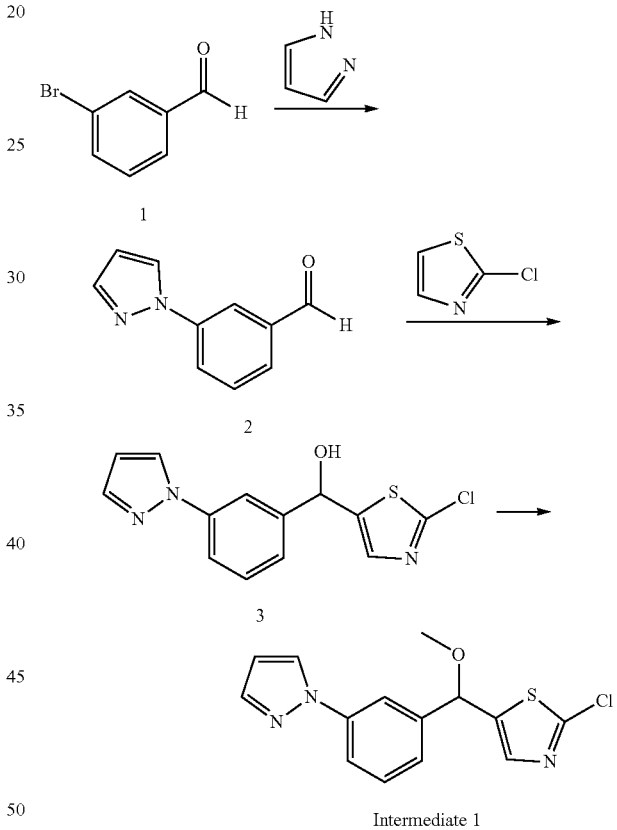

Intermediate 1

Procedure:
1. A mixture of Compound 1 (30 g, 162.1 mmol), 1H-pyrazole (11 g, 162.1 mmol), $Cs_2CO_3$ (58 g, 178.3 mmol), CuI (3 g), 18-Crown-6 (3 g) in dry DMF (200 mL) was stirred at 80° C. for 24 hours and cooled to RT. The mixture was diluted with water and extracted with EA. The combined extracts were washed with water, brine, dried over anhydrous $Na_2SO_4$, filtered and concentrated to give an oil. The crude product was purified by recrystallization to afford Compound 2 (21 g, 75.3%).
2. To a solution of 2-chlorothiazole (10 g, 83.7 mmol) in dry THF (100 mL) at −78° C. was added n-BuLi (33.5 mL, 83.7 mmol) dropwise. After 1 hour a solution of Compound 2 (12 g, 69.7 mmol) was added dropwise. The resulting solution was warmed to RT. The mixture was diluted with NH$_4$Cl solution and extracted with EA. The combined extracts were concentrated to give an oil. The crude product was purified by silica gel chromatography to afford Compound 3 (11.5 g, 68%).

$^1$HNMR (CDCl$_3$, 300 MHz) δ 3.7-3.8 (s, 1H), 6.0-6.1 (s, 1H), 6.5-6.6 (s, 1H), 7.2-7.4 (d, 2H), 7.4-7.5 (d, 1H), 7.6-7.7 (d, 1H), 7.7-7.8 (s, 1H), 7.8-7.9 (s, 1H), 7.9-8.0 (s, 1H).

3. To a solution of Compound 3 (5 g, 17 mmol) in THF (30 mL) at 0° C. was added NaH (1 g, 26 mmol) slowly and the mixture stirred for 30 minutes. MeI (3.6 g, 26 mmol) was added dropwise at 0° C., the cooling bath was removed and the mixture was stirred at RT for 2 hours. The mixture was diluted with H$_2$O and extracted with EA. The combined extracts were concentrated to give an oil which was purified by silica gel chromatography to afford Intermediate 1 (3.6 g, 69.4%).

$^1$HNMR (CDCl$_3$, 300 MHz) δ 3.4-3.5 (s, 3H), 5.7-5.8 (s, 1H), 6.4-6.5 (s, 1H), 7.2-7.3 (d, 2H), 7.4-7.5 (d, 1H), 7.6-7.7 (d, 1H), 7.7-7.8 (s, 1H), 7.8-7.9 (s, 1H), 7.9-8.0 (s, 1H).

Preparation of Intermediate 2

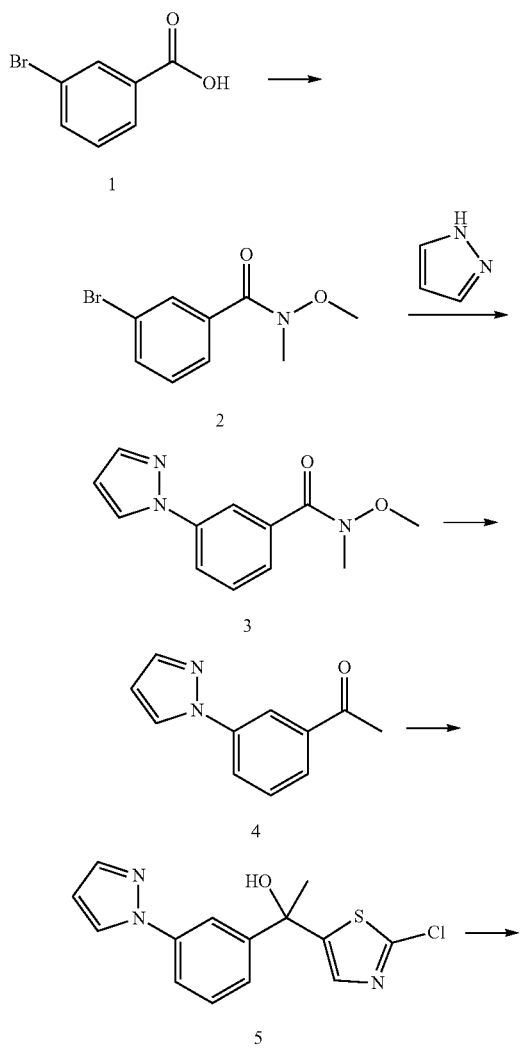

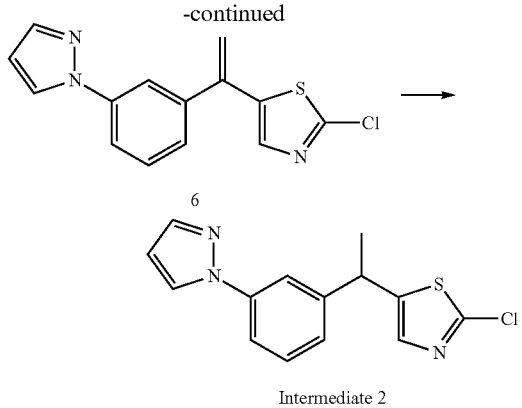

Intermediate 2

Procedure:

1. To a solution of Compound 1 (20 g, 99.5 mmol) in dry DCM (200 mL) were added N,O-dimethylhydroxylamine hydrochloride (14.5 g, 149 mmol), EDCI (28.6 g, 149 mmol), HOBt (14.8 g, 109 mmol), DIEA (38 g, 298 mmol) and the solution stirred at RT for 24 hours. The mixture was diluted with water and extracted with DCM. The combined extracts were washed with water, brine, dried over anhydrous Na$_2$SO$_4$, filtered and concentrated to give an oil. The crude product was purified to afford Compound 2 (20.7 g, 84.3%).

2. A mixture of Compound 2 (20 g, 82 mmol), 1H-pyrazole (6.2 g, 90 mmol), Cs$_2$CO$_3$ (29 g, 90 mmol), CuI (2 g), 18-Crown-6 (2 g) in dry DMF (200 mL) was stirred at 80° C. for 24 hours and cooled to RT. The mixture was diluted with water and extracted with EA. The combined extracts were washed with water, brine, dried over anhydrous Na$_2$SO$_4$, filtered and concentrated to give an oil. The crude product was purified by recrystallization to afford Compound 3 (14.9 g, 79.3%).

3. To a solution of Compound 3 (14 g, 60.5 mmol) in dry THF (100 mL) at 0° C. under N$_2$ was added 2.8 M MeMgBr (43 mL, 121 mmol) dropwise. The mixture was warmed to RT and monitored by TLC. When TLC indicated the reaction was complete, it was diluted with NH$_4$Cl solution and extracted with EA. The combined extracts were concentrated to give an oil. The crude product was purified by silica gel chromatography to afford Compound 4 (7.1 g, 62.8%).

$^1$HNMR (CDCl$_3$, 300 MHz) δ 2.7-2.8 (s, 3H), 6.5 (s, 1H), 7.2-7.3 (s, 1H), 7.5-7.6 (m, 1H), 7.7-7.8 (s, 1H), 7.8-7.9 (d, 1H), 7.9-8.0 (d, 1H), 8.0-8.1 (s, 1H), 8.2-8.4 (s, 1H).

4. To a solution of 2-chlorothiazole (5.5 g, 45.8 mmol) in dry THF (100 mL) at −78° C. under N$_2$ was added 2.5 M n-BuLi (18.3 mL, 45.8 mmol) dropwise. After 1 hour at −78° C. a solution of Compound 4 (7.1 g, 38.2 mmol) in THF was added dropwise. The resulting mixture was warmed to RT, diluted with NH$_4$Cl solution and extracted with EA. The combined extracts were concentrated to give an oil. The crude product was purified by silica gel chromatography to afford Compound 5 (7.9 g, 67%).

$^1$HNMR (CDCl$_3$, 300 MHz) δ 2.0-2.2 (m, 3H), 3.0 (m, 1H), 6.4-6.5 (s, 1H), 7.3-7.5 (m, 3H), 7.7-7.9 (m, 3H), 8.1-8.2 (s, 1H).

5. To a mixture of Compound 5 (7.9 g, 25.8 mmol) and TFA (18.9 mL, 258 mmol) in DCE (60 mL) at 0° C. was added triethylsilane (TES, 15.8 mL, 77.4 mmol) dropwise. The resulting solution was stirred at RT 3 h. The reaction was diluted with H$_2$O and extracted with DCM. The combined extracts were concentrated to give an oil which was purified by silica gel chromatography to afford Compound 6 (5.6 g, 75.7%).

¹HNMR(CDCl₃, 300 MHz) δ 5.4-5.5 (s, 1H), 5.5-5.6 (s, 1H), 6.4-6.5 (s, 1H), 7.3 (s, 1H), 7.4-7.5 (m, 3H), 7.6-7.7 (d, 2H), 7.7-7.8 (s, 1H), 8.2-8.4 (s, 1H).

6. To a solution of Compound 6 (5.6 g, 19.5 mmol) in EtOH (60 mL) was added NaBH₄ (21.9 g, 58.4 mmol) in three portions. The resulting solution was stirred at RT for TLC. The reaction was concentrated, diluted with H₂O and extracted with EA. The combined extracts were concentrated to give a crude oil and purified by silica gel chromatography to afford Intermediate 2 (3.8 g, 66.6%).

¹HNMR (CDCl₃, 300 MHz) δ 2.0-2.1 (d, 3H), 6.4-6.5 (s, 1H), 6.9-7.0 (s, 1H), 7.2 (d, 1H), 7.6-7.7 (m, 1H), 7.7-7.8 (d, 1H), 7.9-8.0 (d, 1H).

Example SBX082

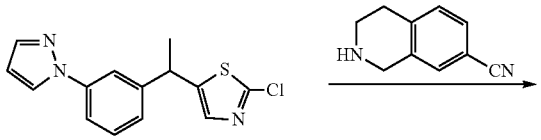

Intermediate 2

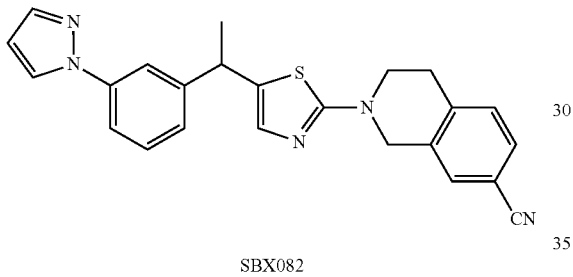

SBX082

Procedure:

To a solution of Intermediate 2 (300 mg, 1 mmol) in DMSO (3 mL) were added 1,2,3,4-tetrahydroisoquinoline-7-carbonitrile hydrochloride (290 mg, 1.5 mmol) and K₂CO₃ (270 mg, 2 mmol) and the resulting mixture was stirred at 140° C. overnight, cooled to RT, diluted with water and extracted with EA. The combined extracts were washed with water, brine, dried over anhydrous Na₂SO₄, filtered and concentrated to give an oil. The crude product was purified by silica gel chromatography to afford SBX082 (15 mg, 3.5%).

¹HNMR (CDCl₃, 300 MHz) δ 1.6-1.8 (d, 3H), 3.0 (m, 2H), 3.6-3.8 (s, 2H), 4.2-4.3 (m, 1H), 4.6-4.7 (s, 2H), 6.4-6.5 (s, 1H), 6.9-7.0 (s, 1H), 7.2 (d, 1H), 7.4-7.6 (m, 4H), 7.6-7.7 (m, 1H), 7.7-7.8 (d, 1H), 7.9-8.0 (d, 1H). LC-MS: m/z=412 (M+1)⁺.

Example SBX084

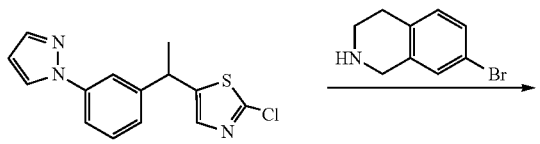

Intermediate 2

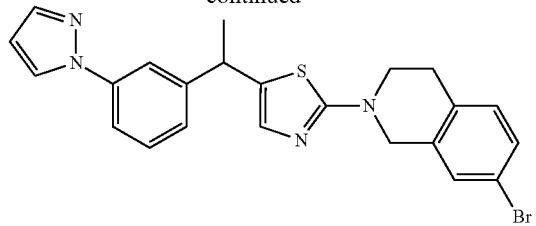

SBX084

Procedure:

Following the procedure described for Example SBX082, Intermediate 2 (300 mg, 1 mmol) and 7-bromo-1,2,3,4-tetrahydroisoquinoline hydrochloride (290 mg, 1.5 mmol) were converted to SBX084 (98 mg, 20.4%).

¹HNMR (CDCl₃, 300 MHz) δ 1.6-1.8 (d, 3H), 2.8-2.9 (m, 2H), 3.6-3.8 (s, 2H), 4.2-4.3 (m, 1H), 4.6-4.7 (s, 2H), 6.4-6.5 (s, 1H), 7.0-7.1 (s, 1H), 7.2 (d, 1H), 7.4-7.6 (m, 4H), 7.6-7.7 (m, 1H), 7.7-7.8 (d, 1H), 7.9-8.0 (d, 1H). LC-MS: m/z=465/467 (M+1)⁺.

Example SBX087

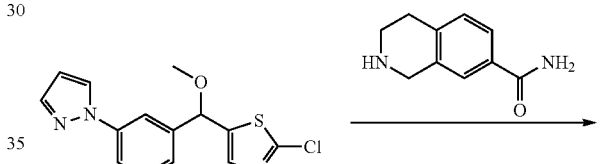

Intermediate 1

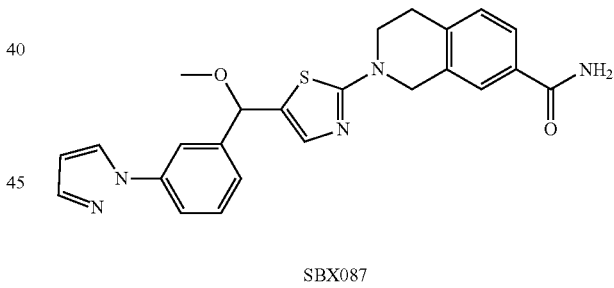

SBX087

Procedure:

To a solution of Intermediate 1 (300 mg, 1 mmol) in DMSO (3 mL) were added 1,2,3,4-tetrahydroisoquinoline-7-carboxamide hydrochloride (290 mg, 1.5 mmol)) and K₂CO₃ (270 mg, 2 mmol). The reaction mixture was stirred at 140° C. overnight. The mixture was cooled to RT, diluted with water and extracted with EA. The combined extracts were washed with water, brine, dried over anhydrous Na₂SO₄, filtered and concentrated to give an oil which was purified by silica gel chromatography to afford SBX087 (14 mg, 3.2%).

¹HNMR (CDCl₃, 300 MHz) δ 2.9-3.0 (m, 2H), 3.3-3.4 (s, 3H), 3.7-3.8 (m, 2H), 4.6-4.7 (s, 2H), 5.4-5.5 (s, 1H), 6.4-6.5 (s, 1H), 7.0-7.1 (s, 1H), 7.3 (s, 1H), 7.4-7.5 (m, 2H), 7.6-7.7 (d, 1H), 7.7-7.8 (d, 2H), 7.9-8.0 (s, 1H). LC-MS: m/z=446 (M+1)⁺.

Example SBX088

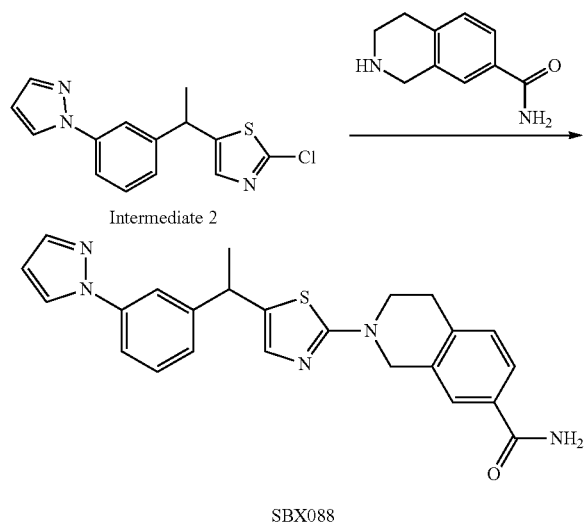

Intermediate 2

SBX088

Procedure:

Following the procedure described for Example SBX082, Intermediate 2 (300 mg, 1 mmol) and 1,2,3,4-tetrahydroisoquinoline-7-carboxamide hydrochloride (290 mg, 1.5 mmol) were converted to SBX088 (52 mg, 11.7%).

$^1$HNMR (CDCl$_3$, 300 MHz) δ 1.6-1.8 (d, 3H), 2.8-2.9 (m, 2H), 3.6-3.8 (s, 2H), 4.2-4.3 (m, 1H), 4.6-4.7 (s, 2H), 6.4-6.5 (s, 1H), 7.0-7.1 (s, 1H), 7.2 (d, 1H), 7.4-7.6 (m, 4H), 7.6-7.7 (m, 1H), 7.7-7.8 (d, 1H), 7.9-8.0 (d, 1H). LC-MS: m/z=430.5 (M+1)$^+$.

Assessing Antiviral Activity Against Human Cytomegalovirus (HCMV)

To assess their antiviral activity, some compounds were tested against human cytomegalovirus (HCMV) in vitro. Human MRC5 cells were grown in Dulbecco's Modified Eagle Medium (DMEM) supplemented with 10% fetal bovine serum (FBS) and infected with an HCMV variant expressing GFP tagged pUL99 (the product of late viral UL99 gene) at a multiplicity of 1 infectious unit (IU) per cell. One hour later, medium of the cells was replaced with fresh medium containing the indicated compounds at 50, 25, 12.5, 6.25, 3.13, 1.56, 0.78, 0.39 μM or the carrier in which the compounds are dissolved (DMSO). Final concentration of DMSO was 0.5% in each treatment. Virus yield in the culture supernatant was determined at 96 hours after infection by infecting fresh MRC5 cells and assaying viral IE1 protein expression. Results were plotted using either Prism Software or CDD Vault (CDD Vault was developed by Collaborative Drug Discovery, Inc., 1633 Bayshore Hwy, Suite 342, Burlingame, Calif. 94010) in order to calculate IC50s.

Alternatively, antiviral efficacy of some compounds was assessed by inhibition of HCMV replication during in vitro replication assays. Briefly, confluent monolayers of MRC5 fibroblasts in a 96 well plate format (~1.0×10^4 cells/well) were infected with an AD169 strain of HCMV for one hour. After the initial incubation hour, virus containing media was removed and 100 ul of media with sequential dilutions of FORGE compounds added to each well. The concentrations of the FORGE compounds were 50 μM, 25 μM, 12.5 μM, 6.25 μM, 3.125 μM, 1.56 μM, and 0.78125 μM as well as a vehicle control (0.5% DMSO). The concentration of DMSO was constant between all conditions. Assays were performed in duplicate. Infected plates were returned to the incubator and the viral infection was allowed to progress for four days. On the fourth day, 50 μL of cell free supernatant was collected from each well and used to infect a new 96 well plate seeded with a confluent monolayer of MRC5 fibroblasts along with 50 μL of media to bring the total volume to 100 μL. The next day the media was removed and the infected monolayer was fixed with cold methanol, and Immediate Early proteins were detected by immunofluorescence assays to quantify the number of cells that were infected with HCMV. IE gene expression was quantified within five random fields within each well and corresponding numbers were utilized to determine viral replication. Results from each well were normalized to the vehicle control well so as to allow a percent reduction from no drug treatment to be calculated. Results were plotted using either Prism Software or CDD Vault in order to calculate IC50s.

As shown in Table 3, 28 of the tested compounds showed antiviral activity against HCMV at IC$_{50}$ values <50 μM without inducing cytotoxicity in the cells at antiviral concentrations.

TABLE 3

| Example | Structure | HCMV IC$_{50}$ |
|---|---|---|
| Example 1 | 8x | 21.4 μM |

TABLE 3-continued

| Example | Structure | HCMV IC$_{50}$ |
|---|---|---|
| Example 2 | 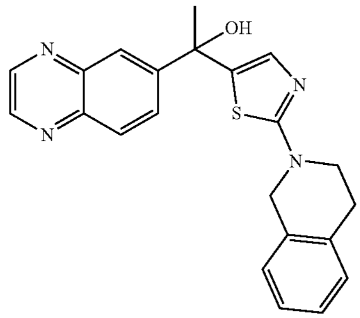 [SMILES: CC(O)(c1ccc2nccnc2c1)c1cnc(N2CCc3ccccc3C2)s1] | 24.0 μM |
| Example 3 | 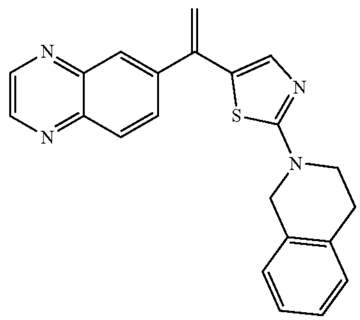 [SMILES: C=C(c1ccc2nccnc2c1)c1cnc(N2CCc3ccccc3C2)s1] | >50 μM |
| Example 4 | 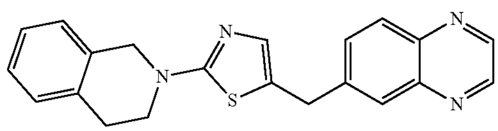 [SMILES: c1ccc2c(c1)CCN(c1ncc(Cc3ccc4nccnc4c3)s1)C2] | 5.6 μM |
| Example 5 | 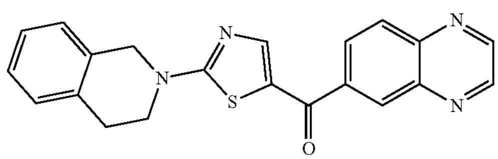 [SMILES: O=C(c1ccc2nccnc2c1)c1cnc(N2CCc3ccccc3C2)s1] | >50 μM |
| Example 6 | 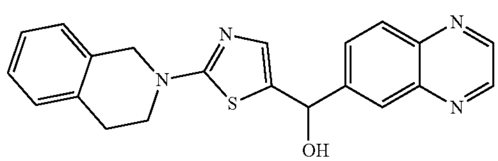 [SMILES: OC(c1ccc2nccnc2c1)c1cnc(N2CCc3ccccc3C2)s1] | 5.1 μM |
| Example 7 | 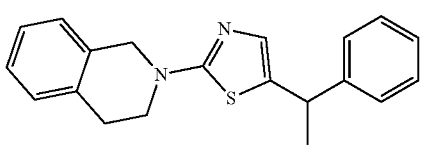 [SMILES: CC(c1ccccc1)c1cnc(N2CCc3ccccc3C2)s1] | >50 μM |
| Example 8 | 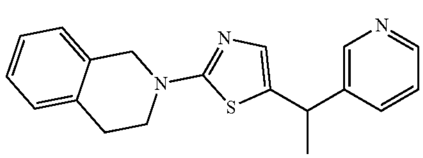 [SMILES: CC(c1cccnc1)c1cnc(N2CCc3ccccc3C2)s1] | 16.4 μM |
| Example 9 | 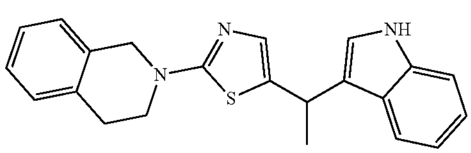 [SMILES: CC(c1cnc(N2CCc3ccccc3C2)s1)c1c[nH]c2ccccc12] | 12.7 μM |

TABLE 3-continued
| Example | Structure | HCMV IC$_{50}$ |
|---|---|---|
| Example 10 | 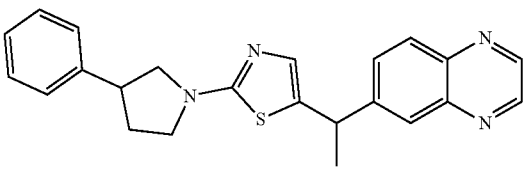 [SMILES: CC(c1ccc2nccnc2c1)c1cnc(N2CCC(c3ccccc3)C2)s1] | >25 μM |
| Example 11 | 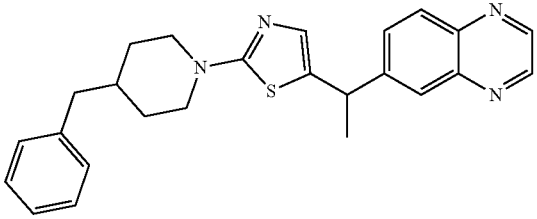 [SMILES: CC(c1ccc2nccnc2c1)c1cnc(N2CCC(Cc3ccccc3)CC2)s1] | >25 μM |
| Example 12 | 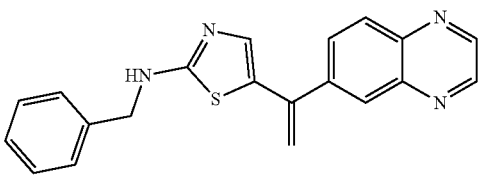 [SMILES: C=C(c1ccc2nccnc2c1)c1cnc(NCc2ccccc2)s1] | >50 μM |
| Example 13 | 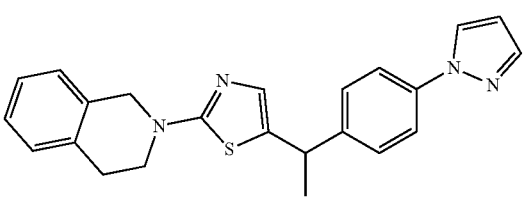 [SMILES: CC(c1ccc(-n2cccn2)cc1)c1cnc(N2CCc3ccccc3C2)s1] | 3.6 μM |
| Example 14 | 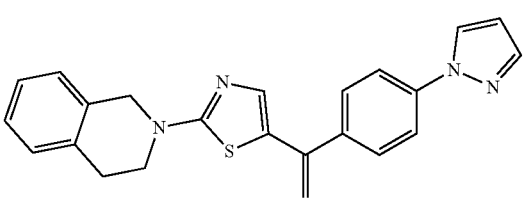 [SMILES: C=C(c1ccc(-n2cccn2)cc1)c1cnc(N2CCc3ccccc3C2)s1] | 28.7 μM |
| Example 15 | 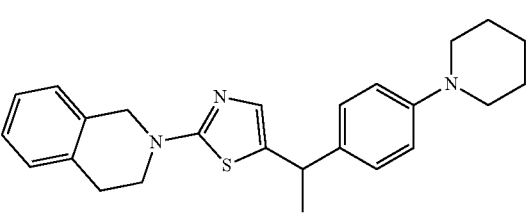 [SMILES: CC(c1ccc(N2CCCCC2)cc1)c1cnc(N2CCc3ccccc3C2)s1] | >25 μM |
| Example 16 | 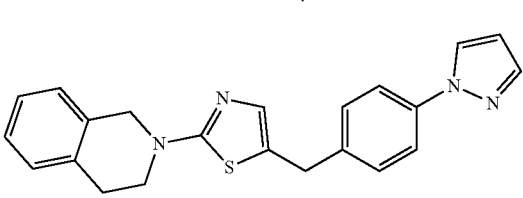 | 12.5 μM |
| Example 17 | 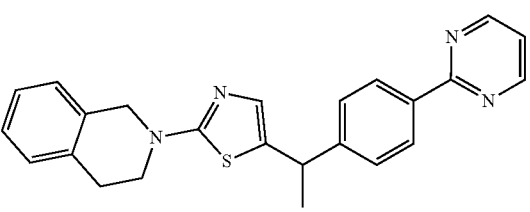 [SMILES: CC(c1ccc(-c2ncccn2)cc1)c1cnc(N2CCc3ccccc3C2)s1] | 4.2 μM |

TABLE 3-continued

| Example | Structure | HCMV IC$_{50}$ |
|---|---|---|
| Example 18 | 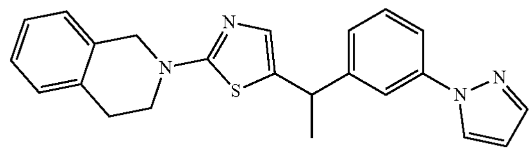 [SMILES: CC(c1cccc(-n2cccn2)c1)c1cnc(N2CCc3ccccc3C2)s1] | 1.6 μM |
| Example 19 | 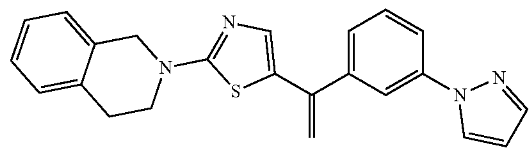 [SMILES: C=C(c1cccc(-n2cccn2)c1)c1cnc(N2CCc3ccccc3C2)s1] | 7.0 μM |
| Example 20 | 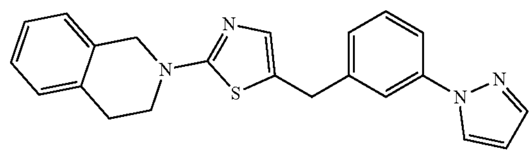 [SMILES: c1cc(Cc2cnc(N3CCc4ccccc4C3)s2)cc(-n2cccn2)c1] | 8.9 μM |
| Example 21 | 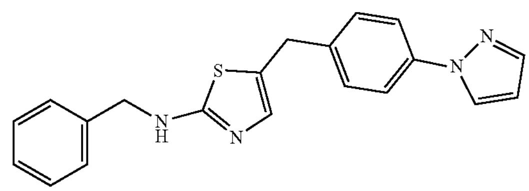 [SMILES: c1ccc(CNc2ncc(Cc3ccc(-n4cccn4)cc3)s2)cc1] | >50 μM |
| Example 22 | 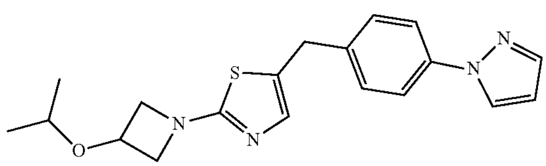 [SMILES: CC(C)OC1CN(c2ncc(Cc3ccc(-n4cccn4)cc3)s2)C1] | >50 μM |
| Example 23 | 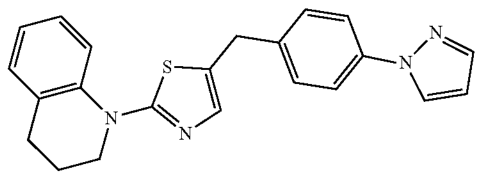 [SMILES: c1ccc2c(c1)CCCN2c1ncc(Cc2ccc(-n3cccn3)cc2)s1] | >50 μM |
| Example 24 | 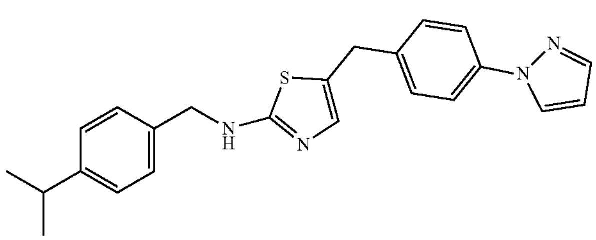 [SMILES: CC(C)c1ccc(CNc2ncc(Cc3ccc(-n4cccn4)cc3)s2)cc1] | >50 μM |
| Example 25 | 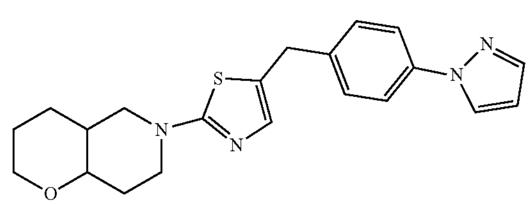 [SMILES: c1cnn(-c2ccc(Cc3cnc(N4CCC5OCCCC5C4)s3)cc2)c1] | 11 μM |

TABLE 3-continued

| Example | Structure | HCMV IC$_{50}$ |
|---|---|---|
| Example 26 | 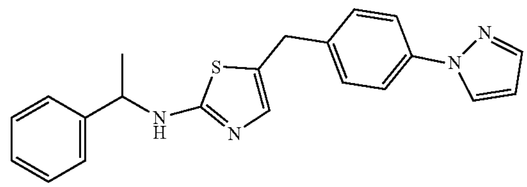 [SMILES: CC(Nc1ncc(Cc2ccc(-n3cccn3)cc2)s1)c1ccccc1] | >50 μM |
| Example 27 | 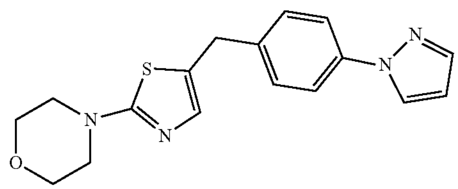 [SMILES: c1cnn(-c2ccc(Cc3cnc(N4CCOCC4)s3)cc2)c1] | 10.3 μM |
| Example 28 | 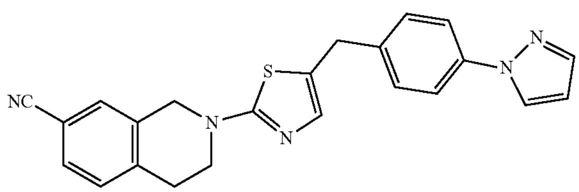 [SMILES: N#Cc1ccc2c(c1)CN(c1ncc(Cc3ccc(-n4cccn4)cc3)s1)CC2] | 9.7 μM |
| Example 29 | 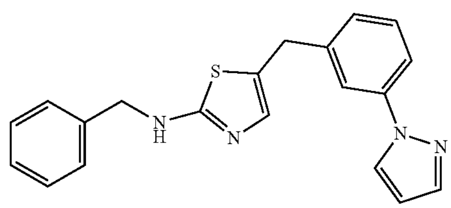 [SMILES: c1ccc(CNc2ncc(Cc3cccc(-n4cccn4)c3)s2)cc1] | >50 μM |
| Example 30 | 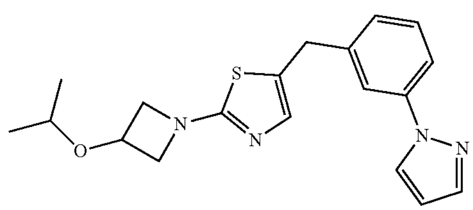 [SMILES: CC(C)OC1CN(c2ncc(Cc3cccc(-n4cccn4)c3)s2)C1] | 12 μM |
| Example 31 | 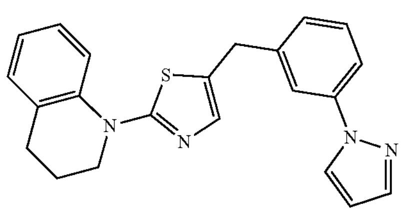 [SMILES: c1cc(Cc2cnc(N3CCCc4ccccc43)s2)cc(-n2cccn2)c1] | >50 μM |
| Example 32 | 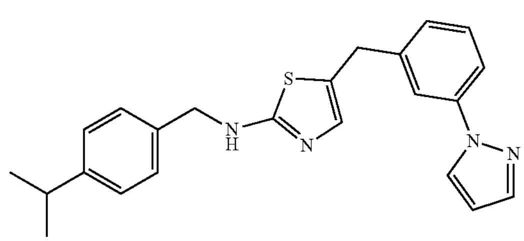 [SMILES: CC(C)c1ccc(CNc2ncc(Cc3cccc(-n4cccn4)c3)s2)cc1] | >50 μM |

TABLE 3-continued

| Example | Structure | HCMV IC$_{50}$ |
|---|---|---|
| Example 33 | 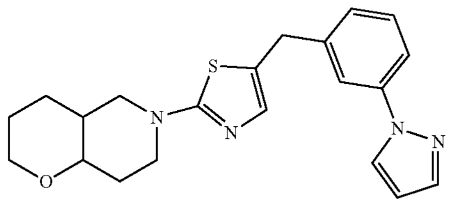 [SMILES: c1cc(Cc2cnc(N3CCC4OCCCC4C3)s2)cc(-n2cccn2)c1] | 11.5 μM |
| Example 34 | 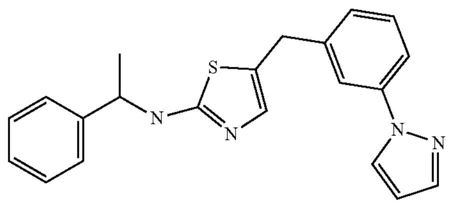 [SMILES: CC(Nc1ncc(Cc2cccc(-n3cccn3)c2)s1)c1ccccc1] | >50 μM |
| Example 35 | 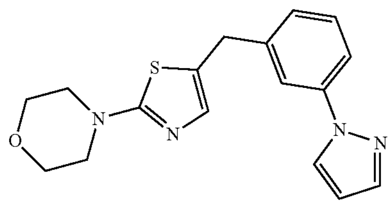 [SMILES: c1cc(Cc2cnc(N3CCOCC3)s2)cc(-n2cccn2)c1] | >27 μM |
| Example 36 | 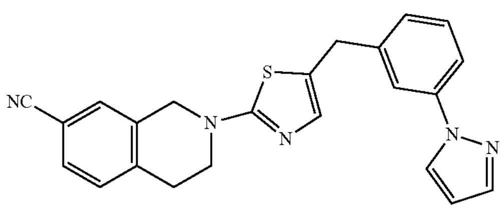 [SMILES: N#Cc1ccc2c(c1)CN(c1ncc(Cc3cccc(-n4cccn4)c3)s1)CC2] | 3.3 μM |
| Example SBX080 | 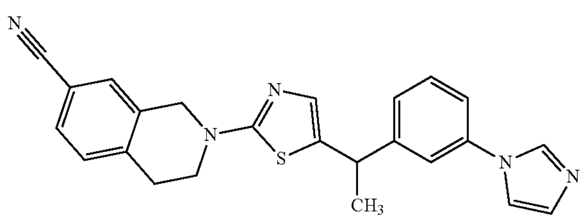 [SMILES: CC(c1cccc(-n2ccnc2)c1)c1cnc(N2CCc3ccc(C#N)cc3C2)s1] | 4.9 μM |
| Example SBX082 | 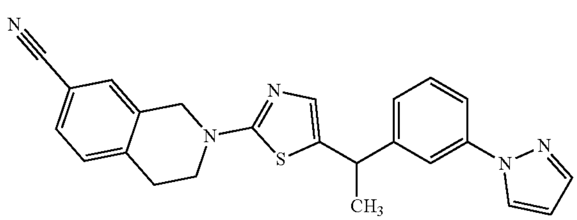 [SMILES: CC(c1cccc(-n2cccn2)c1)c1cnc(N2CCc3ccc(C#N)cc3C2)s1] | 7.3 μM |
| Example SBX084 | 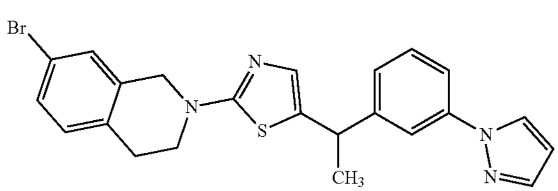 [SMILES: CC(c1cccc(-n2cccn2)c1)c1cnc(N2CCc3ccc(Br)cc3C2)s1] | 3.8 μM |

TABLE 3-continued

| Example | Structure | HCMV IC$_{50}$ |
| --- | --- | --- |
| Example SBX087 | 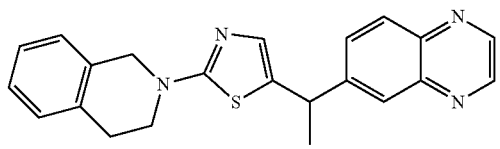 | 1.4 µM |
| Example SBX088 | 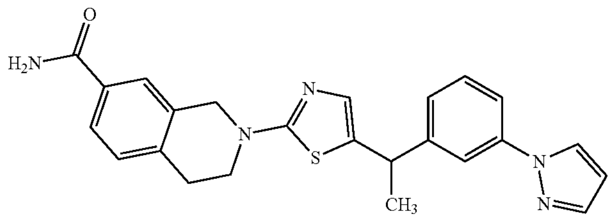 [SMILES: CC(c1cccc(-n2cccn2)c1)c1cnc(N2CCc3ccc(C(N)=O)cc3C2)s1] | 1.6 µM |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising a compound of Formula II or a pharmaceutically acceptable salt thereof:

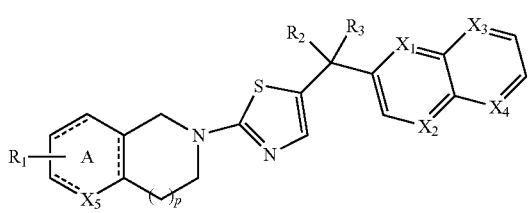

wherein $X_1$, $X_2$, $X_3$, and $X_4$ are independently selected from CH and N, p is 0 or 1, $R_1$ is H, halo, —CN, —NO$_2$, —C(O)NR$_6$R$_7$, or C(O)OR$_6$, $R_2$ is H or a lower straight or branched alkyl or alkenyl optionally substituted with one heteroatom selected of N and O, $R_3$ is H or OH, $R_6$ and $R_7$ are independently selected in each instance from H and lower straight chain or branched alkyl, when Ring A is aromatic, $X_5$ is CH, CR$_1$, or N, and when Ring A is not aromatic, $X_5$ is CH$_2$, CHR$_1$, O, S, or NR$_7$;

with the proviso that the compound is not:

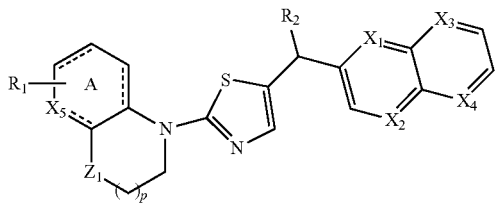

or a pharmaceutically acceptable salt thereof.

2. A composition comprising a compound of Formula III or a pharmaceutically acceptable salt thereof:

wherein $X_1$, $X_2$, $X_3$, and $X_4$ are independently selected from CH and N, p is 0 or 1, when p is 0, $Z_1$ is CH$_2$, when p is 1, $Z_1$ is CH$_2$, O, S, or NR$_7$;

$R_1$ is H, halo, —CN, —NO$_2$, —C(O)NR$_6$R$_7$, or C(O)OR$_6$, $R_2$ is H or a lower straight or branched alkyl or alkenyl optionally substituted with one heteroatom selected of N and O, $R_6$ and $R_7$ are independently selected in each instance from H and lower straight chain or branched alkyl, when Ring A is aromatic, $X_5$ is CH, CR$_1$, or N, and when Ring A is not aromatic, $X_5$ is CH$_2$, CHR$_1$, O, S, or NR$_7$.

3. A composition comprising a compound of Formula IV or a pharmaceutically acceptable salt thereof:

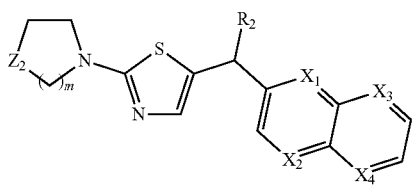

wherein $X_1$, $X_2$, $X_3$, and $X_4$ are independently selected from CH and N, m is 0, 1 or 2, $R_2$ is H or a lower straight or branched alkyl or alkenyl optionally substituted with one heteroatom selected of N and O, $R_6$ and $R_7$ are independently selected in each instance from H and lower straight chain or branched alkyl, when m=0 or 1, $Z_1$ is $CH_2$, and when m=2, $Z_2$ is $CH_2$, O, S, or $NR_7$.

4. A composition comprising a compound of Formula VI or a pharmaceutically acceptable salt thereof:

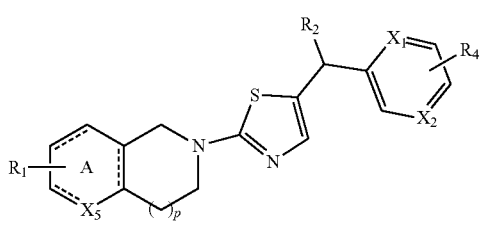

wherein $X_1$ and $X_2$ are independently selected from CH and N, p is 0 or 1, $R_1$ is H, halo, —CN, —$NO_2$, —C(O)$NR_6R_7$, or C(O)$OR_6$, $R_2$ is H or a lower straight or branched alkyl or alkenyl optionally substituted with one heteroatom selected of N and O, $R_4$ is H or a saturated 5- or 6-membered aryl or cycloalkyl with up to two heteroatoms selected from N, O and S, $R_6$ and $R_7$ are independently selected in each instance from H and lower straight chain or branched alkyl, when Ring A is aromatic, $X_5$ is CH, $CR_1$, or N, and when Ring A is not aromatic, $X_5$ is $CH_2$, $CHR_1$, O, S, or $NR_7$.

5. A composition comprising a compound of Formula VII or a pharmaceutically acceptable salt thereof:

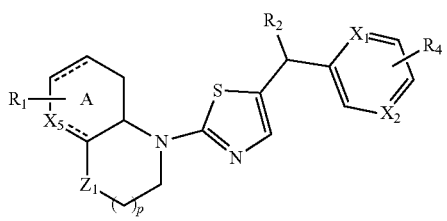

wherein $X_1$ and $X_2$ are independently selected from CH and N, p is 0 or 1, when p is 0, $Z_1$ is $CH_2$, when p is 1, $Z_1$ is $CH_2$, O, S, or $NR_7$, $R_1$ is H, halo, —CN, —$NO_2$, —C(O)$NR_6R_7$, or C(O)$OR_6$, $R_2$ is H or a lower straight or branched alkyl or alkenyl optionally substituted with one heteroatom selected of N and O, $R_4$ is H or a saturated 5- or 6-membered aryl or cycloalkyl with up to two heteroatoms selected from N, O and S, $R_6$ and $R_7$ are independently selected in each instance from H and lower straight chain or branched alkyl, when Ring A is aromatic, $X_5$ is CH, $CR_1$, or N, and when Ring A is not aromatic, $X_5$ is $CH_2$, $CHR_1$, O, S, or $NR_7$.

6. The composition of claim 4, wherein $R_4$ is in the meta or para position and is selected from the group consisting of pyrrole, imidazole, pyrazole, pyrazine, pyrimidine and pyridazine.

7. A method for treating a HCMV infection in a subject, the method comprising administering to the subject a therapeutically effective amount of a compound of Formula I:

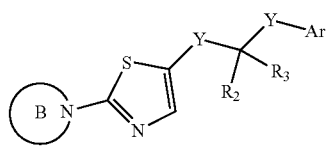

wherein:

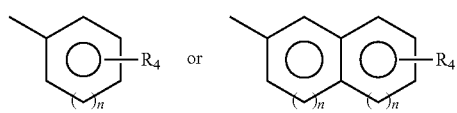

Ar is wherein each cyclic 5- or 6-membered ring in Ar optionally contains up to two N heteroatoms, Y is, independently in each instance, $CH_2$ or a bond, Ring B is selected from the group consisting of:

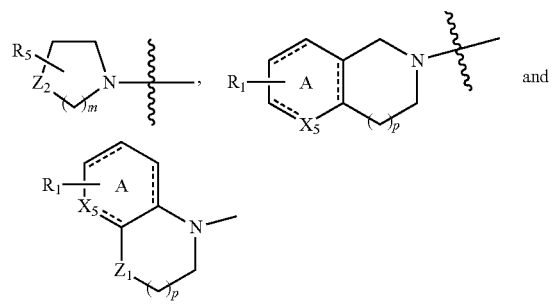

m is 0, 1 or 2, n is, independently in each instance, 0 or 1, p is 0 or 1, when p is 0, $Z_1$ is $CH_2$, when p is 1, $Z_1$ is $CH_2$, O, S, or $NR_7$, $R_1$ is H, halo, —CN, —$NO_2$, —C(O)$NR_6R_7$, or C(O)$OR_6$, $R_2$ is H or a lower straight or branched alkyl or alkenyl optionally substituted with one heteroatom selected of N and O, $R_3$ is H or OH, $R_4$ is H or a saturated 5- or 6-membered aryl or cycloalkyl with up to two heteroatoms selected from N, O and S, $R_5$ is H, —$OR_7$, or —$NR_6R_7$, R₆ and R₇ are independently selected in each instance from H and lower straight chain or branched alkyl, when Ring A is aromatic, $X_5$ is CH, $CR_1$, or N, when Ring A is not aromatic, $X_5$ is $CH_2$, $CHR_1$, O, S, or $NR_7$, when m=0 or 1, $Z_1$ is $CH_2$, and when m=2, $Z_2$ is $CH_2$, O, S, or $NR_7$;

or a pharmaceutically acceptable salt thereof, with the proviso that the compound is not:

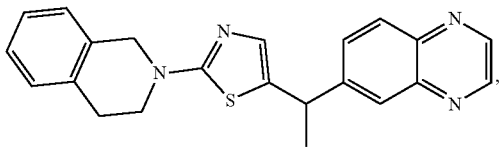

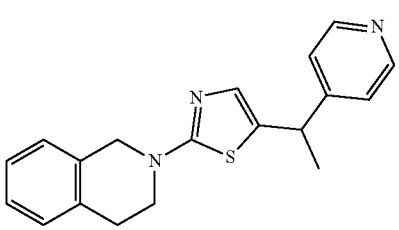

or a pharmaceutically acceptable salt thereof.

8. The method of claim 7, wherein the compound of Formula I is a compound of Formula II or a pharmaceutically acceptable salt thereof:

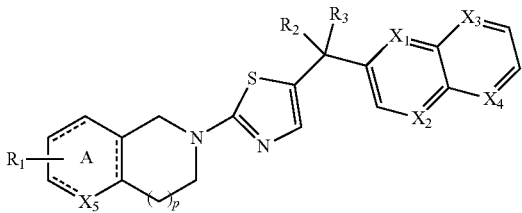

wherein $X_1$, $X_2$, $X_3$, and $X_4$ are independently selected from CH and N, with the proviso that the compound is not:

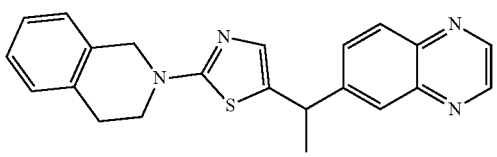 [SMILES: CC(c1ccc2nccnc2c1)c1cnc(N2CCc3ccccc3C2)s1]

or a pharmaceutically acceptable salt thereof.

9. The method of claim 7, wherein the compound of Formula I is a compound of Formula III or a pharmaceutically acceptable salt thereof:

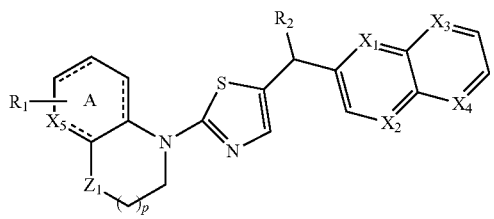

wherein $X_1$, $X_2$, $X_3$, and $X_4$ are independently selected from CH and N.

10. The method of claim 7, wherein the compound of Formula I is a compound of Formula IV or a pharmaceutically acceptable salt thereof:

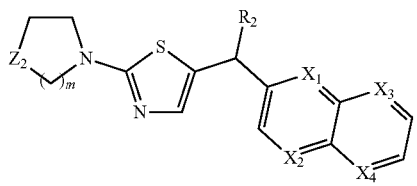

wherein $X_1$, $X_2$, $X_3$, and $X_4$ are independently selected from CH and N.

11. The method of claim 7, wherein the compound of Formula I is a compound of Formula V or a pharmaceutically acceptable salt thereof:

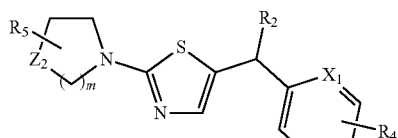

wherein $X_1$ and $X_2$ are independently selected from CH and N.

12. The method of claim 7, wherein the compound of Formula I is a compound of Formula VI or a pharmaceutically acceptable salt thereof:

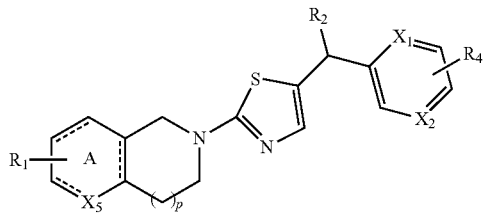

wherein $X_1$ and $X_2$ are independently selected from CH and N.

13. The method of claim 7, wherein the compound of Formula I is a compound of Formula VII or a pharmaceutically acceptable salt thereof:

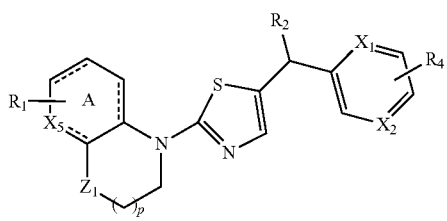
wherein $X_1$ and $X_2$ are independently selected from CH and N.
14. The method of claim 11, wherein $R_4$ is in the meta or para position and is selected from the group consisting of pyrrole, imidazole, pyrazole, pyrazine, pyrimidine and pyridazine.
15. The method of claim 7, wherein the compound of Formula I is selected from the group consisting of:
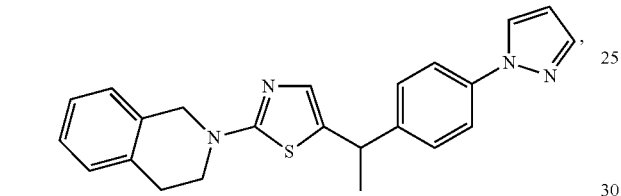
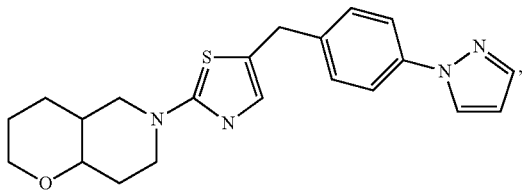
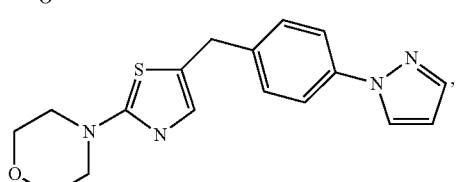
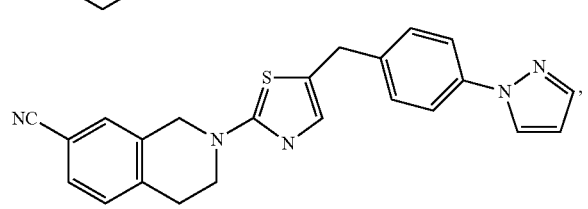
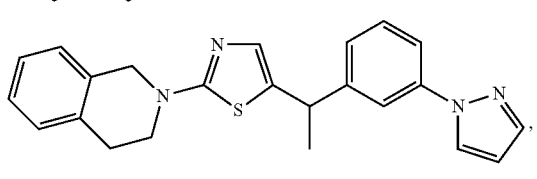
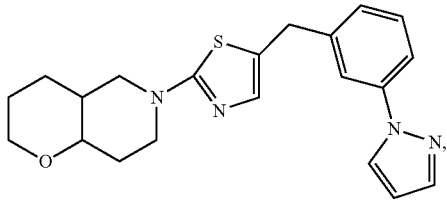
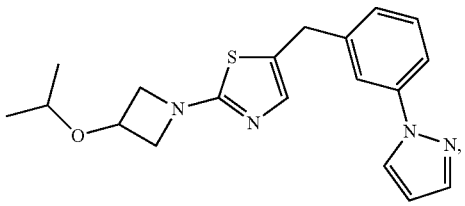
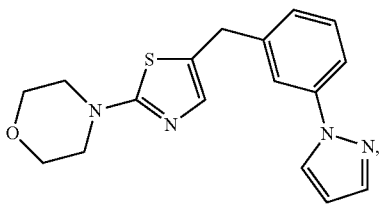
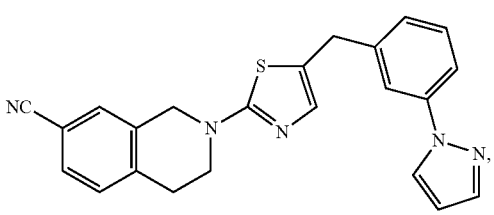
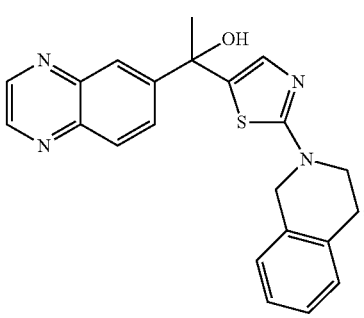
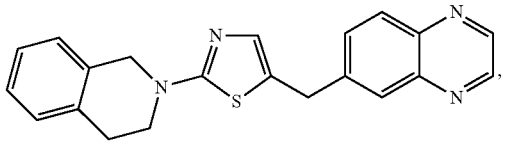
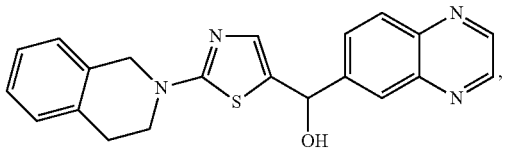
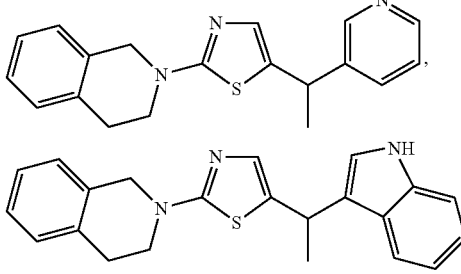
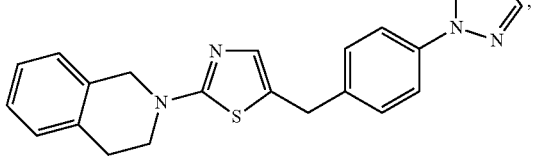

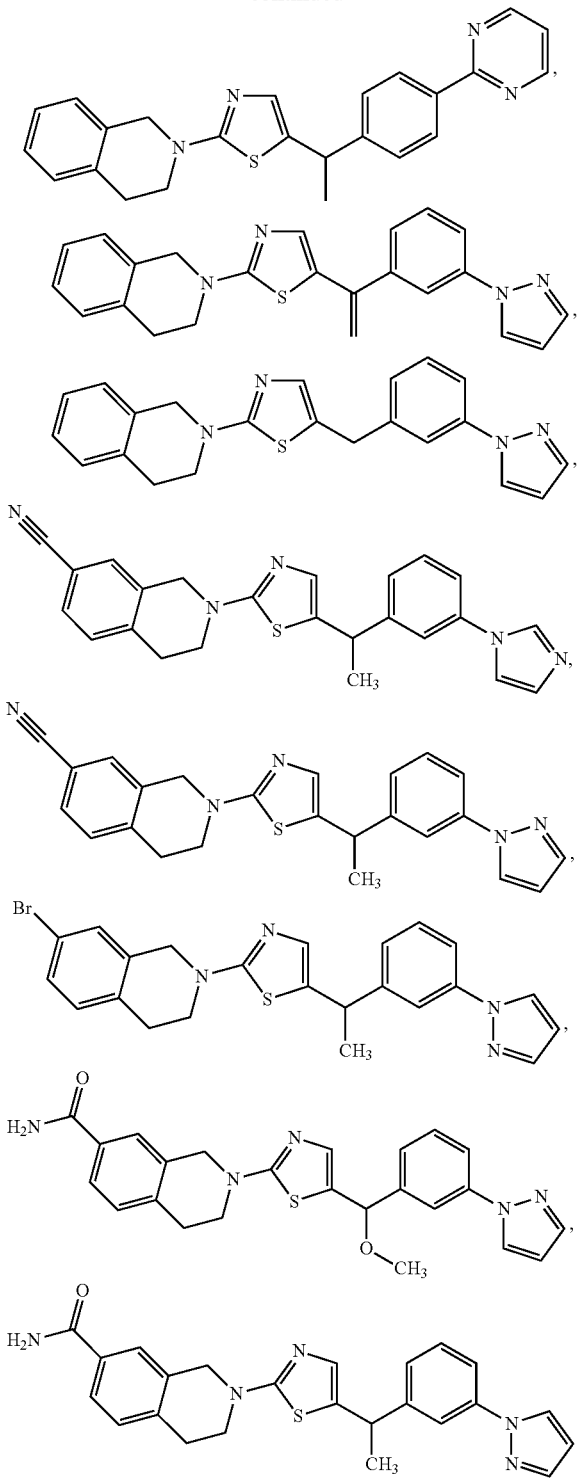

and pharmaceutically acceptable salts thereof.

16. The method of claim 7, wherein the method further comprises administering a therapeutically effective amount of an antiviral agent.

17. The method of claim 16, wherein the antiviral agent is selected from the group consisting of: acyclovir, docosanol, ribarivin, interferons, and the like; cellulose acetate, carbopol and carrageenan, pleconaril, amantidine, amantidine, fomivirsen, zidovudine, lamivudine, zanamivir, oseltamivir, brivudine, abacavir, adefovir, amprenavir, arbidol, atazanavir, atripla, cidofovir, combivir, edoxudine, efavirenz, emtricitabine, enfuvirtide, entecavir, famciclovir, fosamprenavir, foscarnet, fosfonet, ganciclovir, gardasil, ibacitabine, imunovir, idoxuridine, imiquimod, indinavir, inosine, integrase inhibitor, lamivudine, lopinavir, loviride, mk-0518, maraviroc, moroxydine, nelfinavir, nevirapine, nexavir, nucleotide and/or nucleoside analogues, oseltamivir, penciclovir, peramivir, podophyllotoxin, rimantadine, ritonavir, saquinavir, stavudine, tenofovir, tenofovir disoproxil, tipranavir, trifluridine, trizivir, tromantadine, truvada, valaciclovir, valganciclovir, vicriviroc, vidarabine, viramidine, zalcitabine, morpholino oligonucleotides, ribozyme, protease inhibitors, an assembly inhibitor, zidovudine, brincidofovir, favipiravir, nitoxanide, letermovir, maribavir, CMX157 or a combination thereof.

18. The composition of claim 4, wherein $R_4$ is in the meta or para position and is selected from the group consisting of pyrrole, imidazole, pyrazole, pyrazine, pyrimidine and pyridazine.

19. The composition of claim 5, wherein $R_4$ is in the meta or para position and is selected from the group consisting of pyrrole, imidazole, pyrazole, pyrazine, pyrimidine and pyridazine.

20. The method of claim 12, wherein $R_4$ is in the meta or para position and is selected from the group consisting of pyrrole, imidazole, pyrazole, pyrazine, pyrimidine and pyridazine.

21. The method of claim 13, wherein $R_4$ is in the meta or para position and is selected from the group consisting of pyrrole, imidazole, pyrazole, pyrazine, pyrimidine and pyridazine.

22. The composition of claim 6, wherein the compound is selected from the group consisting of:

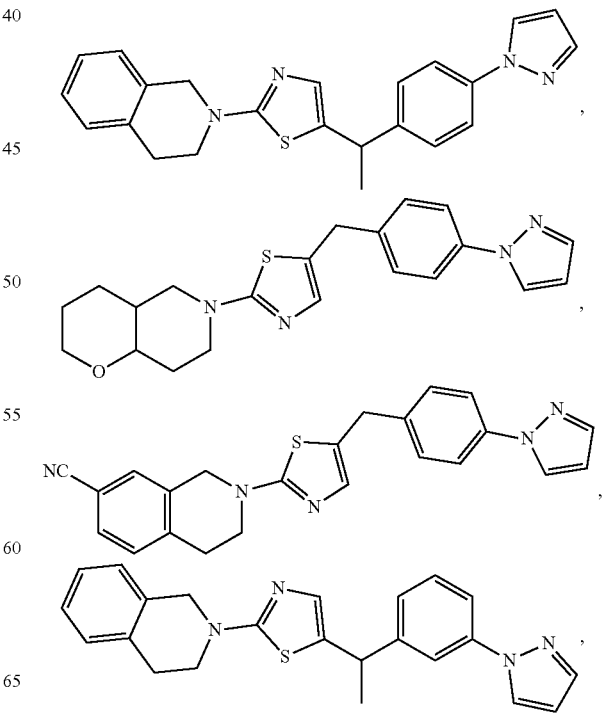

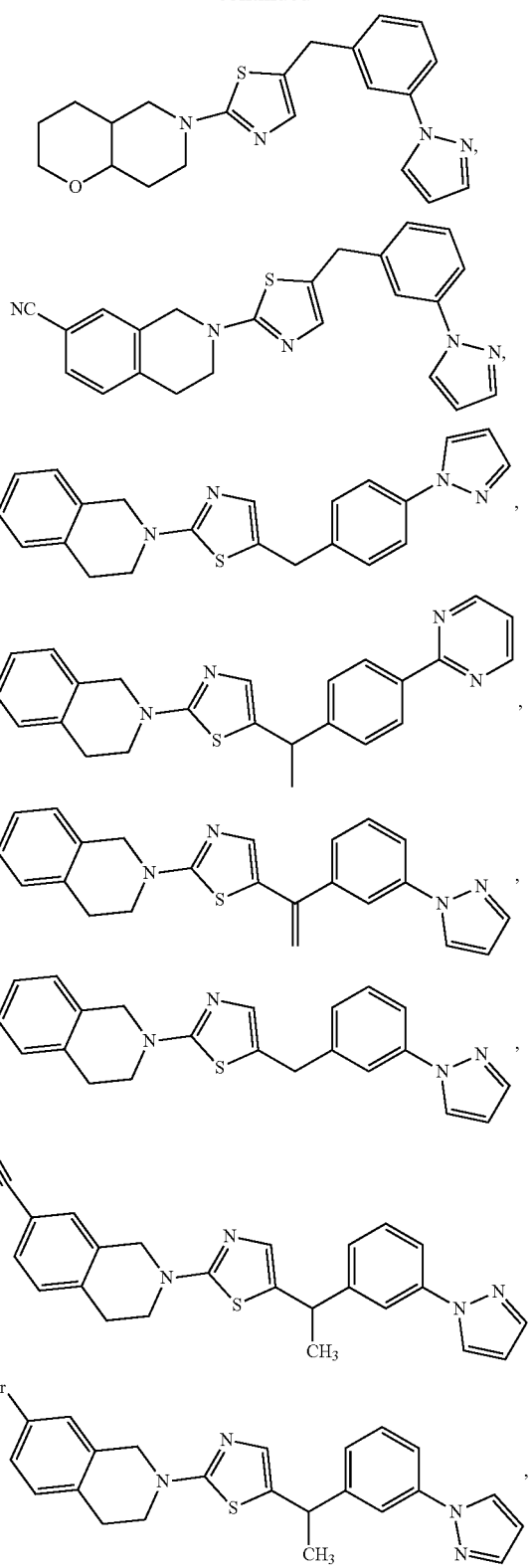
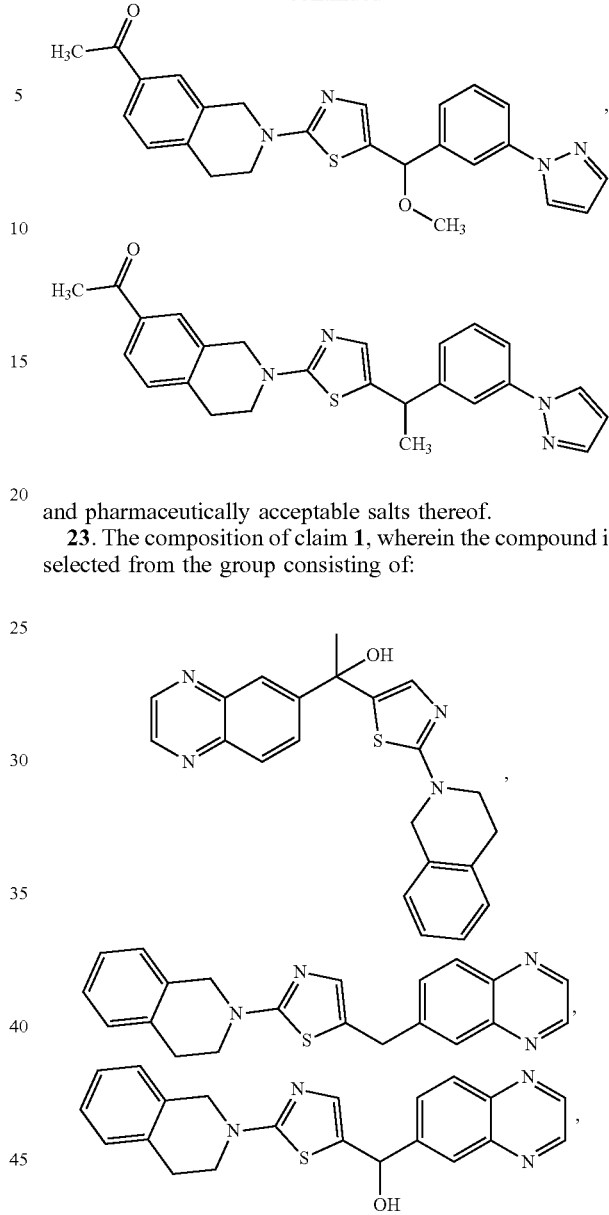
and pharmaceutically acceptable salts thereof.
23. The composition of claim 1, wherein the compound is selected from the group consisting of:
and pharmaceutically acceptable salts thereof.
24. The composition of claim 4, wherein the compound is selected from the group consisting of:
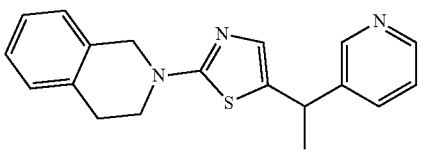 [SMILES: CC(c1cccnc1)c1cnc(N2CCc3ccccc3C2)s1]
and pharmaceutically acceptable salts thereof.
* * * * *